US00RE48415E

(19) United States
(12) Reissued Patent
Yoshikawa et al.

(10) Patent Number: US RE48,415 E
(45) Date of Reissued Patent: Feb. 2, 2021

(54) X-RAY PHOTOGRAPHY APPARATUS

(71) Applicant: J. Morita Manufacturing Corporation, Kyoto (JP)

(72) Inventors: Hideki Yoshikawa, Kyoto (JP); Makoto Honjo, Kyoto (JP)

(73) Assignee: J. Morita Manufacturing Corporation, Kyota (JP)

(21) Appl. No.: 15/599,389

(22) Filed: May 18, 2017

Related U.S. Patent Documents

Reissue of:

(64) Patent No.: 9,036,775
Issued: May 19, 2015
Appl. No.: 14/074,462
Filed: Nov. 7, 2013

(30) Foreign Application Priority Data

Nov. 8, 2012 (JP) ..... 2012-246514
Dec. 26, 2012 (JP) ..... 2012-283099

(51) Int. Cl.
*A61B 6/14* (2006.01)
*A61B 6/03* (2006.01)
(Continued)

(52) U.S. Cl.
CPC ..... *A61B 6/145* (2013.01); *A61B 6/035* (2013.01); *A61B 6/06* (2013.01); *A61B 6/14* (2013.01);
(Continued)

(58) Field of Classification Search
CPC ..... A61B 6/035; A61B 6/0457; A61B 6/0478; A61B 6/06; A61B 6/14; A61B 6/145;
(Continued)

(56) References Cited

U.S. PATENT DOCUMENTS 5,692,027 A 11/1997 Yoshimura et al.
6,052,428 A 4/2000 Nakano et al.
(Continued)

FOREIGN PATENT DOCUMENTS

DE 101 20 649 A1 12/2001
DE 10 2004 050172 A1 3/2006
(Continued)

OTHER PUBLICATIONS

Office Action issued in corresponding European Patent Application (EP Application No. 13 005 188.1), dated Nov. 17, 2016 (Nov. 17, 2016).
(Continued)

*Primary Examiner* — Woo H. Choi
(74) *Attorney, Agent, or Firm* — DLA Piper LLP (US)

(57) ABSTRACT

An X-ray photography apparatus including: a turning arm that supports an X-ray generator and an X-ray detector which are opposed to each other so that the head of a patient can be interposed therebetween, and a moving mechanism that includes a turning part and a moving part. The turning part turns the turning arm about a turning axis with respect to the head. The moving part moves the turning arm relative to the head in a direction perpendicular to the turning axis. The X-ray photography apparatus also includes: an image processor that generates an X-ray image, a photographic region designation part that designates part of a row of teeth along a dental arch as a pseudo intraoral radiography region, and an X-ray forming mechanism that changes the irradiation direction in which the head is irradiated with an X-ray relative to the axial direction of the body axis of the patient.

6 Claims, 37 Drawing Sheets

(51) Int. Cl.
*A61B 6/06* (2006.01)
*A61B 6/00* (2006.01)
*A61B 6/04* (2006.01)

(52) U.S. Cl.
CPC ..... *A61B 6/4476* (2013.01); *A61B 6/469* (2013.01); *A61B 6/5223* (2013.01); *A61B 6/0478* (2013.01); *A61B 6/0487* (2020.08); *A61B 6/42* (2013.01)

(58) Field of Classification Search
CPC ..... A61B 6/42; A61B 6/4476; A61B 6/469; A61B 6/5223
See application file for complete search history.

(56) References Cited

U.S. PATENT DOCUMENTS

| | | | | |
|---|---|---|---|---|
| 6,493,415 | B1 * | 12/2002 | Arai et al. | A61B 6/14 378/38 |
| 6,940,948 | B1 * | 9/2005 | Tretiakov | A61B 6/00 378/146 |
| 9,668,705 | B2 * | 6/2017 | Yamakawa | A61B 6/14 |
| 2008/0232540 | A1 * | 9/2008 | Yoshimura et al. | 378/4 |
| 2009/0041191 | A1 * | 2/2009 | Suzuki et al. | 378/98.5 |
| 2010/0067650 | A1 * | 3/2010 | Arai | A61B 6/032 378/16 |
| 2010/0074505 | A1 * | 3/2010 | Oogami | A61B 6/00 382/132 |
| 2011/0038519 | A1 | 2/2011 | Nakai et al. | |
| 2011/0064188 | A1 | 3/2011 | Suzuki et al. | |
| 2013/0182822 | A1 * | 7/2013 | Sakaguchi | A61B 6/022 378/42 |
| 2013/0251101 | A1 * | 9/2013 | Saito | A61B 6/547 378/20 |
| 2014/0126686 | A1 * | 5/2014 | Sadakane et al. | 378/13 |

FOREIGN PATENT DOCUMENTS

| | | | |
|---|---|---|---|
| DE | 10 2005 004502 | A1 | 8/2006 |
| DE | 10 2010 040096 | A1 | 3/2012 |
| EP | 2730227 | A1 | 5/2014 |
| EP | 2 774 540 | A1 | 9/2014 |
| EP | 2774542 | A1 | 9/2014 |
| JP | 6-285059 | | 10/1994 |
| JP | 7-327985 | | 12/1995 |
| JP | 7-327985 | A | 12/1995 |
| JP | 2003-245277 | A | 9/2003 |
| JP | P2006-130037 | A | 5/2006 |
| JP | 2007-29168 | A | 2/2007 |
| JP | 2007-136163 | A | 6/2007 |
| JP | P2007-144136 | A | 6/2007 |
| JP | P3983664 | | 9/2007 |
| JP | P2008-510504 | A | 4/2008 |
| JP | 2009-136665 | A | 6/2009 |
| JP | 2010-246855 | A | 11/2010 |
| JP | 2011-152411 | A | 8/2011 |
| JP | P2011-206534 | A | 10/2011 |
| WO | WO 2009/063974 | A | 5/2009 |

OTHER PUBLICATIONS

The Extended European Search Report dated Sep. 25, 2020, of counterpart European Application No. 20184010.5.

* cited by examiner

X-RAY PHOTOGRAPHY APPARATUS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

1. Field of the Invention

The present invention relates to an X-ray photography apparatus.

2. Description of the Background Art

Conventionally what is called intraoral radiography (dental radiography), in which an X-ray detection means (such as an X-ray film and an X-ray sensor panel) is set in the oral cavity of a patient to photograph part of a row of teeth or gums, is performed in X-ray photography of the dental field. Because only a local region is irradiated with an X-ray in the intraoral radiography, advantageously the photographing is simply performed and X-ray exposure is reduced. However, it is necessary to dispose in advance the X-ray detection means in the oral cavity of the patient, and thus a large burden is placed on the patient.

Therefore, Japanese Patent Application Laid-Open No. 2007-136163 has made a proposal that panoramic photography is performed using a panoramic image photographing device and a tomographic image of part of the row of teeth or the gums is acquired using the frame data obtained by the panoramic photography. In the panoramic photography, the X-ray is detected using an X-ray detector disposed outside the head of a patient. For this reason, the intraoral radiography can be performed in a pseudo manner while the burden on the patient is reduced.

The conventional intraoral radiography is roughly divided into two: an intraoral radiography by a paralleling technique and an intraoral radiography by a bisecting angle technique. In the intraoral radiography performed by the paralleling technique, part of the row of teeth or the gums is irradiated with the X-ray such that the X-ray is orthogonal to the tooth axis of the tooth. In the case that part of the row of teeth or the gums is irradiated with the X-ray such that the X-ray is not orthogonal to the tooth axis, there is a risk that an X-ray image becomes such an image that the tooth is obliquely looked down from above or that the tooth is obliquely looked up from below, and possibly the image of the tooth is taken shorter (or longer) than in reality. The X-ray image is not desirable in an image diagnosis. Advantageously the problem is eliminated in the intraoral radiography by the paralleling technique.

On the other hand, in the intraoral radiography performed by the bisecting angle technique, part of the row of teeth or the gums is irradiated with the X-ray such that the X-ray is orthogonal to the line bisecting the angle formed by the tooth axis of the tooth and an X-ray film. In this case, because the X-ray is obliquely incident to the target tooth, the image of the tooth is taken shorter than in reality. However, the length of the tooth viewed in the X-ray irradiation direction is equal to the length of the image of the tooth taken in the X-ray film. Therefore, in the intraoral radiography by the bisecting angle technique, advantageously an observer can directly observe the tooth viewed in the X-ray irradiation direction as an X-ray photograph.

In the X-ray photography apparatus disclosed in Japanese Patent Application Laid-Open No. 2007-136163, the X-ray irradiation angle is not particularly changed during the panoramic photography. Therefore, the X-ray irradiation angle is undesirable with respect to the interest tooth, and the tomographic image equivalent to the X-ray image obtained by the intraoral radiography is hardly acquired.

SUMMARY OF THE INVENTION

The present invention is directed to an X-ray photography apparatus.

In accordance with one aspect of the present invention, an X-ray photography apparatus of the present invention includes:

a support that supports an X-ray generator and an X-ray detector while the X-ray generator and the X-ray detector are opposed (or faced) to each other so that the head of a patent can be interposed therebetween, the X-ray detector outputting an electric signal according to the intensity of an incident X-ray;

a moving mechanism that includes a turning part and a moving part, the turning part relatively turning the X-ray generator and the X-ray detector about the head of the patient by turning the support relative to the head about a predetermined turning axis, and the moving part moving the support relative to the head of the patient in a direction perpendicular to the turning axis;

a photographic region designation part that designates part of a row of teeth along a dental arch as a pseudo intraoral radiography region;

an irradiation direction changing part that relatively changes the X-ray irradiation direction in which the head of the patient is irradiated with the X-ray with respect to the axial direction of a body axis of the patient; and a controller that controls the moving mechanism and the irradiation direction changing part, the controller controlling the moving mechanism while changing the X-ray irradiation direction according to the position of the pseudo intraoral radiography region, and the position of the pseudo intraoral radiography region being designated by the photographic region designation part.

In the conventional intraoral radiography, it is necessary to dispose the X-ray film in the mouth of the patient. However, in the X-ray photography apparatus of the present invention, the X-ray image equivalent to that obtained by the intraoral radiography can be obtained using the X-ray detector disposed outside of the mouth of the patient without disposing the X-ray film in the mouth. Additionally, because the X-ray irradiation direction can be changed with respect to the axial direction of the body axis of the patient, the row of the teeth in the photographic region of pseudo intraoral radiography can be irradiated with the X-ray at a proper angle.

Preferably, the controller controls the irradiation direction changing part such that the irradiation direction is substantially orthogonal to the tooth being a part of row of the teeth included in the pseudo intraoral radiography region.

The X-ray is incident to the target tooth at a right angle, so that the image can be obtained in faithful accordance with the shape of the tooth with little or no distortion.

Preferably, the irradiation direction changing part includes: a first elevating mechanism that elevates an X-ray shielding member in parallel with the axial direction of the turning axis, the X-ray shielding member being mounted in front of the X-ray generator and forming an aperture through which the X-ray passes; and a second elevating mechanism that elevates the X-ray detector in the axial direction of the turning axis in conjunction with the elevating action of the X-ray shielding member, the elevating action of the X-ray shielding member being performed by the first elevating mechanism, and the controller controls the first elevating mechanism to change the irradiation direction.

By driving the first elevating mechanism and the second elevating mechanism, the X-ray irradiation direction can be changed without placing a burden on a test subject (or the patient).

Preferably, the irradiation direction changing part includes: a third elevating mechanism that elevates the support in parallel with the axial direction of the turning axis, and the controller controls the third elevating mechanism to change the height position of the X-ray generator that emits the X-ray.

By driving the third elevating mechanism, a target tooth can be irradiated with the X-ray at a proper height without placing a burden on the test subject.

Preferably, the X-ray photography apparatus of the present invention further includes a mode setter that selects one of a pseudo intraoral radiography mode and a CT photography mode, a tomographic image of the pseudo intraoral radiography region being generated in the pseudo intraoral radiography mode, an X-ray CT image of the head of the patient being generated in the CT photography mode, wherein, when the mode setter selects the CT photography mode, the controller controls an X-ray shielding member mounted in front of the X-ray generator to form the X-ray emitted from the X-ray generator into an X-ray cone beam, irradiates the CT photography region with the X-ray cone beam, and controls the irradiation direction changing part such that the center of the X-ray cone beam is incident to the CT photography region in a direction substantially orthogonal to the axial direction of the body axis.

The pseudo intraoral radiography and the CT photography can be performed with the identical X-ray photography apparatus.

Preferably, when setting the CT photography mode, the mode setter sets one of a first CT photography mode and a second CT photography mode, a region of both upper jaw and lower jaw to be set to a target region of CT photography in the first CT photography mode, a region of one of the upper jaw and the lower jaw to be set to the target region of the CT photography in the second CT photography mode, and the controller controls the irradiation direction changing part such that the center axis of the X-ray cone beam is incident to the CT photography region corresponding to one of the first CT photography mode and the second CT photography mode in the direction substantially orthogonal to the axial direction of the body axis.

The CT photography including the upper jaw and the lower jaw or the CT photography including the upper jaw or the lower jaw can be performed well by the setting of the photography mode.

Preferably, the controller controls the X-ray shielding member to change the spread of the X-ray cone beam from a point of view in the axial direction of the body axis, when setting the CT photography mode, the mode setter sets one of a local CT photography mode and a wide CT photography mode, only part of a region of the jaw being irradiated with the X-ray cone beam from the point of view in the axial direction of the body axis to be set to a CT photography target region in the local CT photography mode, a whole region of the jaw being irradiated with the X-ray cone beam from the point of view in the axial direction of the body axis to be set to the CT photography target region in the wide CT photography mode, and the controller controls the irradiation direction changing part such that the center of the X-ray cone beam is incident to the CT photography region corresponding to one of the local CT photography mode and the wide CT photography mode in the direction substantially orthogonal to the axial direction of the body axis, the local CT photography mode and the wide CT photography mode being set by the mode setter.

The local CT photography or the wide CT photography can be performed well by the setting of the photography mode.

Preferably, the mode setter sets a panoramic photography mode in which panoramic photography of a jaw is performed, and when the mode setter sets the panoramic photography mode, the controller controls the X-ray shielding member mounted in front of the X-ray generator to form the X-ray emitted from the X-ray generator into an X-ray slit beam, and controls the irradiation direction changing part such that the center of the X-ray slit beam is oriented upwardly with respect to the direction substantially orthogonal to the axial direction of the body axis.

Accordingly, the panoramic photography can properly be performed.

Preferably, the X-ray photography apparatus of the present invention further includes a mode setter that sets one of a pseudo intraoral radiography mode and a panoramic photography mode, the tomographic image of the pseudo intraoral radiography region being generated in the pseudo intraoral radiography mode, the panoramic photography of a jaw being performed in the panoramic photography mode, wherein when the mode setter sets the panoramic photography mode, the controller controls the X-ray shielding member mounted in front of the X-ray generator to form the X-ray emitted from the X-ray generator into an X-ray slit beam, and controls the irradiation direction changing part such that the center of the X-ray slit beam is oriented upwardly with respect to the direction substantially orthogonal to the axial direction of the body axis of the patient.

The pseudo intraoral radiography or the panoramic photography can be performed well by the setting of the photography mode.

Preferably, the controller controls the irradiation direction changing part such that the irradiation direction intersects the tooth being a part of the row of teeth included in the pseudo intraoral radiography region at a predetermined angle or an angle designated by an operator.

Preferably, the controller controls the irradiation direction changing part such that the irradiation direction is substantially orthogonal to the tooth being the part of the row of teeth included in the pseudo intraoral radiography region, or such that the irradiation direction is substantially orthogonal to the line that bisects the angle formed by the tooth axis of the tooth being the part of the row of teeth and the detection surface of the X-ray detector.

Therefore, an object of the present invention is to provide the technology for acquiring a good tomographic image equivalent to the X-ray image obtained by the intraoral radiography.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
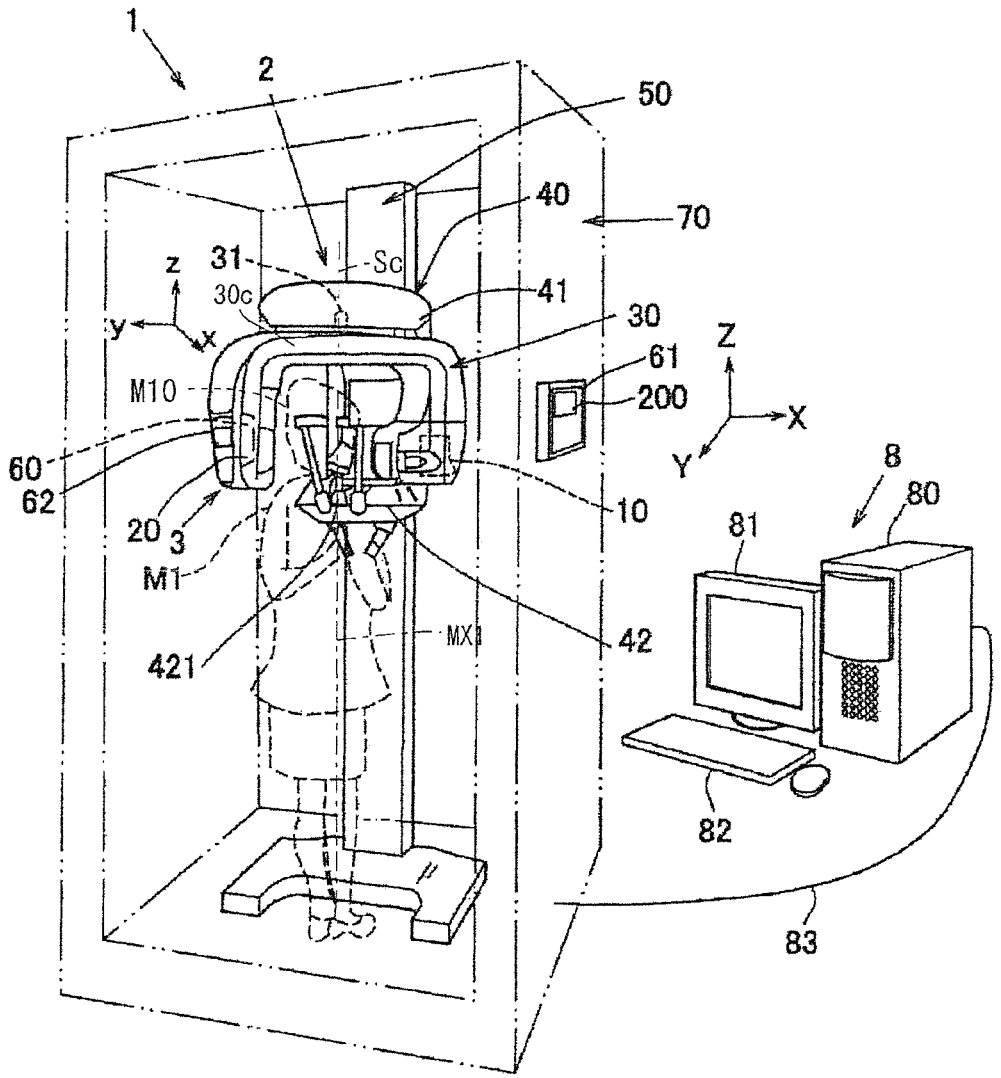
FIG. 1 is a schematic perspective view of an X-ray photography apparatus according to a preferred embodiment of the present invention.

Hereinafter, preferred embodiments of the present invention will be described with reference to the accompanying drawings. In the drawings, for the sake of convenience, occasionally, the size or the number of pieces of each component is indicated while magnified or simplified as occasion demands.

1. Preferred Embodiment

Figure 2:
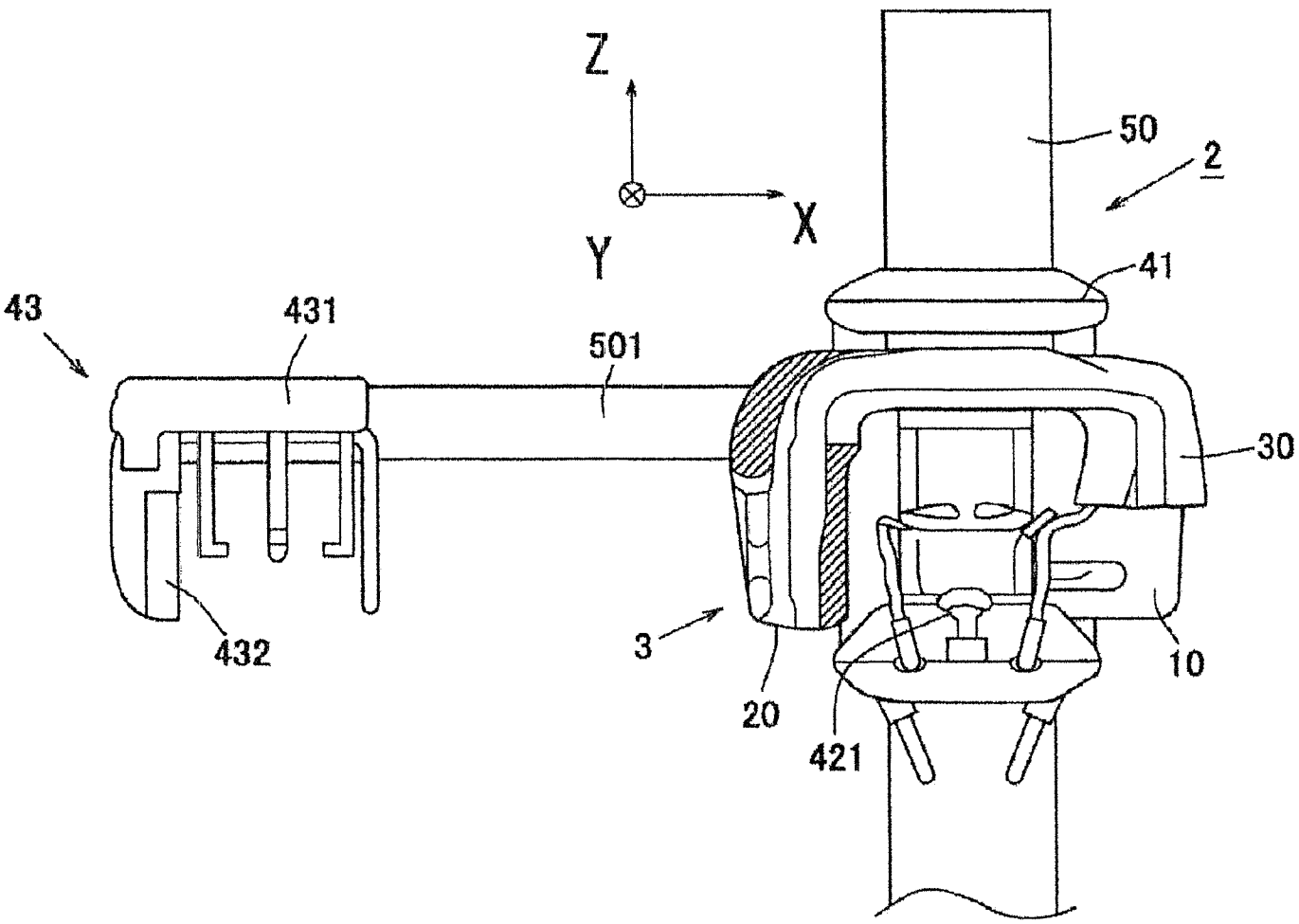
FIG. 2 is a partial front view of the X-ray photography apparatus on which a cephalostat is mounted.
Figure 3:
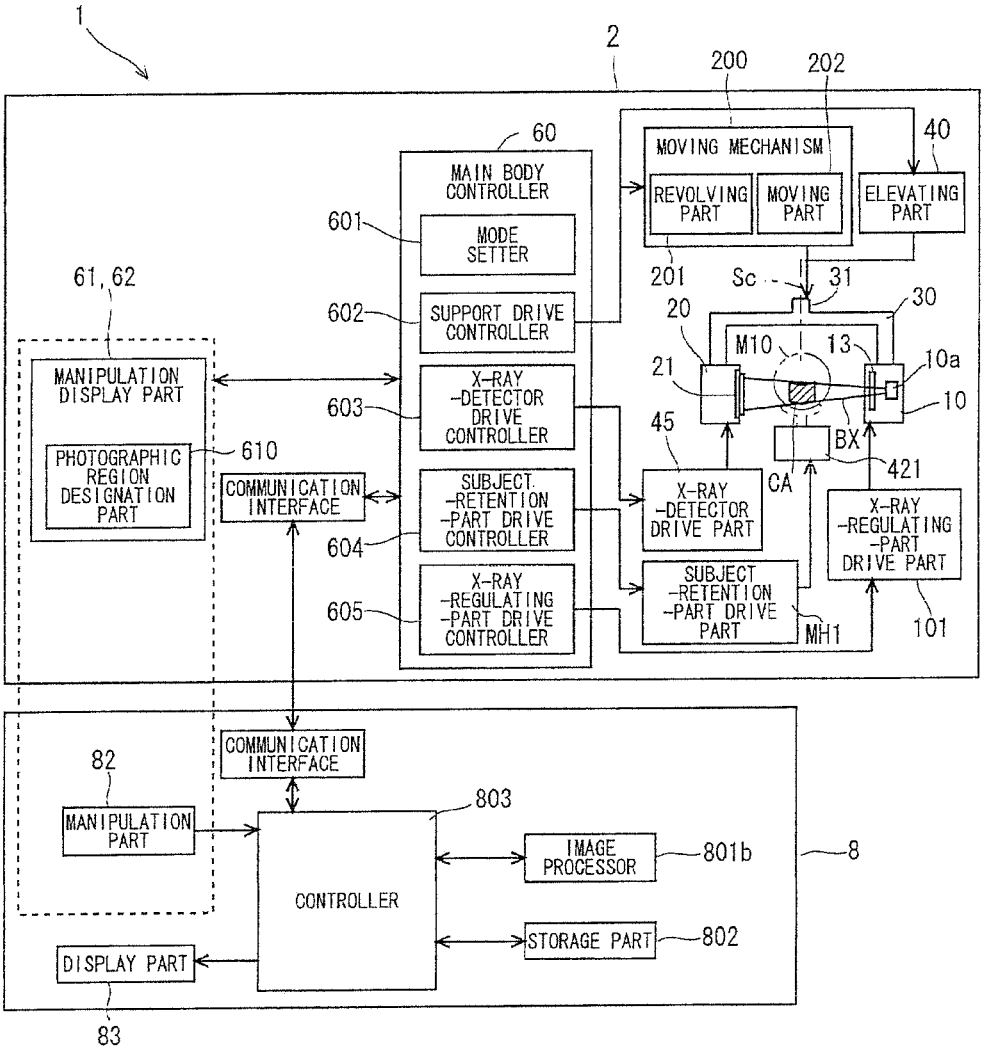
FIG. 3 is a block diagram of a configuration of the X-ray photography apparatus of the present invention.

FIG. 1 is a schematic perspective view of an X-ray photography apparatus 1 according to a preferred embodiment of the present invention. FIG. 2 is a partial front view of the X-ray photography apparatus 1 on which a cephalostat 43 is mounted. FIG. 3 is a block diagram of the configuration of the X-ray photography apparatus 1.

The X-ray photography apparatus 1 is substantially comprised of manipulation display parts 61 and 62, a main body 2, and an image processing device 8. The manipulation display parts 61 and 62 act as display element while setting a photographic region CA. The main body 2 collects X-ray projection data (frame data) by performing X-ray photography to the photographic region CA set through the manipulation display part 61. The image processing device 8 generates various images by processing the projection data collected by the main body 2.

The main body controller 60 of the main body 2 and a controller 803 and an image processor 801b (see FIG. 3) of the image processing device 8 perform the X-ray photography according to a program IMP (not illustrated) of the X-ray photography.

Desirably, the main body 2 is accommodated in a hollow, vertically long, cuboid-shape X-ray protective chamber 70 at a site of the X-ray photography. The main body 2, the manipulation display part 61 mounted on a wall surface of the X-ray protective chamber 70, and the image processing device 8 disposed outside the X-ray protective chamber 70 are connected to one another by a connection cable 83.

The main body 2 includes an X-ray generation part 10 and an X-ray detection part 20. The X-ray generation part 10 emits an X-ray beam BX (such as an X-ray cone beam BX1 and an X-ray slit beam to be described later) including a bundle of X-rays toward a subject M1. The X-ray detection part 20 detects the X-ray beam, which is transmitted through the subject M1 after emitted from the X-ray generation part 10. The main body 2 also includes a turning arm 30 serving as the support supporting the X-ray generation part 10 and the X-ray detection part 20, a vertically extending pillar 50, an elevating part 40 that can vertically be elevated with respect to the pillar 50 while suspending the turning arm 30, and a main body controller 60. The X-ray generation part 10, the X-ray detection part 20, and an X-ray beam forming mechanism 13 of the X-ray generation part 10 disposed on a side of the X-ray detection part 20 constitute a photographic mechanism 3.

The X-ray generation part 10 and the X-ray detection part 20 are suspended from and fixed to both end portions of a turning part 30c of the turning arm 30, respectively. The X-ray generation part 10 and the X-ray detection part 20 are supported so as to be opposed to each other. The turning arm 30 is suspended from the elevating part 40 with a vertically extending turning shaft 31 interposed therebetween.

The turning arm 30 has a substantially inverted U-shape when viewed from a the front side. The turning arm 30 turns about the turning shaft 31 serving as a turning center Sc provided in the upper end portion of the turning part 30c. In the preferred embodiment, the elevating part 40 includes an upper frame 41 that extends frontward from the upper portion of the elevating part 40 when viewed from the front side.

The turning arm 30 of the preferred embodiment is formed in a U-shape. Alternatively, the turning arm 30 may be formed into different shapes. For example, an annular member that is rotatably fitted in the outer circumferential portion of a columnar-shaped member fixed above the subject M1 with a ball bearing interposed therebetween and the like may be used instead of the turning arm 30. In this case, the X-ray generation part 10 and the X-ray detection part 20 are attached to the annular member so as to be opposed to each other. The annular member rotates along the outer circumferential portion of the columnar-shaped member, which allows the X-ray generation part 10 and the X-ray detection part 20 to rotate about the head M10 of the subject M1 with the head M10 interposed therebetween.

Hereinafter, the direction parallel to the axial direction of the turning shaft 31 (in the preferred embodiment, a vertical direction) is referred to as a "Z-axis direction", the direction intersecting the Z-axis direction is referred to as an "X-axis direction", and the direction intersecting the X-axis direction and the Z-axis direction is referred to as a "Y-axis direction". The X-axis direction and the Y-axis direction may arbitrarily be defined. However, in the preferred embodiment, when a test person serving as the subject M1 is positioned in the X-ray photography apparatus 1 to directly face the pillar 50, the side-to-side direction of the test person is defined as the X-axis direction, and the front-back direction of the test person is defined as the Y-axis direction. In the preferred embodiment, it is assumed that the X-axis direction, the Y-axis direction, and the Z-axis direction are orthogonal to one another.

Hereinafter, occasionally the Z-axis direction is referred to as the vertical direction, and the direction on a plane defined by a two-dimensional direction of the X-axis direction and Y-axis direction is referred to as a horizontal direction. Occasionally, the "Z-axis direction" is referred to as a "Z-direction", the "X-axis direction" is referred to as an "X-direction", and the "Y-axis direction" is referred to as a "Y-direction".

On the other hand, as to the three-dimensional coordinates on the turning arm 30, the direction in which the X-ray generation part 10 and the X-ray detection part 20 are opposed to each other is referred to as a "y-axis direction", the horizontal direction orthogonal to the y-axis direction is referred to as an "x-axis direction" and the vertical direction orthogonal to the x-axis direction and y-axis direction is referred to as a "z-axis direction".

Hereinafter, occasionally, the "z-axis direction" is referred to as a "z-direction", the "x-axis direction" is referred to as an "x-direction", and the "y-axis direction" is referred to as a "y-direction".

In the preferred embodiment and subsequent preferred embodiments, the z-axis direction and the Z-axis direction are parallel to each other. The turning arm 30 of the preferred embodiment turns about the vertically extending turning shaft 31 as a rotational axis (the turning axis). Accordingly, the xyz orthogonal coordinate system rotates about the Z-axis (=the z-axis) with respect to the XYZ orthogonal coordinate system.

In the preferred embodiment, as indicated in FIG. 1, when the test person directly faces the pillar 50, the right-hand direction is referred to as a (+X)-direction, the back-side direction is referred to as a (+Y)-direction, and the upwardly vertical direction is referred to as a (+Z)-direction. When the X-ray generation part 10 and the X-ray detection part 20 are viewed from above in plan, the direction from the X-ray generation part 10 toward the X-ray detection part 20 is referred to as a +y-direction, the left-hand direction from the −y-side toward the +y-direction is referred to as a +x-direction, and the upwardly vertical direction is referred to as a +z-direction.

The elevating part 40 includes the upper frame 41 (a first support retention part) and a lower frame 42 (*collectively referred to as a "frame"*), and engages the vertically-standing pillar 50. The turning shaft 31 is attached to the upper frame 41 that acts as a retention part for the turning arm 30. The elevating part 40 moves vertically along the pillar 50, whereby the turning arm 30 serving as the support moves up and down.

As to the structure that turns the turning arm 30, the turning arm 30 may be provided so as to be turnable with respect to the turning shaft 31 attached to the upper frame 41 so as to be non-turnable, and the turning arm 30 may turn with respect to the turning shaft 31. Alternatively, the turning arm 30 may be fixed so as to be non-turnable with respect to the turning shaft 31 provided to the upper frame 41 so as to be turnable, and the turning arm 30 may turn by turning the turning shaft 31.

In the structure that turns the turning arm 30, the torque of a turning motor (a support turning drive part) can act on the turning arm 30 through a power transmission mechanism (not illustrated) such as a belt and a pulley. For example, the turning motor is fixed to the inside of the turning arm 30, and an annular belt is entrained about the pulley fixed to the rotational shaft of the turning motor and the turning shaft 31 such that the torque of the turning motor acts on the turning arm 30. In this case, a bearing member such as a bearing may be interposed between the turning shaft 31 and the turning arm 30.

Alternatively, a turning motor that turns the turning arm 30 about the turning shaft 31 may be provided in the upper frame 41, and the transmission mechanism (not illustrated), which includes a belt, a pulley, and a rotational shaft and passes through the turning shaft 31, may transmit the torque of the turning motor to the turning arm 30 to turn the turning arm 30.

In the structure in which the turning arm 30 is fixed so as to be non-turnable, the turning arm 30 may be unturnably fixed to the turning shaft 31 turnable with respect to the upper frame 41, and the turning arm 30 may turn by turning the turning shaft 31 as a matter of course. In this structure, the turning motor is fixed to the inside of the upper frame 41, and the torque of the turning motor can act on the rotation of the turning shaft 31 using the transmission mechanism (not illustrated) such as a roller. In this case, a bearing member such as a ball bearing may be interposed between the turning shaft 31 and the upper frame 41.

In the preferred embodiment, the turning shaft 31 is configured to extend vertically. Alternatively, it is also conceivable that the turning shaft 31 is obliquely disposed at any angle with respect to the vertical direction.

The bearing (not illustrated) is interposed between the turning shaft 31 and the turning arm 30. Therefore, the turning arm 30 can rotate smoothly with respect to the turning shaft 31. The turning shaft 31, the transmission mechanism including the bearing, the belt, the pulley, and the rotational shaft, and the turning motor are an example of a revolving part 201 (see FIG. 3) that turns the turning arm 30. In other words, the revolving part 201 relatively turns the turning arm 30 (the support) about the turning shaft 31 with respect to the head M10 of the subject (the test person) M1. Therefore, the revolving part 201 relatively turns an X-ray generator 10a and an X-ray detector 21 about the head M10 of the subject M1.

At this point, it is considered that the subject includes a portion corresponding to the photographic region, an individual (the test person in the above case) including the photographic region, and part (the head in the above case) of the photographic region of the individual.

In the preferred embodiment, the turning arm 30 turns with respect to the turning shaft 31 that does not rotate with respect to the upper frame 41. However, as described above, it is also conceivable that the turning shaft 31 fixed to the turning arm 30 is turned with respect to upper frame 41 to turn the turning arm 30. In this case, the bearing that rotatably supports the turning shaft 31 is formed in the upper frame 41.

The main body 2 includes a moving part 202 that relatively moves the turning arm 30 in the direction (the X-direction, the Y-direction, or the direction having components of the X-direction and the Y-direction) perpendicular to the turning shaft with respect to the head M10 of the subject M1. The moving part 202 can be constructed by an XY table (not illustrated), which is fixed to the upper frame 41 or the turning arm 30. The XY table includes a table member that moves in the X-axis direction, a table member that moves in the Y-axis direction, and a motor that moves the table members in the X-axis direction and the Y-axis direction. In the case that the XY table is fixed to the upper frame 41, the XY table is fixed to the upper end portion of the turning shaft 31. In this case, by driving the XY table, the turning arm 30 moves in the direction perpendicular to the turning shaft 31 together with the turning shaft 31. In the case that the XY table is fixed on the turning arm 30, the XY table is fixed to the lower end portion of the turning shaft 31. In this case, only the turning arm 30 moves in the direction perpendicular to the turning shaft 31.

Using the XY table, the turning center of the X-ray generator 10a and the X-ray detector 21 can be fixed to a place different from the turning shaft 31 serving as the mechanical turning axis.

For example, in CT photography, the center of the photographic region CA is set on the line connecting the centers of the X-ray generator 10a and the X-ray detector 21 when the X-ray generator 10a, the X-ray detector 21, and the photographic region CA is looked down in the Z-direction. The axis center of the turning shaft 31 is set to a place different from the photographic region CA on the line connecting the centers of the X-ray generator 10a and the X-ray detector 21. Under this geometric condition, the turning arm 30 is turned about the turning shaft 31, and the XY table turns the turning shaft 31 about the center of the photographic region CA by an angle equal to the turning angle of the turning arm 30. In this manner, the CT photography can also be performed by irradiating the photographic region CA with the X-ray cone beam while the X-ray generator 10a and the X-ray detector 21 turn about the center of the photographic region CA.

Japanese Patent Application Laid-Open No. 2007-29168 and International Patent Publication No. 2009/063974, which have been filed by the applicant of the present application, disclose the configuration implementing the above CT photography, and can also be appropriately applied to the present embodiment.

In the preferred embodiment of the present application, a moving mechanism 200 (*i.e., a driver*) including the revolving part 201 and the moving part 202 can relatively move the turning arm 30 with respect to the head M10 of the subject M1. However, the moving mechanism 200 is not limited to the above configuration. For example, the main body 2 may be configured such that the moving mechanism 200 rotates the subject M1 about a predetermined rotational axis, or such that the moving mechanism 200 moves the subject M1 in the direction perpendicular to the rotational axis.

A subject retention part 421 is provided in the lower frame 42. The subject retention part 421 includes a head holder that fixes the head M10 of the subject M1 of a human body from the right and left sides and a chin rest that fixes the chin of the patient.

The turning arm 30 is disposed at a proper position by elevating the elevating part 40 according to the height of the subject M1. At this point, the subject M1 is fixed to the subject retention part 421. In the example indicated in FIG. 1, the subject retention part 421 retains the subject M1 such that the body axis MX1 of the subject M1 is substantially aligned with the axial direction of the turning shaft 31. As used herein, the "body axis" means a symmetrical axis, which is set in the case that the human body is considered to be substantially symmetrical when viewed from the front side.

A support driving controller 602 (see FIG. 3) of the main body controller 60 controls the operations of the elevating part 40 and the moving mechanism 200.

The main body controller 60 is a controller that controls the operation of each component of the main body 2. For example, the main body controller 60 acts as an X-ray regulating controller and a drive controller. As indicated in FIG. 1, the main body controller 60 is disposed inside the X-ray detection part 20.

A manipulation display part 62 is attached to the outside of the main body controller 60, namely, on the +y side of the X-ray detection part 20. The manipulation display part 62 includes buttons that are used to input various designations or a touch panel that displays various pieces of information.

The manipulation display part 61 is attached to the outside of the wall of the X-ray protective chamber 70 that accommodates the main body 2 therein. The manipulation display part 61 is connected to the main body controller 60, and includes buttons that are used to input various designations and a touch panel that displays various pieces of information.

An operator (for example, a practitioner) may manipulate the main body 2 using the manipulation display part 62, or manipulate the main body 2 using the manipulation display part 61. The manipulation display part 62 may differ from the manipulation display part 61 in a manipulation content or a display content. Part or whole of the manipulation content or display content may be common to the manipulation display part 62 and the manipulation display part 61.

In the case that the X-ray protective chamber 70 is eliminated, the manipulation display part 61 may be eliminated as well. One of the manipulation display part 62 and the manipulation display part 61 may be eliminated. Although the display and manipulation performed by the manipulation display part 61 are described below, the display and manipulation performed by the manipulation display part 61 may be replaced with the display and manipulation performed by the manipulation display part 62.

The manipulation display part 61 is also used, for example, to designate the position of the photographic region of a biological organ. There are various modes in the X-ray photography, and the mode may be selected through the manipulation of the manipulation display part 61.

The image processing device 8 includes an image processing main body 80, a display part 81 including a display device such as a liquid crystal monitor, and a manipulation part 82 including a keyboard and a mouse. The operator (the practitioner and the like) can input various commands to the image processing device 8 through the manipulation part 82. The display part 81 may include the touch panel. In this case, the display part 81 may include part of or whole of the functions of the manipulation part 82.

For example, the image processing main body 80 includes a computer or a workstation. The image processing main body 80 transmits and receives various pieces of data to and from the main body 2 through the connection cable 83 serving as the communication cable. Alternatively, the main body 2 and the image processing main body 80 may wirelessly conduct data communication with each other.

For example, the image processing device 8 processes the projection data acquired by the main body 2, and reconstructs three-dimensional data (volume data) expressed in the voxel form. For example, a specific cutting plane can be set to the three-dimensional data, and a tomographic image is reconstructed in the specific cutting plane.

It is also considered that the X-ray photography apparatus 1 is used as an apparatus that collects only the frame data by the X-ray photography. In such cases, the image processing device 8 may be eliminated.

As indicated in FIG. 2, the cephalostat 43 may be attached to the X-ray photography apparatus 1. For example, the cephalostat 43 is attached to an arm 501 that extends horizontally from the middle of the elevating part 40. The cephalostat 43 includes a fixture 431 that fixes the head M10 to a given position and an X-ray detector 432 for cephalic photography. For example, a cephalostat disclosed in Japanese Patent Application Laid-Open No. 2003-245277 or a cephalostat similar thereto can be used as the cephalostat 43.

<Irradiation Direction Changing Part>

Figure 4:
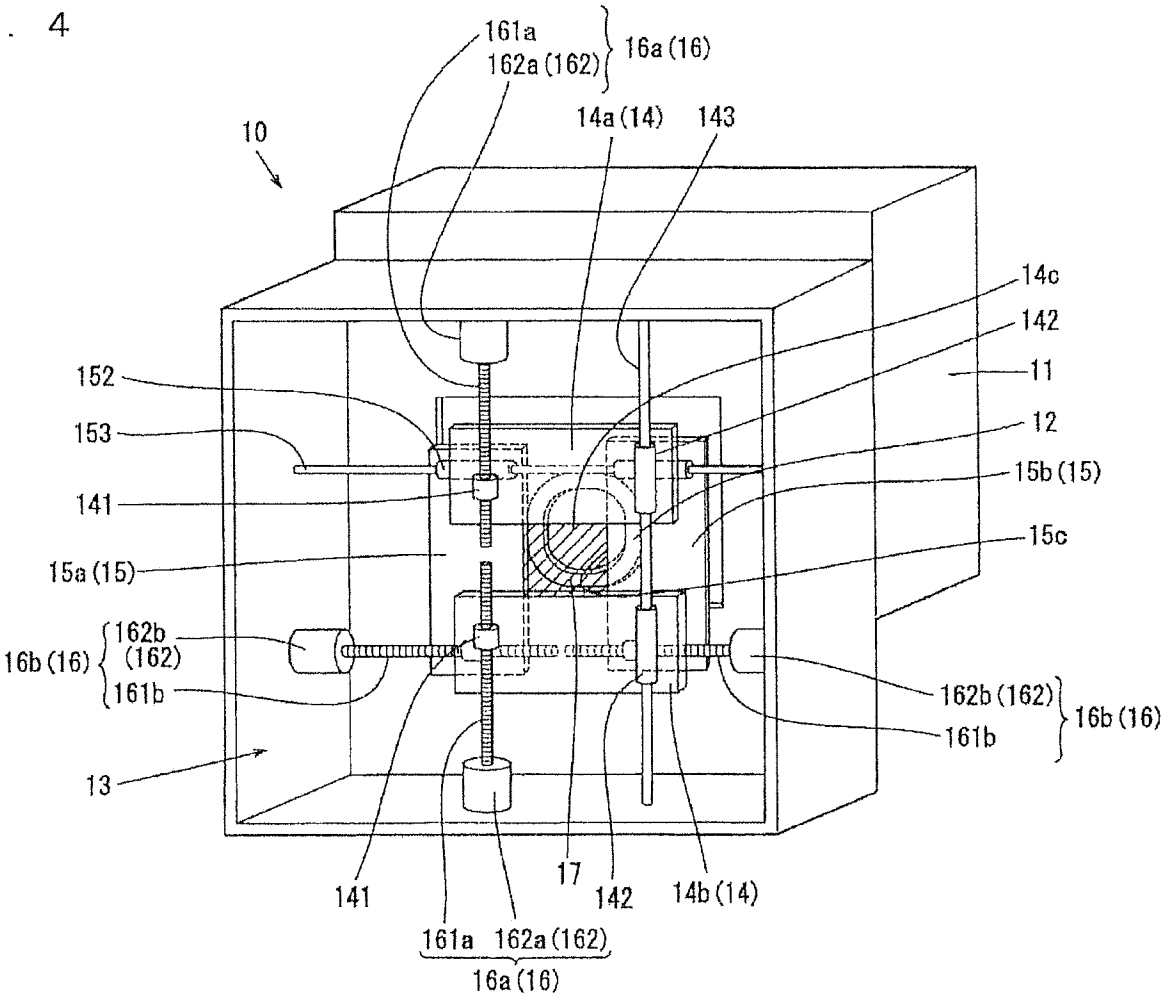
FIG. 4 is a schematic perspective view of a beam forming mechanism (an X-ray regulating part) of the X-ray photography apparatus of the present invention.
Figure 5:
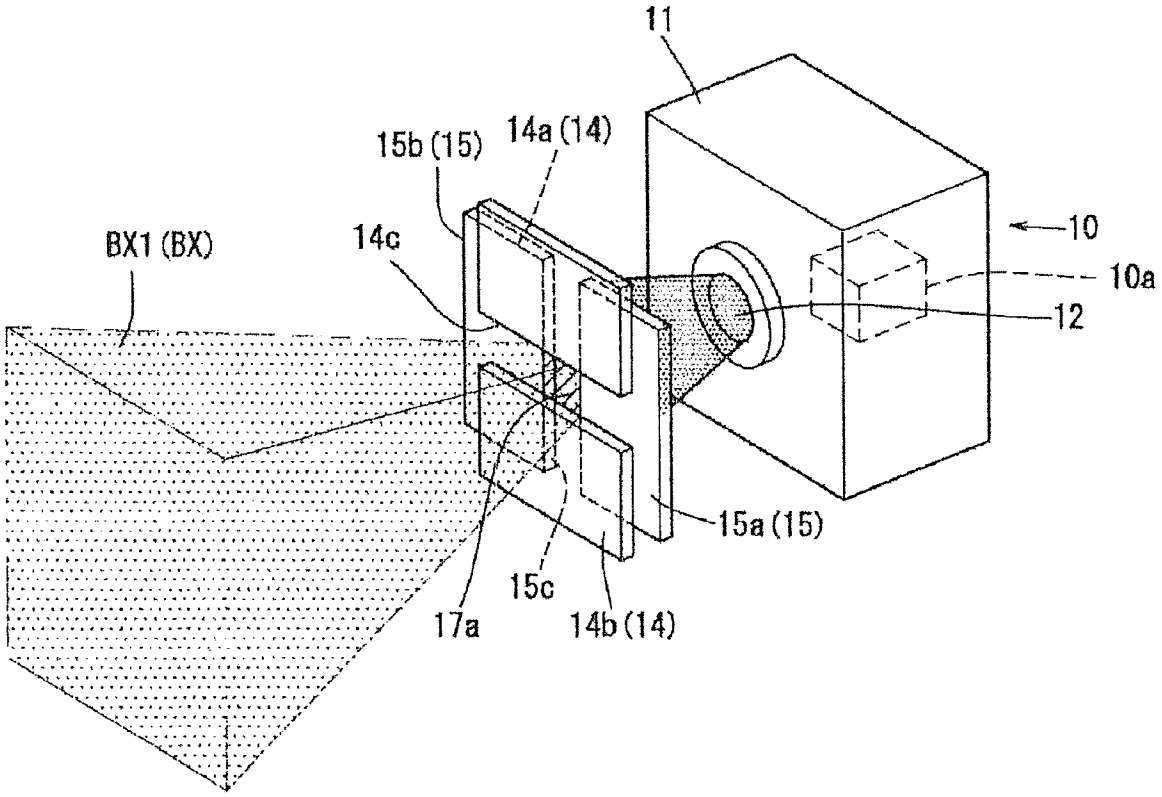
FIG. 5 is a schematic perspective view of an X-ray generation part of the X-ray photography apparatus that emits an X-ray cone beam in which an irradiation range is regulated.
Figure 6:
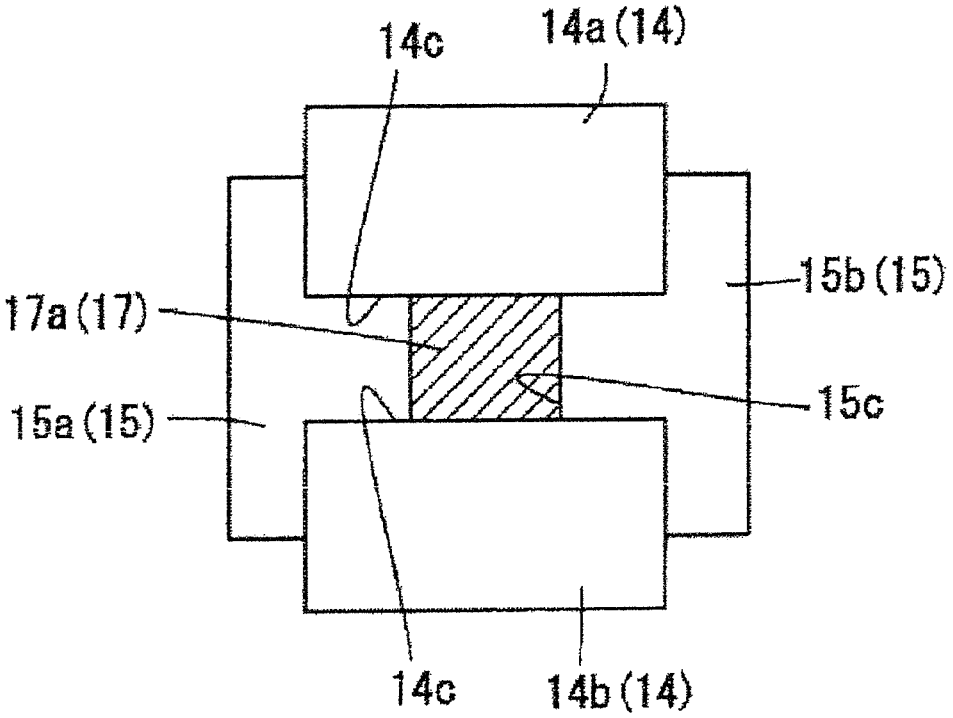
FIGS. 6 and 7 are explanatory views of position adjustments of vertically-shielding plates and horizontally-shielding plates.
Figure 7:
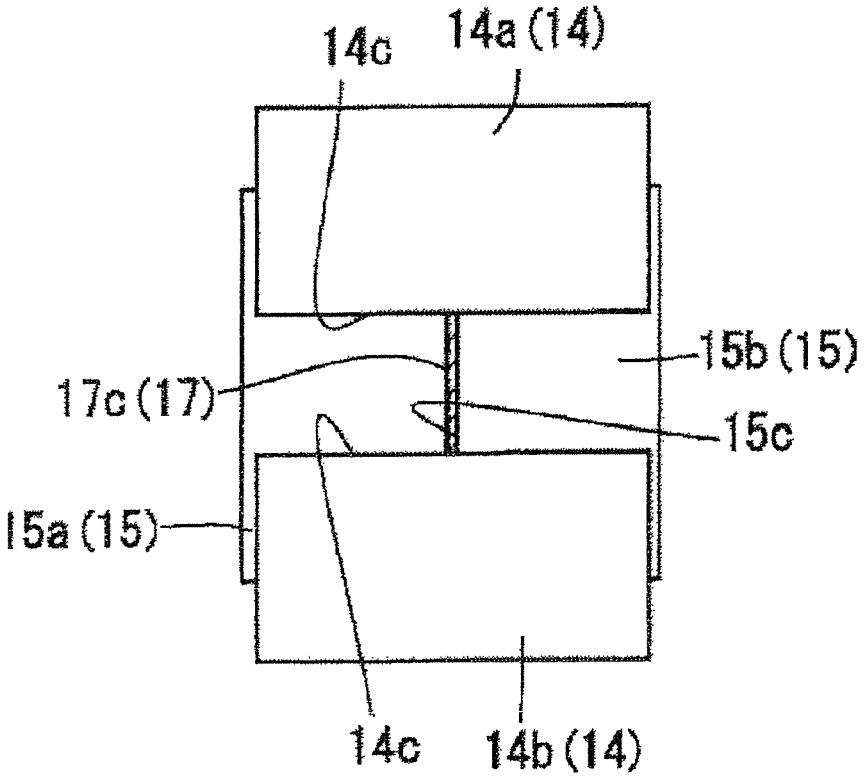
Figure 8:
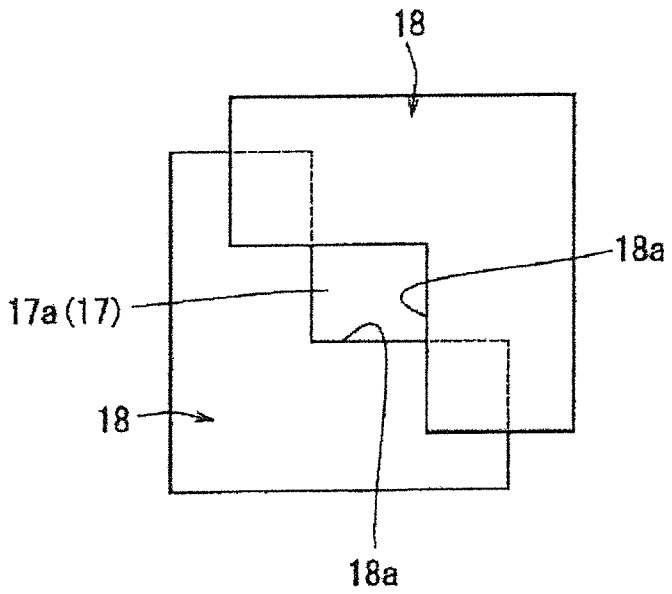
FIG. 8 is an explanatory view of the position adjustments of two L-shape shielding plates.
Figure 9:
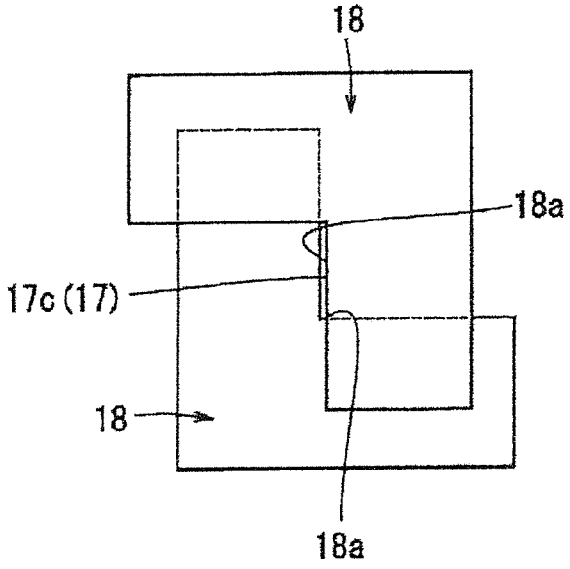
FIG. 9 is an explanatory view of the position adjustments of the two L-shape shielding plates.

FIG. 4 is a schematic perspective view of the X-ray beam forming mechanism 13 (the X-ray regulating part). FIG. 5 is a schematic perspective view of the X-ray generation part 10 that emits the X-ray cone beam BX1 in which an irradiation range is regulated. FIGS. 6 and 7 are explanatory views of position adjustments of the vertically-shielding plates 14 and the horizontally-shielding plates 15. FIGS. 8 and 9 are explanatory views of the position adjustments of two L-shape shielding plates 18 and 18.

In the turning arm 30, the X-ray generation part 10 that is disposed so as to be opposed to the X-ray detection part 20 includes the X-ray generator 10a including an X-ray tube accommodated in a housing 11 (see FIG. 3). An outgoing port 12 that permits transmission of the X-ray generated by the X-ray tube is provided in the front surface of the housing 11. The X-ray beam forming mechanism 13 that acts as the X-ray regulating part is disposed in front of the outgoing port 12. In other words, the X-ray beam forming mechanism 13 is disposed on the front side of the outgoing port 12 in FIG. 4 and the side of the −y-direction in the Y-axis direction with respect to the X-ray generation part 10

The X-ray beam forming mechanism 13 includes vertically-shielding plates 14 (*i.e., a shield*) that move in the vertical direction (the z-axis direction) to shield the X-ray irradiation direction, a horizontally-shielding plates 15 that move in the horizontal direction (the x-axis direction) to shield the X-ray irradiation direction, and a shielding-plate moving mechanism 16 that moves the vertically-shielding plates 14 and the horizontally-shielding plates 15. The shielding-plate moving mechanism 16 is an example of an X-ray-regulating-part drive part 101 indicated in FIG. 3. An X-ray-regulating-part drive controller of the main body controller 60 controls the drive of the X-ray beam forming mechanism 13 (specifically, the shielding-plate moving mechanism 16). The vertically-shielding plates 14 and the horizontally-shielding plates 15 are examples of the X-ray shielding member that is used to regulate a shield amount of the X-ray generated from the X-ray generator 10a in a limited manner.

The vertically-shielding plates 14 include a horizontally-long upper vertically-shielding plate 14a and a horizontally-long lower vertically-shielding plate 14b, which are disposed above and below (the +z side and the −z side) the outgoing port 12 when viewed from the front side. The horizontally-shielding plates 15 include a longitudinally long left horizontally-shielding plate 15a and a longitudinally long right horizontally-shielding plate 15b, which are disposed on the right and left sides (the −x side and the +x side) of the outgoing port 12 when viewed from the front side. In the example illustrated in FIG. 4, the horizontally-shielding plates 15 are disposed on the side (the −y side) of the housing 11 of the vertically-shielding plates 14. Alternatively, the vertically-shielding plates 14 may be disposed on the side of the housing 11 of the horizontally-shielding plates 15.

The shielding-plate moving mechanism 16 includes a pair of shielding-plate vertically-moving mechanisms 16a that move the upper vertically-shielding plate 14a and the lower vertically-shielding plate 14b in the vertical direction and a pair of shielding-plate horizontally-moving mechanisms 16b that move the left horizontally-shielding plate 15a and the right horizontally-shielding plate 15b in the horizontal direction.

The shielding-plate vertically-moving mechanism 16a includes nut members 141 that are attached respectively to the upper vertically-shielding plate 14a and the lower vertically-shielding plate 14b, vertically-screw shafts 161a that extend vertically to engage the nut members 141, and position adjustment motors 162a (162) that normally or reversely rotate the screw shafts 161a. The screw shaft 161a is normally or reversely rotate by driving the position adjustment motor 162a, whereby the nut member 141 moves up and down along the vertical direction. Therefore, the upper vertically-shielding plate 14a and the lower vertically-shielding plate 14b move independently in the vertical direction. Under the control of the main body controller 60 (specifically, the X-ray-regulating-part drive controller 605), the shielding-plate vertically-moving mechanism 16a adjusts the vertical shielding amount of the X-ray beam emitted from the X-ray generator 10a using the upper vertically-shielding plate 14a and the lower vertically-shielding plate 14b.

The shielding-plate vertically-moving mechanism 16a is an example of the first elevating mechanism, which controls the irradiation direction (the direction in which a center line of an irradiation range extends) by adjusting the spreading (the irradiation range) of the X-ray beam related to the vertical direction, namely, the direction related to the axial direction of the turning shaft 31.

A regulating cylindrical body 142 is attached to each of the upper vertically-shielding plate 14a and the lower vertically-shielding plate 14b. A through-hole is made in the regulating cylindrical body 142 so as to vertically pierce the regulating cylindrical body 142. A vertically extending regulating shaft 143 is fitted in the regulating cylindrical body 142, and the vertical movement of the regulating cylindrical body 142 is regulated by the regulating shaft 143. Therefore, the upper vertically-shielding plate 14a and the lower vertically-shielding plate 14b move vertically with little or no inclination.

The shielding-plate horizontally-moving mechanism 16b includes nut members 161 that are attached respectively to the left horizontally-shielding plate 15a and the right horizontally-shielding plate 15b, horizontal screw shafts 161b that extend horizontally to engage the nut members 161, and position adjustment motors 162b (162) that normally or reversely rotate the screw shafts 161b. The screw shaft 161b is normally or reversely rotated by driving the position adjustment motor 162b, whereby the nut member 161 moves right and left in the horizontal direction. Therefore, the left horizontally-shielding plate 15a and the right horizontally-shielding plate 15b move independently in the horizontal direction. Under the control of the main body controller 60, the shielding-plate horizontally-moving mechanism 16b adjusts the horizontal shielding amount of the X-ray beam emitted from the X-ray generator 10a using the left horizontally-shielding plate 15a and the right horizontally-shielding plate 15b. The shielding-plate horizontally-moving mechanism 16b is an example of the horizontal-irradiation position controller, which controls the irradiation direction by adjusting the irradiation range of the X-ray beam related to the horizontal direction.

A regulating cylindrical body 152 is attached to each of the left horizontally-shielding plate 15a and the right horizontally-shielding plate 15b. A through-hole is made in the regulating cylindrical body 152 so as to pierce the regulating cylindrical body 152 in the horizontal direction. A regulating shaft 153 extending horizontally is fitted in the regulating cylindrical body 152, and the horizontal movement of the regulating cylindrical body 152 is regulated by the regulating shaft 153. Therefore, the left horizontally-shielding plate 15a and the right horizontally-shielding plate 15b move horizontally with little or no inclination.

In the preferred embodiment, the X-ray beam forming mechanism 13 includes the vertically-shielding plates 14, the horizontally-shielding plates 15, and the shielding-plate moving mechanism 16, and the X-ray beam forming mechanism 13 is disposed in front of the outgoing port 12 in the X-ray generation part 10. Therefore, the irradiation range of the X-ray generated by the X-ray generation part 10 is regulated by the shielding to form the X-ray cone beam BX1 that spreads in a truncated pyramid shape toward the X-ray detection part 20 (see FIG. 5).

Particularly, an interval between opposing edge portions 14c and 14c in the upper vertically-shielding plate 14a and the lower vertically-shielding plate 14b is adjusted by the shielding-plate vertically-moving mechanism 16a, and an interval between opposing edge portions 15c and 15c in the left horizontally-shielding plate 15a and the right horizontally-shielding plate 15b is adjusted by the shielding-plate horizontally-moving mechanism 16b. In order to form a desired-shape X-ray cone beam BX1, an opening 17 that has a quadrangular shape when viewed from the front side is formed in front of the X-ray generator 10a by the opposing edge portions 14c and 14c and the opposing edge portions 15c and 15c.

For example, as indicated in FIG. 6, the interval between the opposing edge portions 14c and 14c is widely adjusted, and the interval between the opposing edge portions 15c and 15c is widely adjusted, whereby the opening 17 becomes a relatively large square opening 17a for large irradiation field when viewed from the front side. The X-ray passing through the opening 17a for large irradiation field has a square section, and becomes the X-ray cone beam BX1 that spreads in the square truncated pyramid shape toward the X-ray detection part 20.

As indicated in FIG. 7, the interval between the opposing edge portions 14c and 14c is widely adjusted, and the interval between the opposing edge portions 15c and 15c is narrowly adjusted, whereby the opening 17 becomes a rectangular, panoramic-photography opening 17c that is vertically long when viewed from the front side. The X-ray passing through the panoramic-photography opening 17c becomes the X-ray slit beam that spreads in the longitudinally long truncated pyramid shape toward the X-ray detection part 20.

As indicated in FIGS. 8 and 9, the X-ray beam forming mechanism may be constructed by two L-shape shielding plates 18 and 18, which have an L-shape when viewed from the front side and are symmetrically disposed with respect to the center of the opening 17. In this case, the opening 17 is constructed by edge portions 18a and 18a constituting internal angle portions of the two L-shape shielding plates 18 and 18.

For example, the shielding-plate vertically-moving mechanism 16a and the shielding-plate horizontally-moving mechanism 16b are provided, and the L-shape shielding plates 18 and 18 are moved in the vertical direction and the horizontal direction, which allows the shape of the opening 17 to be adjusted.

For example, a vertically-moving mechanism similar to the shielding-plate vertically-moving mechanism 16a is provided on a base (not illustrated) that is displaced horizontally by a horizontally-moving mechanism similar to the shielding-plate horizontally-moving mechanism 16b, and the one L-shape shielding plate 18 is vertically displaced by the vertically-moving mechanism. Each L-shape shielding plate 18 can be moved in the vertical direction and the horizontal direction by the horizontally-moving mechanism, the base and the vertically-moving mechanism. For example, the X-ray cone beam BX1 can be formed by spreading the opening 17 as indicated in FIG. 8, and the X-ray slit beam can be formed by making the opening 17 slender as indicated in FIG. 9.

<Photography Mode Selection Screen>

Figure 10:
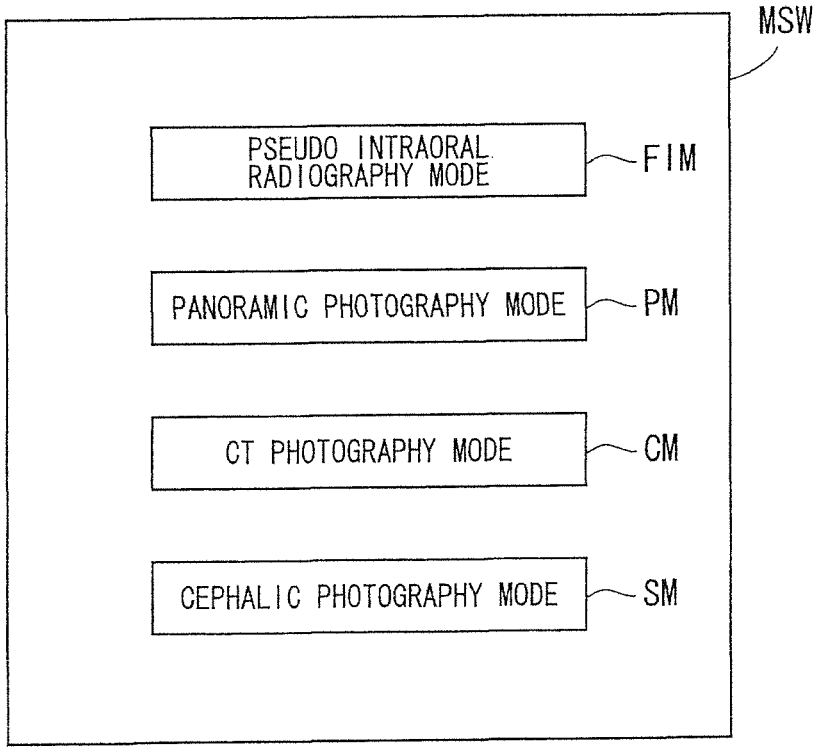
FIG. 10 is a view indicating a photography mode setting screen used to set a photography mode.

FIG. 10 is a view indicating a photography mode setting screen MSW used to set a photography mode. The photography mode setting screen MSW indicated in FIG. 10 includes a pseudo intraoral radiography mode button FIM, a panoramic photography mode button PM, a CT photography mode button CM, and a cephalic photography mode button SM. The pseudo intraoral radiography mode button FIM is used to select a pseudo intraoral radiography mode. The panoramic photography mode button is used to select a panoramic photography mode. The CT photography mode button CM is used to select a CT photography mode. The cephalic photography mode button is used to select a cephalic photography mode.

For example, the photography mode selection screen MSW is displayed on the manipulation display part 61 or the manipulation display part 62 before the photographing is performed after the X-ray photography apparatus 1 is started up. The operator selects the desired photography mode through the photography mode selection screen MSW. A mode setter 601 (see FIG. 3) of the main body controller 60 sets the photography mode of the main body controller 60 to the selected photography mode. Therefore, in the X-ray photography apparatus 1, a photographing condition (such as the position and the shape of the photographic region) can be set according to the X-ray photography of the set type.

The pseudo intraoral radiography mode is one in which the pseudo intraoral radiography is performed. In the pseudo intraoral radiography, the conventional intraoral radiography (the dental radiography) in which the partial region (for example, a few teeth) of the row of teeth is set to the photographing target is performed in the pseudo manner with the X-ray photography apparatus 1. At this point, the X-ray image obtained by the conventional intraoral radiography is a simple projection image, which is obtained by irradiating the partial region of the row of teeth with the X-ray in one direction while the conventional X-ray film is set in the oral cavity. On the other hand, in the pseudo intraoral radiography, the image equivalent to the simple projection image or the image with which the equivalent diagnosis can be made is generated by the tomographic image.

In the conventional intraoral radiography, the conventional X-ray film (or imaging plate and so on) put inside mouth oral cavity receives the X-ray passed through the target teeth or tooth, so the X-ray which passed through only the target teeth or tooth should be detected. In contrast, the pseudo intraoral radiography of the present invention is executed by way of extraoral radiograph, so the X-ray which passed through the hard tissue other than the target teeth or tooth is also detected. In the present invention, the projection images are processed into tomographic image in order to avoid image formation of the image data other than the target teeth or tooth as much as possible. In other words, the pseudo intraoral radiography of the present invention is a radiography which executes X-ray radiography of the imaging region equivalent to the imaging region of conventional intraoral radiography by extraoral radiography in the way of tomography.

More specifically, the X-ray cone beam BX1 in which the irradiation range is regulated so as to include the whole photographic region (a pseudo intraoral radiography region) is formed in the pseudo intraoral radiography. The photographic region is irradiated with the X-ray cone beam BX1 in plural directions (the directions within a predetermined range) to obtain the frame data. The image processing device 8 (the image processor 801b) performs the image processing on the obtained frame data to obtain the tomographic image of the target cross-sectional plane. In the image processing, for example, a shift-and-add method is applied to overlap the X-ray projection images expressed by the frame data, thereby reconstructing the tomographic image. Although a character of the reconstructed tomographic image in this manner differs strictly from that of the X-ray image obtained by the conventional intraoral radiography, the reconstructed tomographic image is extremely similar to the X-ray image obtained by the conventional intraoral radiography from the viewpoint of the image diagnosis.

As used herein, the "shift-and-add method" refers to a method, in which the tomographic image having any height is obtained by overlapping the projection images that are obtained by changing the X-ray irradiation direction. Specifically, the X-ray passing through the common position of the target cross-sectional plane is photographed at the different position in each piece of frame data by changing the X-ray irradiation direction. Therefore, the pieces of frame data are shifted and overlapped such that the different positions are matched with each other, which allows the target cross-sectional plane to be highlighted.

The method for generating the tomographic image is not limited to the shift-and-add method. For example, the tomographic image may be reconstructed by filter back projection used in the reconstruction of the CT image or similar back projection.

The tomographic images of plural types may be reconstructed by performing both of the shift-and-add method and the filter back projection or the similar back projection, and simultaneously or alternately displayed.

In the example described above, the pseudo intraoral radiography is performed while the whole photographic region (the pseudo intraoral radiography region) is irradiated with the X-ray cone beam BX1 in which the irradiation range is regulated. Alternatively, the horizontal width of the X-ray beam BX may be further narrowed to form the X-ray slit beam used in the panoramic photography, and the photographic region (the pseudo intraoral radiography region) may horizontally be scanned. In other words, the pseudo intraoral radiography may be performed by the X-ray photography similar to the panoramic photography that is restricted to a kind of a pseudo intraoral radiography region.

The panoramic photography mode is one in which the panoramic photography (panoramic X-ray photography) is performed. In the panoramic photography, the row of teeth is irradiated along a dental arch with the X-ray beam formed into the X-ray slit beam, thereby obtaining the frame data. The image processing device 8 (the image processor 801b) generates the one panoramic image (the panoramic X-ray image) by connecting end portions of the projection images expressed by the frame data (however, generation of an overlapping portion is not troublesome).

The CT photography mode is one in which the CT photography is performed. In the CT photography, the X-ray cone beam BX1 is formed in which the irradiation range is regulated so as to include the whole photographic region (the CT photographic region). The photographic region is irradiated with the X-ray cone beam BX1 in multiple directions (for example, the directions of at least 180 degrees) to obtain the frame data. The image processing device 8 (the image processor 801b) reconstructs the tomographic image of the specific cutting plane by applying the filter back projection method (FBP method) to the obtained frame data.

The cephalic photography mode is one in which the cephalic photography is performed. In the cephalic photography, as indicated in FIG. 2, the cephalostat 43 is mounted on the X-ray photography apparatus 1, and the head M10 of the test subject is irradiated with the X-ray slit beam formed for the purpose of the cephalic photography to obtain the frame data. A cephalic photography X-ray detector 432 is configured to be able to be displaced in the Y-direction. The shielding-plate moving mechanism 16 is actuated to scan the head M10 in the Y-direction with the X-ray slit beam, the cephalic photography X-ray detector 432 is displaced in synchronization with the scanning of the head M10, and the cephalic photography X-ray detector 432 acquires the frame data while always receiving the X-ray slit beam during the cephalic photography. The image processing device 8 (the image processor 801b) generates the projection image (a head X-ray standard image) of the entire head M10 by connecting the end portions of the projection images expressed by the obtained frame data (however, the generation of the overlapping portion is not troublesome).

<Photographic Region Setting Screen>

Figure 11:
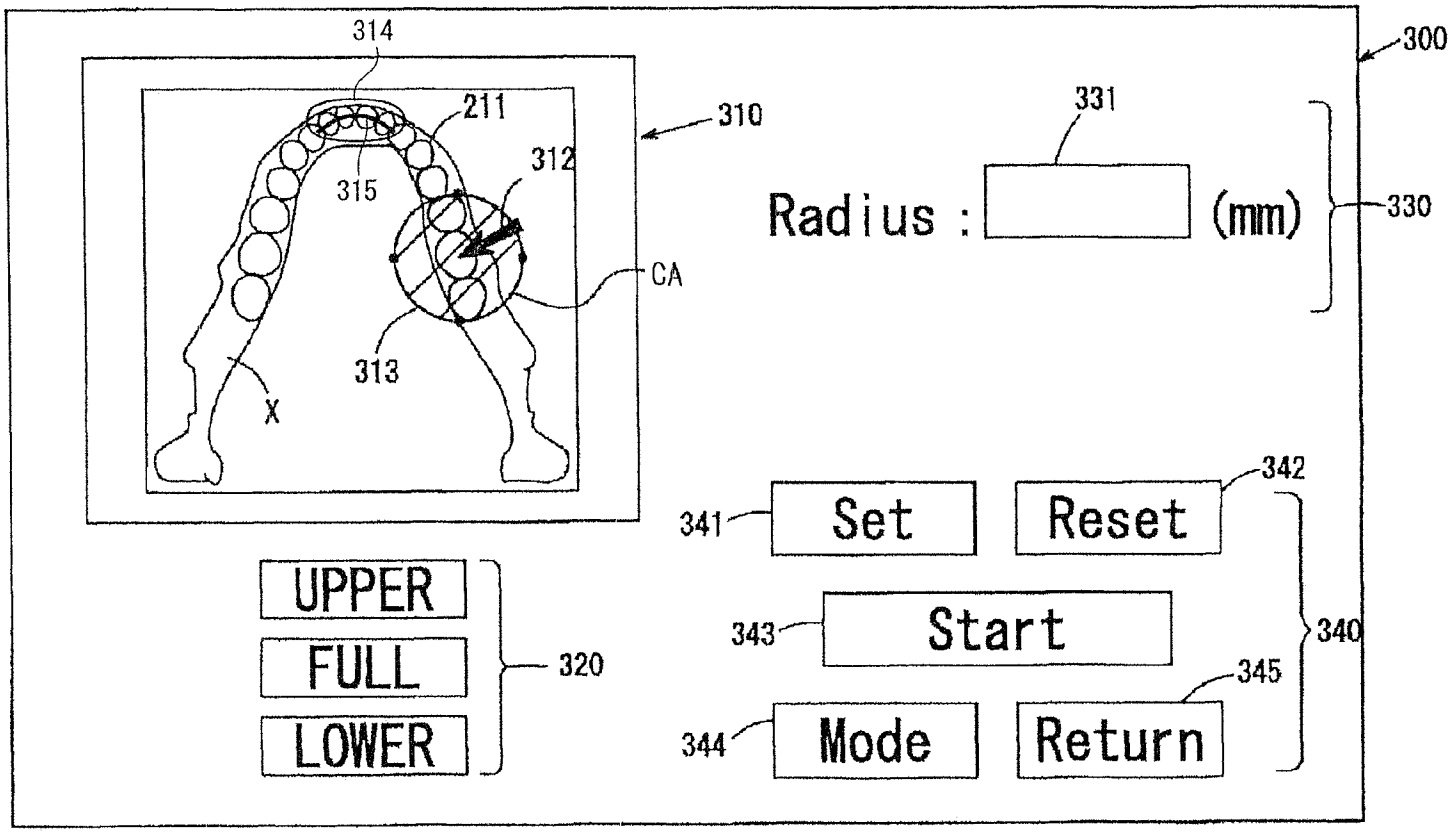
FIG. 11 is a view indicating a photographic region setting screen used to set a photographic region.

FIG. 11 is a view indicating a photographic region setting screen 300 used to set the photographic region CA. The photographic region setting screen 300 indicated in FIG. 11 includes an image display portion 310, an upper and lower jaw selection portion 320, a selection range setting portion 330, and a condition setting portion 340. The condition setting portion 340 includes a set button 341, a reset button 342, a start button 343, a mode button 344, and a return button 345.

A dental arch image 211, a designation cursor 312, and a true-circle-like photographic region line 313 are displayed in the image display portion 310 while superimposed on each other. The designation cursor 312 designates each point. The photographic region line 313 has a center designated by the designation cursor 312, and a radius designated by the selection range setting portion 330 to be described later. The dental arch image 211 is a schematic diagram in which a plan view of the row of teeth having a standard size is schematically drawn. Basically, the region surrounded by the photographic region line 313 is matched with a region that is irradiated with the X-ray of at least 180° by the one-time CT photography.

The upper and lower jaw selection portion 320 includes an UPPER button 321 for setting the photographic region CA to the upper jaw, a FULL button 322 for setting the photographic region CA to both upper jaw and lower jaw, and a LOWER button 323 for setting the photographic region CA to the lower jaw. For example, as to the CT photography, by the selection through the upper and lower jaw selection portion 320, the photography mode of the main body 2 is set to one of a CT photography mode (a first CT photography mode) in which the region extending across the upper jaw and the lower jaw is set to the target region of the CT photography and a CT photography mode (a second CT photography mode) in which one of the regions of the upper jaw and the lower jaw is set to the target region of the CT photography.

The condition setting portion 340 is constructed by the set button 341, the reset button 342, the start button 343, the mode button 344, and the return button 345. The set button 341 is manipulated to determine a designation content of the photographic region CA. The designation content of the photographic region CA is set through the image display portion 310, the upper and lower jaw selection portion 320, and the selection range setting portion 330. The reset button 342 is manipulated when the designation content of the photographic region CA, which is set through the image display portion 310, the upper and lower jaw selection portion 320, and the selection range setting portion 330.

The start button 343 is manipulated to provide a designation to start the photographing of the photographic region CA based on the designation content fixed by the set button 341. The mode button 344 is manipulated to select various modes. The photography mode selection screen MSW in FIG. 10 is displayed by manipulating the mode button 344 to be selected. The mode button 344 is a button that switches among the pseudo intraoral radiography mode, the CT photography mode, the panoramic photography mode, and the cephalic photography mode. In other words, the mode button 344 acts as a photography mode switching part that switches the photography mode performed by the X-ray photography apparatus 1. The return button 345 is manipulated to return to the initial screen (for example, photography mode setting screen MSW indicated in FIG. 10).

In the photographic region setting screen 300, the photographic region of the CT photography can be set or the photographic region of the pseudo intraoral radiography can be set.

In order to set the photographic region CA, the photographic region line 313 is set in the photographic region setting screen 300 displayed on the manipulation display part 61 so as to surround a photographing target object OB. Particularly, one of the upper jaw, the lower jaw, and the upper and lower jaws is selected in the upper and lower jaw selection portion 320 according to the position of the photographing target object. In the dental arch image 211 displayed in the image display portion 310, the center of the photographic region line 313 is designated through the designation cursor 312, and the radius (or a diameter) of the photographic region line 313 is input in a text box 331. The position and the size of the photographic region line 313 are set such that the local photographing target object is surrounded by the photographic region line 313.

In the case that the photographic region line 313 set in this manner is directly used as the photographic region CA, the photographic region CA is a solid cylinder having a true circle shape in a planar view. The height of the solid cylinder is determined according to the region (the upper jaw, the lower jaw, or the upper and lower jaws) designated through the upper and lower jaw selection portion 320. For the CT photography, the photographic region CA of the cylindrical body is irradiated with the X-ray cone beam BX1. For the pseudo intraoral radiography, the tooth included in the set photographic region CA is the photographing target. Accordingly, the manipulation display part 61 (or the manipulation display part 62) acts as a photographic region designation part 610 (see FIG. 3) that designates the photographic region of the pseudo intraoral radiography.

In the CT photography, when the extent of the photographic region CA viewed in the axial direction of the body axis MX1 of a patient is determined, the extent of the photographic region CA may be selected from one of at least "local (for example, the diameter of about 40 mm including part of the jaw)" and "wide (for example, the diameter of about 100 mm including the entire jaw)". In this case, the photography mode of the main body 2 is set to the local CT photography mode by setting "local" through the mode setter 601 of the main body controller 60, and the photography mode of the main body 2 is set to the wide CT photography mode by selecting "wide". The X-ray beam forming mechanism 13 may form the X-ray cone beam BX1 according to the size of the set CT photographic region to perform the local CT photography or the wide CT photography.

On the photography mode selection screen MSW, a selection screen for selecting one of the local CT photography mode and the wide CT photography mode may be displayed in the case that the CT photography mode button CM is manipulated to be selected. The local CT photography mode or the wide CT photography mode may be set based on the selection manipulation on the selection screen.

In the above explanation, the manipulation display part 61 (or the manipulation display part 62) includes the touch panel, and the setting manipulation of the photographic region CA is received by manipulating the designation cursor 312 displayed on the photographic region setting screen 300. Alternatively, the manipulation display part 61 may include a liquid crystal screen, and the setting manipulation of the photographic region CA may be received through a pointing device such as a mouse or a manipulation button placed near the manipulation display part 61.

The region fixed in each tooth may be set to the photographic region CA indicated by the photographic region line 313, or the size and the position of the photographic region CA may variably be adjusted. For example, the variable adjustment can be performed by moving the photographic region line 313 by a pointer through mouse manipulation. According to the adjusted region, the X-ray beam forming mechanism 13 adjusts the width of the X-ray cone beam BX1, or the moving mechanism 200 adjusts the position of the turning arm 30.

In the above explanation, the photographic region setting screen 300 is displayed on the manipulation display part 61 to receive the setting manipulation of the photographic region CA. Alternatively, the photographic region setting screen 300 may be displayed on the display part 81 of the image processing device 8, and the setting manipulation of the photographic region CA may be received in the image processing device 8.

The pseudo intraoral radiography mode may also be configured such that photographic region CA is set to the upper jaw by the UPPER button 321, or such that the photographic region CA is set to the lower jaw by the LOWER button 323.

For the pseudo intraoral radiography mode, the photographic region line 313 may be used in setting the photographic region CA. Alternatively, as indicated in FIG. 11, an oval photographic region line 314 is displayed along the dental arch, and the photographic region CA corresponding to the oval photographic region line 314 may be set.

For the pseudo intraoral radiography mode, because one or more specific teeth are the photographing target unlike in the CT photography mode, it is not necessary that the region irradiated with the X-ray be strictly displayed as the photographic region. Accordingly, the photographic region may be set by not the photographic region lines 313 and 314 indicating a closed region but by a simple line 315 indicating the cross-section. The photographic region lines 313 and 314 and the line 315 may simultaneously be displayed.

The photographic region CA designed by the photographic region lines 313 and 314 or the line 315 may be set to a predetermined region for every tooth, and the size and the position of the photographic region CA may variably be adjusted. For example, the variable adjustment can be performed by moving the photographic region lines 313 and 314 or the line 315 through manipulation to move a pointer based on mouse manipulation. According to the adjusted region, the X-ray beam forming mechanism 13 adjusts the width of the X-ray cone beam BX1, or the moving mechanism 200 adjusts the position of the turning arm 30.

For the panoramic photography, the photographing target such as the panoramic photography of the entire jaw, the panoramic photography of only the upper jaw, and the panoramic photography of only the lower jaw may be selected by adjusting the positions of the vertically-shielding plates 14 and the horizontally-shielding plates 15. In this case, it is considered that the photographic region CA is set to the upper jaw by the UPPER button 321, set to the lower jaw by the LOWER button 323, and set to the upper and lower jaws, namely, the entire jaw by the FULL button 322.

Additionally, the setting can be performed such that partial panoramic photography in which only the panoramic photography is performed to the partial region of the dental arch, and the photographic region line may be set on the photographic region setting screen 300 in the designated range of the partial region like the pseudo intraoral radiography. At this point, the manipulation can be performed like the designation of the photographic region in the pseudo intraoral radiography mode.

<Another Example of Photographic Region Setting Screen>

Figure 12:
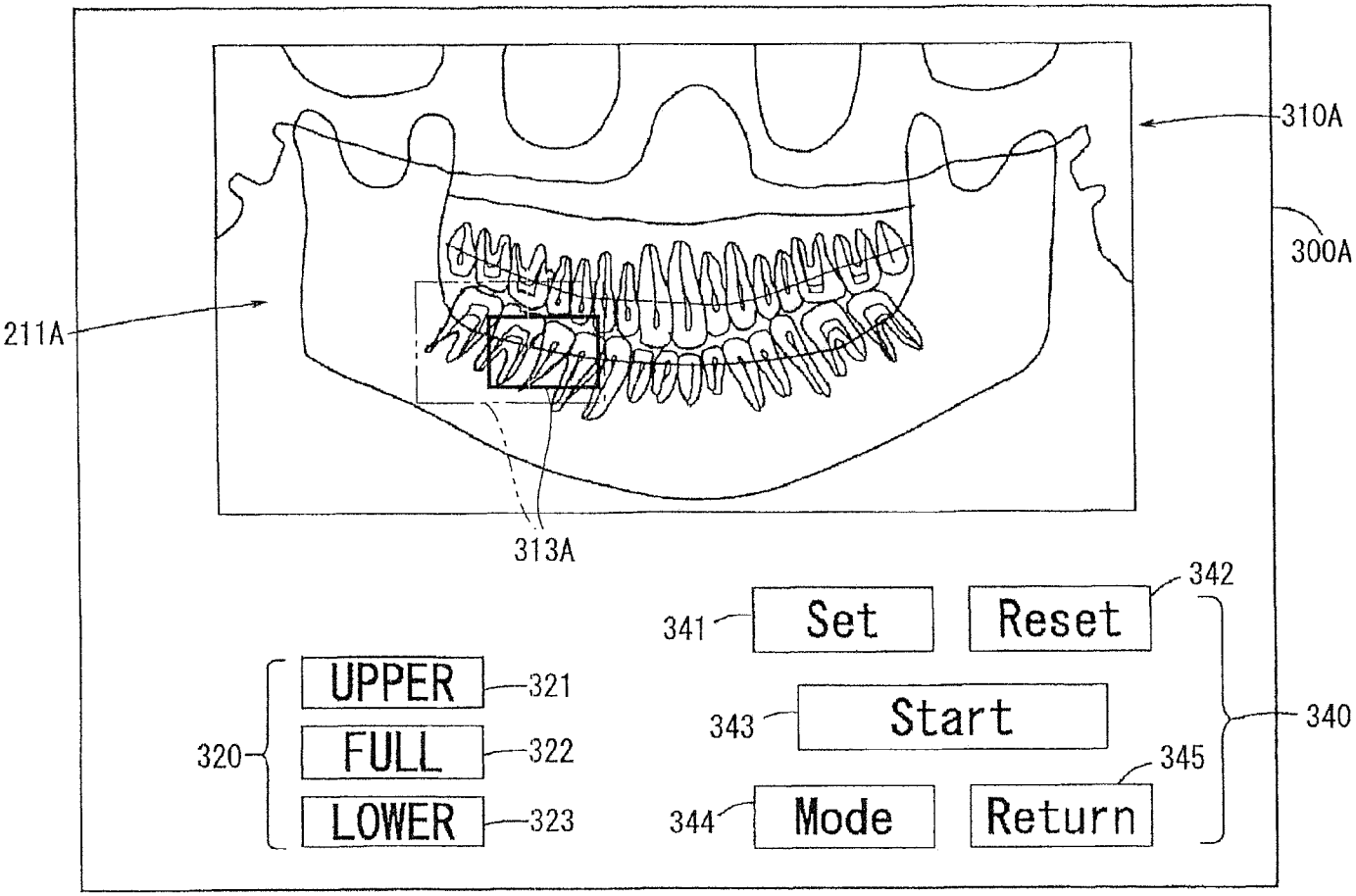
FIG. 12 is a view indicating another photographic region setting screen.

FIG. 12 is a view indicating another photographic region setting screen 300A. Like the photographic region setting screen 300 indicated in FIG. 11, the photographic region setting screen 300A includes an image display portion 310A, the upper and lower jaw selection portion 320, and the condition setting portion 340. In the photographic region setting screen 300A, the functions of the upper and lower jaw selection portion 320 and the condition setting portion 340 are similar to those of the upper and lower jaw selection portion 320 and the condition setting portion 340 in the photographic region setting screen 300. The photographic region setting screen 300A indicated in FIG. 12 has a feature point that a picture (a panoramic image 211A) of dental arch viewed in the Y-axis direction is displayed.

Instead of the dental arch image 211, the panoramic image 211A obtained by previously performing the panoramic photography to the dental arch region of the subject M1 using the X-ray is displayed in the image display portion 310A. In the image display portion 310A, the photographic region CA is set on the panoramic image 211A. In the example illustrated in FIG. 12, a photographic region line 313A is set first. Although not illustrated, the photographic region line 313A is designated using the designation cursor 312. In FIG. 12, the size of the photographic region line 313A may arbitrarily be changed as indicated by the solid line and the alternate long and two short dashed line.

In the image display portion 310A, designation information that is input to designate the photographic region CA with respect to the panoramic image 211A is transmitted to the image processing device 8. The image processing device 8 transmits the information on the photographic region line 313A corresponding to the received designation information to the manipulation display part 61.

The manipulation display part 61 that receives the information on the photographic region line 313A displays the panoramic image 211A and the photographic region line 313A based on the received information in the image display portion 310A of the photographic region setting screen 300A while superimposing the panoramic image 211A and the photographic region line 313A on each other. After the superimposition display, a processing flow is similar to that of the photographic region setting screen 300.

Three-dimensional positional information on a panoramic cross-sectional position of the subject M1 fixed to the subject retention part 421 (*also referred to as a "head retainer"*) can be easily identified by calculation processing of the image processor 801b from the positional relationship between the subject retention part 421 and the panoramic cross-sectional position being set. Accordingly, three-dimensional coordinates at the position designated with respect to the panoramic image 211D is acquired by the calculation.

The panoramic image 211A is not limited to the panoramic image acquired by the X-ray photography apparatus 1, but the panoramic image acquired by another photographing apparatus may be used. In this case, if the positional information on the panoramic cross-section at the time of the panoramic photography is known, the three-dimensional coordinates at the position designated on the panoramic image 211A can be acquired by the calculation.

Figure 13:
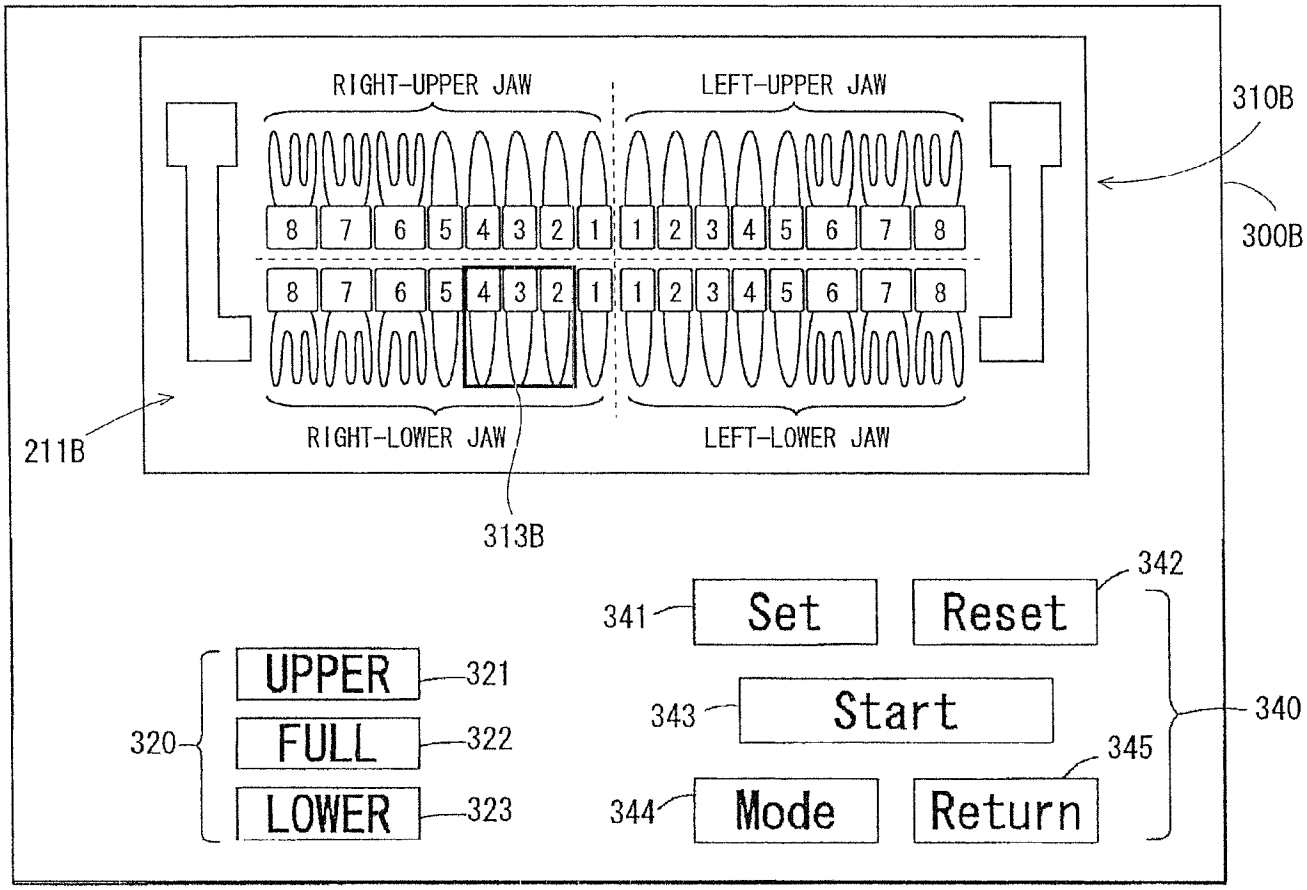
FIG. 13 is a view indicating still another photographic region setting screen.

FIG. 13 is a view indicating another photographic region setting screen 300B. In the photographic region setting screen 300A in FIG. 12, the photographed image obtained by performing the panoramic photography to the subject M1 is displayed as the panoramic image 211A in the image display portion 310A. However, it is not always necessary that the panoramic image 211A be the photographed image. In the photographic region setting screen 300B in FIG. 13, an illustration 211B which is an imitation of the photographed panoramic image is displayed in an image display portion 310B. Illustrations of the eight teeth are drawn in the illustration 211B in each of the right-upper jaw, the left-upper jaw, the right-lower jaw, and the left-lower jaw. The rectangular photographic region line 311B may be set on the illustration 211B.

It is not always necessary that the panoramic image 211A be the photographed image obtained by performing the panoramic photography to the subject M1. For example, the panoramic cross-section image of the jaw of a standard skeleton or the illustration which is an imitation of the photographed panoramic image may be used as the panoramic image 211A.

In the above explanation, the photographic region setting screen 300 is displayed on the manipulation display part 61 to receive the setting manipulation of the photographic region CA. Alternatively, the photographic region setting screen 300 is displayed on the display part 81 of the image processing device 8, and the setting manipulation of the photographic region CA may be received in the image processing device 8.

The collected frame data is sequentially transferred to the image processing device 8, and stored in a storage part 802. The image processor 801b performs the calculation processing to the collected frame data according to each photography mode. For example, for the CT photography, the frame data is reconstructed into three-dimensional data. The reconstruction calculation processing of the image processor 801b includes predetermined preprocessing, filtering processing, and back projection processing. Various technologies including a well-known technology can be applied to the image processing of the X-ray image.

<Irradiation Direction of X-Ray Beam>

<<Control of Irradiation Direction During Panoramic Photography>>

Figure 14:
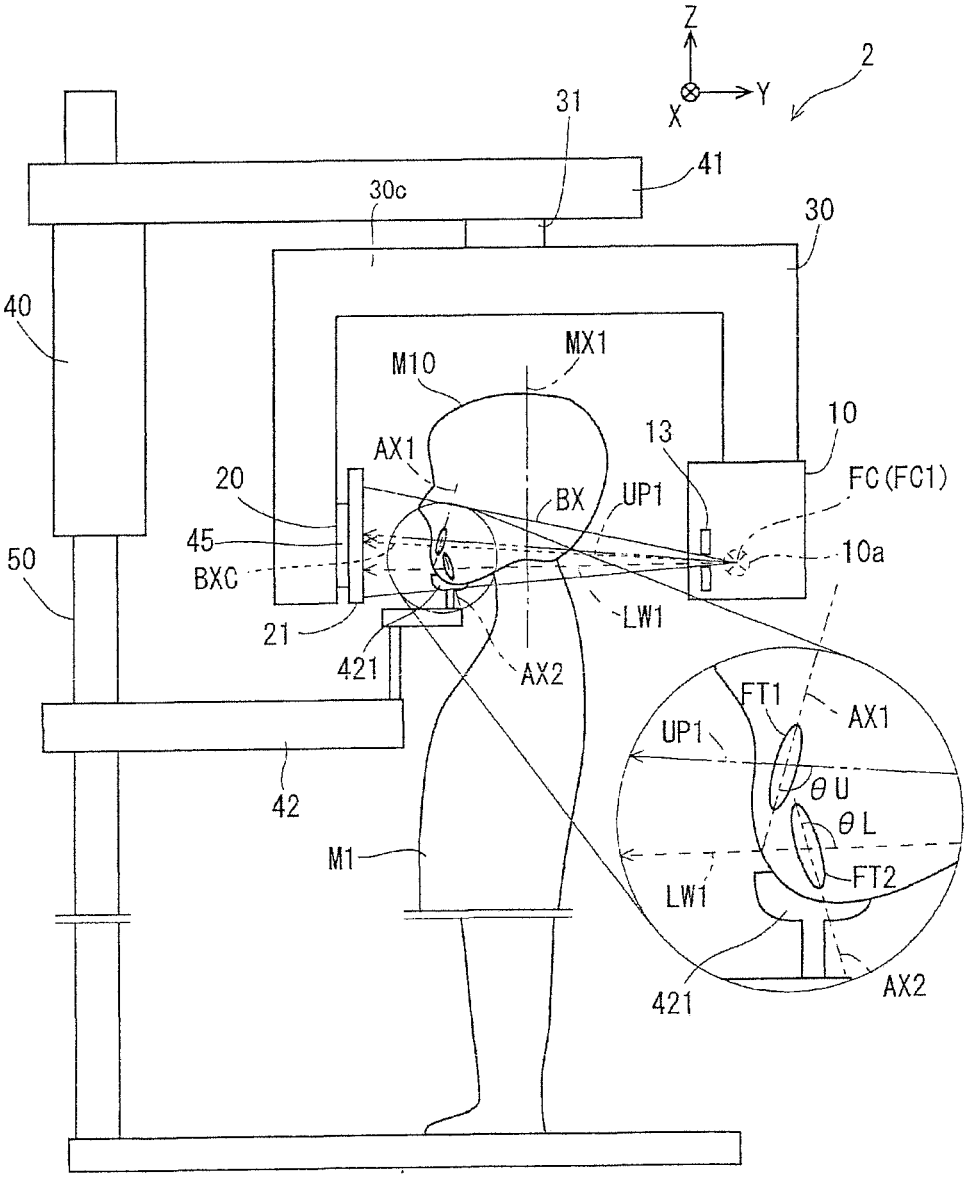
FIG. 14 is a view indicating an irradiation direction of an X-ray beam during panoramic photography.

FIG. 14 is a view indicating the irradiation direction of the X-ray beam BX during the panoramic photography. FIG. 14 indicates a state in which the subject M1 is irradiated from straight behind with the X-ray beam BX (specifically, the X-ray slit beam). As indicated in FIG. 14, in the panoramic photography, since it is sufficient that the upper and lower portions of the X-ray beam BX include the upper and lower jaws in the head M10 of the subject M1, there is little or no particular limitation to the irradiation direction of the X-ray beam BX. For example, an angle θU formed by an X-ray UP1 transmitted through the center portion of an upper jaw anterior tooth FT1 and a tooth axis AX1 of the upper jaw anterior tooth FT1 is not 90 degrees, and an angle 8L formed by an X-ray LW1 transmitted through the center portion of a lower jaw anterior tooth FT2 and a tooth axis AX2 of the lower jaw anterior tooth FT2 is not 90 degrees. However, the irradiation direction during the panoramic photography is controlled such that a center axis BXC of the X-ray beam BX is preferably oriented upward with respect to the direction (in this case, the horizontal direction such as the Y-axis direction) orthogonal to the axial direction of the body axis MX1.

An influence of the photographing of an area that is neither the tooth nor a jaw joint can be reduced by upwardly orienting the X-ray beam BX. The center axis BXC may not be strictly orthogonal to the axial direction of the body axis MX1, but it is sufficient that the center axis BXC is substantially orthogonal to the axial direction of the body axis MX1. As used herein, "substantially orthogonal" means a concept including "orthogonal".

In the X-ray photography apparatus 1, the elevating part 40 and the X-ray beam forming mechanism 13 can relatively change the irradiation direction of the X-ray beam BX to the head M10 of the subject M1 with respect to the axial direction of the body axis MX1. The X-ray beam forming mechanism 13 is an example of the irradiation direction changing part.

<<Control of Irradiation Direction During Pseudo Intraoral Radiography>>

Figure 15:
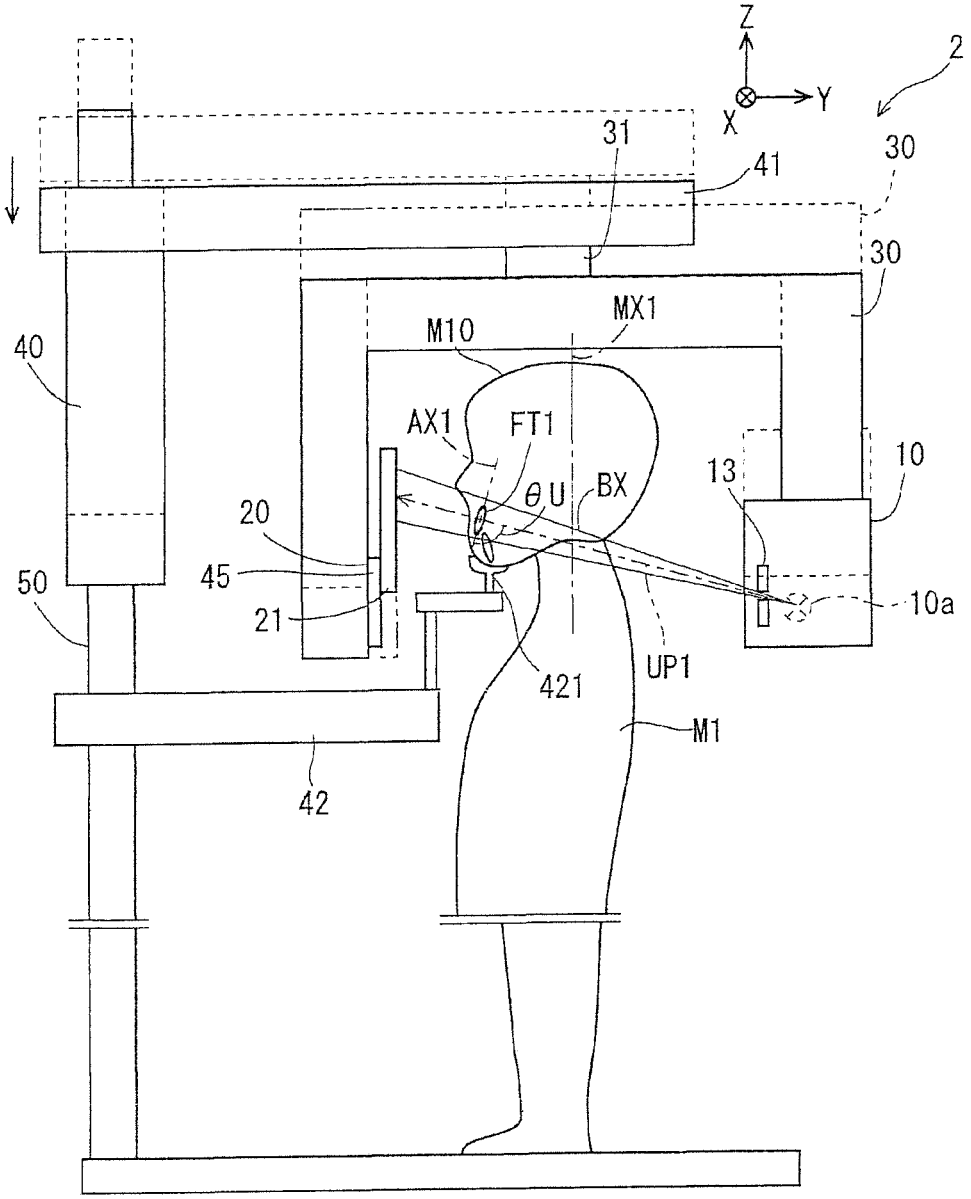
FIG. 15 is a view indicating an irradiation direction of the X-ray beam during pseudo intraoral radiography in which an upper jaw anterior tooth is set to a photographing target.

FIG. 15 is a view indicating the irradiation direction of the X-ray beam BX during the pseudo intraoral radiography in which the upper jaw anterior tooth FT1 is set to the photographing target. The pseudo intraoral radiography in FIG. 15 corresponds to the intraoral radiography by the paralleling technique. FIG. 15 is a view when the subject M1 (the test person) is laterally viewed from the left, and the +y-direction is matched with the −Y-direction.

As indicated in FIG. 15, in the pseudo intraoral radiography, the upper jaw anterior tooth FT1 is irradiated with the X-ray beam BX such that the X-ray UP1 passing through the center portion of the upper jaw anterior tooth FT1 is orthogonal to the tooth axis AX1 of the upper jaw anterior tooth FT1 that is part of the row of teeth (that is, the angle θU is 90 degrees). Since the upper portion of the upper jaw anterior tooth FT1 is on the rear side (that is, the +Y-side) of the subject M1 and the lower portion of the upper jaw anterior tooth FT1 is on the front side (that is, the −Y-side) of the subject M1, the tooth axis AX1 of the upper jaw anterior tooth FT1 is inclined. Therefore, it is necessary to upwardly control the irradiation direction of the X-ray beam BX.

Here, preferably the X-ray UP1 is orthogonal to the tooth axis AX1. However, it is only necessary to obtain the image of the tooth that is inclined as little as possible, and it is sufficient that the X-ray UP1 is substantially orthogonal to the tooth axis AX1.

A detection surface of the X-ray detector is controlled so as to be parallel or substantially parallel to the tooth axis AX1. In the present invention, the pseudo intraoral radiography that simulates the paralleling technique of the intraoral radiography is also referred to as a pseudo paralleling technique. The setting of the irradiation direction of the X-ray beam BX is previously determined based on the inclination of the tooth axis AX1 of a tooth of the standard skeleton. Alternatively, the operator may manually input the setting of the irradiation direction of the X-ray beam BX.

In the X-ray tube of the X-ray generator 10a, a thermal electron generated by a negative electrode collides with a positive electrode, thereby generating the X-ray. The X-ray travels while spreading with a point at which the thermal electron collides with the positive electrode as a starting point. Occasionally, the starting point at which the X-ray is generated is referred to as an actual focal spot, and the actual focal spot viewed in the direction in which the upper jaw anterior tooth FT1 is irradiated with the X-ray is referred to as an effective focal spot. In FIG. 14, the actual focal spot and the effective focal spot are designated by an actual focal spot FC and an effective focal spot FC1. The X-ray UP1 is generated from the effective focal spot FC1, and passes through the center portion of the upper jaw anterior tooth FT1.

In the example indicated in FIG. 15, in order to perform the irradiation with the X-ray beam BX, the turning arm 30 (the support) is lowered below the height (indicated by a broken line) in the panoramic photography by driving the elevating part 40. The position of the X-ray generator 10a (more particularly, the position of the effective focal spot FC1) is lowered with respect to the head of the subject M1 (the test subject) by lowering the turning arm 30, which allows the irradiation direction of the X-ray beam BX to be oriented upward. In other words, the elevating part 40 acts as a third elevating mechanism that vertically displaces the turning arm 30 in parallel with the axial direction of the turning shaft 31 to change the height position at which the X-ray beam BX is emitted. Because the turning arm 30 is elevated and lowered with respect to the subject M1, the subject M1 does not need to be elevated and lowered. Therefore, the burden on the subject M1 (the test subject) can be reduced.

The photographing in FIG. 15 is controlled such that the irradiation direction (the axial direction of the center axis BXC of the X-ray beam BX) of the X-ray beam BX is oriented upward by driving the X-ray beam forming mechanism 13. The X-ray beam forming mechanism 13 relatively changes the irradiation direction of the X-ray beam BX to the head M10 of the subject M1 with respect to the axial direction of the body axis MX1. In other words, the X-ray beam forming mechanism 13 vertically changes the irradiation direction of the X-ray beam BX along the axial direction of the body axis MX1. As described above, the irradiation direction of the X-ray beam BX is changed by the shielding-plate vertically-moving mechanism 16a (see FIG. 4) serving as the first elevating mechanism of the X-ray beam forming mechanism 13. In conjunction with the change of the irradiation direction by the first elevating mechanism, an X-ray-detector drive part 45 that acts as the second elevating mechanism is driven to elevate the X-ray detector 21 to a predetermined height such that the X-ray beam BX is incident to the detection surface without trouble. The X-ray-detector drive part 45 is controlled by an X-ray-detector drive controller 603 (see FIG. 3) of the main body controller 60.

Although not illustrated, for example, the X-ray-detector drive part 45 is constructed by a member that guides the X-ray detector 21 along the Z-direction and a roller that is fixed to the shaft of a motor fixed in the base portion of the X-ray-detector drive part 45, and the X-ray detector 21 is driven to be elevated and lowered while the roller abuts on the rear surface of the X-ray detector 21. Alternatively, the X-ray-detector drive part 45 is constructed by a member that guides the X-ray detector 21 along the Z-direction and a male screw portion in which a female screw portion fixed to the rear surface of the X-ray detector 21 is turnably fixed to the base portion of the X-ray-detector drive part 45, and the X-ray detector 21 is driven to be elevated and lowered in the Z-direction by the motor as which is the drive source.

In the dental arch having the general shape, since the upper portion of the upper jaw anterior tooth FT1 is on the rear side (that is, the +Y-side) of the subject M1 and the lower portion of the upper jaw anterior tooth FT1 is on the front side (that is, the −Y-side) of the subject M1, the tooth axis AX1 is inclined. On the other hand, the tooth axis of a tooth except the anterior tooth or a tooth near the anterior tooth is hardly inclined with respect to the direction toward the cheek side from the tongue side or an opposite direction thereto. Therefore, the irradiation direction of the X-ray beam BX for tooth except the anterior tooth or a tooth near the anterior tooth is set to the horizontal direction with respect to the axial direction of the body axis MX1 unlike the case that the pseudo intraoral radiography is performed to the anterior tooth. In other words, the irradiation direction of the X-ray beam BX varies with respect to the axial direction of the body axis MX1 depending on the position of the pseudo intraoral radiography region.

<Correction of Distortion>

In the case that the pseudo intraoral radiography of the upper jaw anterior tooth FT1 is performed by the configuration in FIG. 15, the upper portion (the tooth root portion side) is distant from the detection surface of the X-ray detector 21 while the lower portion (the tooth crown portion side) is close to the detection surface of the X-ray detector 21. Therefore, a distortion is generated due to the difference in magnification rate in the X-ray image of the upper jaw anterior tooth FT1 obtained by the X-ray detector 21. Accordingly, the distortion is preferably corrected through the image processing. Specifically, the following processing is performed.

For convenience of explanation, it is assumed that FT1I (not illustrated) is the X-ray image of the upper jaw anterior tooth FT1 received by the detection surface of the X-ray detector 21, that EL1 is the magnification rate on the portion of tooth root side, and that EL2 is the magnification rate on the portion of tooth crown side. The magnification rate EL1 and the magnification rate EL2 in the X-ray image FT1I have a relationship of EL1>EL2. The ratio (vertical width/horizontal width) AS1 of the width in the vertical direction (the z-direction) of the X-ray image FT1I and the width of the horizontal direction (the x-direction) and the ratio (vertical width/horizontal width) AS2 of the real scale vertical width of the anterior tooth FT1 and the real scale horizontal width have a relationship of AS1>AS2.

One of the following pieces of image correction processing is performed.

Processing 1: the correction is performed such that EL1 becomes equal to EL2.

Processing 2: the correction is performed such that AS1 becomes equal to AS2.

Processing 3: the correction is performed such that EL1 becomes equal to EL2 and AS1 becomes equal to AS2.

Because the distortion also exists in a portion except the tooth crown portion and the tooth root portion, the magnification rate is corrected from the tooth root portion to the tooth crown portion. Therefore, the X-ray image FT1I can be brought similar to the X-ray image that is received by the X-ray detection surface disposed perpendicular to the X-ray UP1.

Preferably the correction is also performed, when the X-ray image received by the detection surface of the X-ray detector 21 has the distortion with respect to the real tooth while a tooth except the upper jaw anterior tooth FT1 is set to the photographing target.

Figure 16:
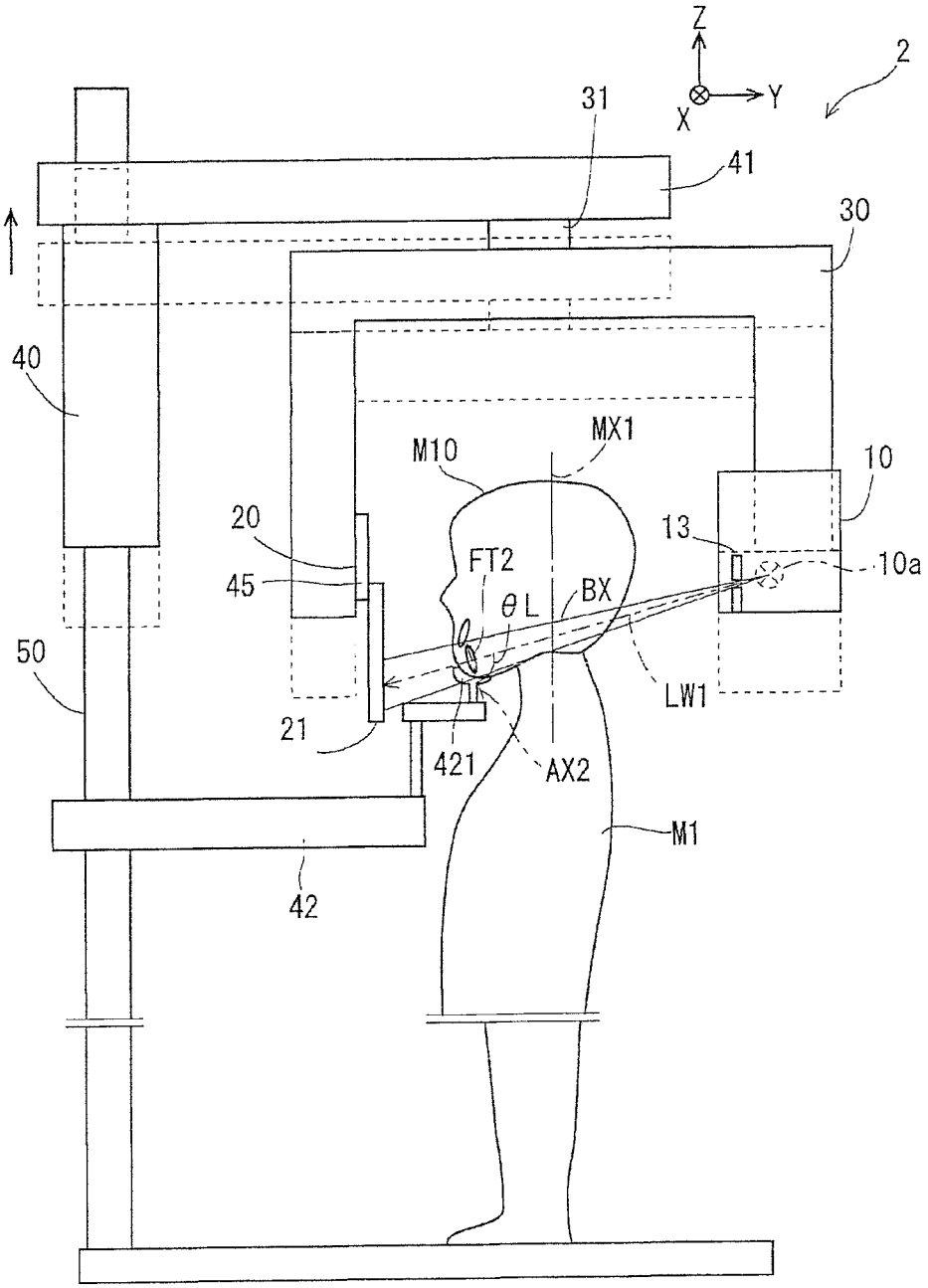
FIG. 16 is a view indicating an irradiation direction of the X-ray beam during the pseudo intraoral radiography in which a lower jaw anterior tooth is set to the photographing target.

FIG. 16 is a view indicating the irradiation direction of the X-ray beam BX during the pseudo intraoral radiography in which the lower jaw anterior tooth FT2 is set to the photographing target. In the tooth axis of the lower jaw anterior tooth FT2, the upper portion is inclined toward the front side (that is, the −Y-side) of the subject M1, and the lower portion is inclined toward the rear side (that is, +Y-side) of the subject M1. Therefore, it is necessary to downwardly control the irradiation direction of the X-ray beam BX.

In FIG. 16, in order to perform the irradiation with the X-ray beam BX, the turning arm 30 is elevated above the height (indicated by the broken line) in the panoramic photography by driving the elevating part 40. The position of the X-ray generator 10a is elevated with respect to the head of the subject M1 (the test subject) by elevating the turning arm 30, which allows the irradiation direction of the X-ray beam BX to be oriented downward. The irradiation direction of the X-ray beam BX is controlled by driving the X-ray beam forming mechanism 13 so as to be oriented downward. The X-ray detector 21 is lowered to the predetermined height by driving the X-ray-detector drive part 45 such that the X-ray beam BX is incident to the detection surface.

Basically, when the tooth is observed from the tongue side toward the cheek side (the inside of the cavity), or when the tooth is observed in the opposite direction, a the sight line direction is desirably orthogonal to the tooth axis. The X-ray image in which the tooth is obliquely looked down from above or obliquely looked up from below is obtained, unless the center axis of the X-ray beam BX is orthogonal to the tooth of the photographing target. In this case, the image in which the tooth is looked shorter than the real size is obtained. Accordingly, the center axis of the X-ray beam is orthogonally incident to the target tooth (that is, the center axis of the X-ray beam BX is orthogonal to the tooth axis), which allows the acquisition of the image that is true to the shape of the tooth with little or no distortion.

The case that the lower jaw is set to the photographing target is similar to the case that the upper jaw is set to the photographing target in that the irradiation direction of the X-ray beam BX is varied with respect to the axial direction of the body axis MX1 depending on the position of the pseudo intraoral radiography region. More specifically, the irradiation angle of the X-ray beam BX with respect to the Z-axis direction, the irradiation range, the position of the turning arm 30, and the turning angle of the turning arm 30 vary in each of the photographic regions of the photographing targets such as the entire jaw, part of the jaw, the tooth of the upper jaw, the tooth of the lower jaw, the tooth a certain region of the upper jaw, and the tooth in a certain region of the lower jaw. Therefore, in each photographic region, the elevating control of the elevating part 40 is performed by the support drive controller 602, the position control of the turning arm 30 is performed by the moving mechanism 200, the drive control of the X-ray beam forming mechanism 13 is performed by the X-ray-regulating-part drive part 101 based on the control of the X-ray-regulating-part drive controller 605, and the position control of the X-ray detector 21 is performed by the X-ray-detector drive part 45 based on the control of the X-ray-detector drive controller 603, as necessary. In the case that the subject-retention-part drive part MH1 needs to drive the subject retention part 421, the subject-retention-part drive part MH1 is also properly controlled based on the control of a subject-retention-part drive controller 604.

<<Control of Irradiation Direction During CT Photography>>

Figure 17:
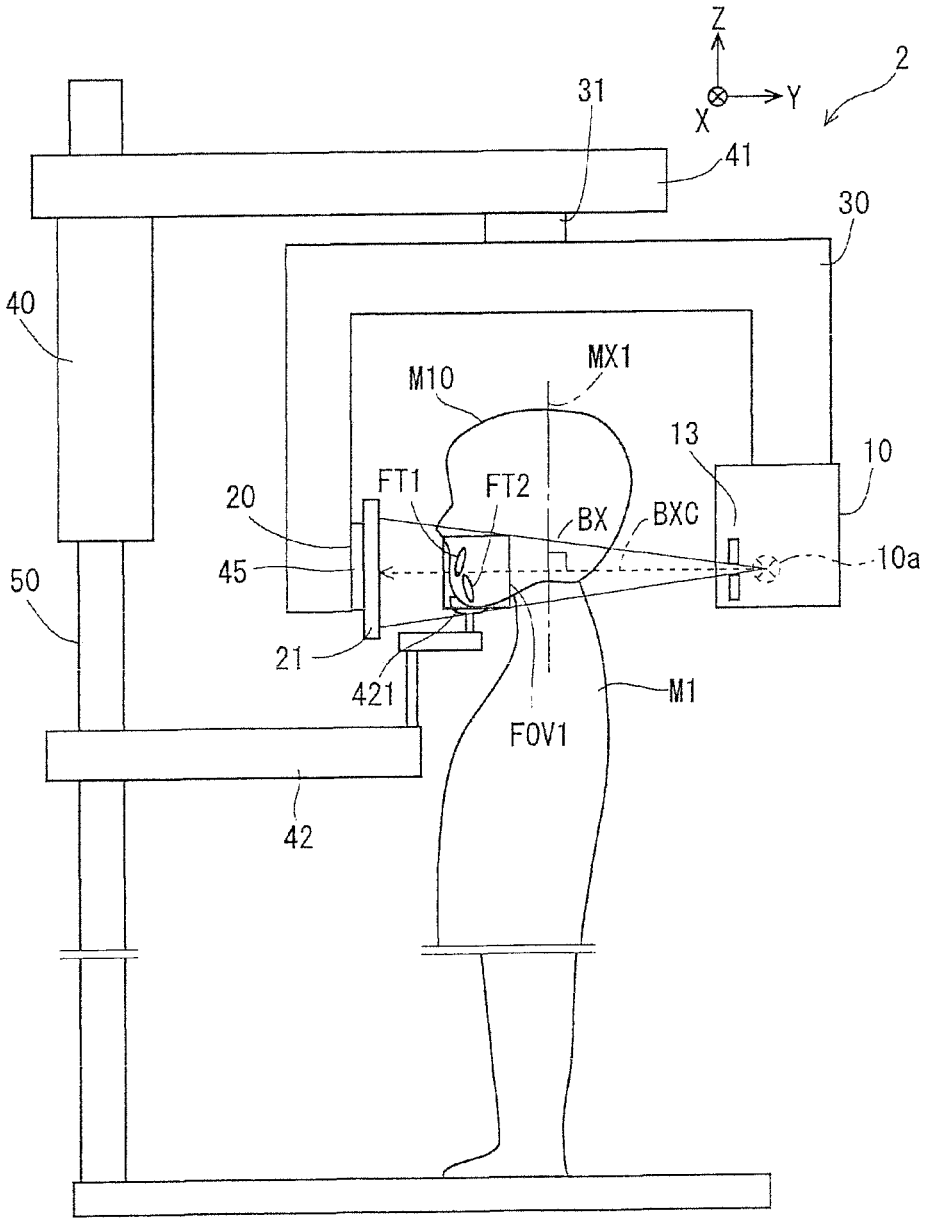
FIG. 17 is a view illustrating an irradiation direction of the X-ray beam during CT photography in which the upper jaw and the lower jaw are set to the photographing target.

FIG. 17 is a view indicating the irradiation direction of the X-ray beam BX during CT photography in which the upper jaw and the lower jaw are set to the photographing target. In the CT photography, the photographic region (Field of View (FOV)) is irradiated with the X-ray beam BX in multiple directions included in the angle range of at least 180 degrees. At this point, the irradiation direction of the X-ray beam is controlled such that the center axis BXC of the X-ray beam passes through the center portion of the photographic region.

For example, in the CT photography in FIG. 17, a solid-cylinder photographic region FOV1 is irradiated with the X-ray beam BX. The photographic region FOV1 has a diameter of about 80 mm to about 100 mm, and includes both upper jaw and lower jaw. The CT photography indicated in FIG. 17 corresponds to the first CT photography mode. The photographic region FOV1 extends along the body axis MX1. In the case that the photographic region FOV1 is set to the photographing target, as indicated in FIG. 17, the photographic region FOV1 is irradiated with the X-ray beam BX such that the center axis BXC of the X-ray beam BX passes through the center of the photographic region FOV1, and such that the center axis BXC is orthogonal to the body axis MX1. Because the body axis MX1 is parallel to the Z-axis direction, the center axis BXC is parallel to an XY plane (a horizontal plane). The center axis BXC may not be strictly orthogonal to the body axis MX1, but it is sufficient that the center axis BXC is substantially be orthogonal to the body axis MX1.

In the CT photography, preferably the pieces of image data are both obtained by irradiating the photographic region FOV1 with the X-ray from one side toward the other side and from the other side toward the one side. Therefore, desirably the photographic region FOV1 is irradiated with the X-ray at an angle at which the pieces of image data are both obtained. Because the same holds true for the horizontal direction and the perpendicular direction, preferably the photographic region FOV1 is irradiated with the X-ray as described above.

Figure 18:
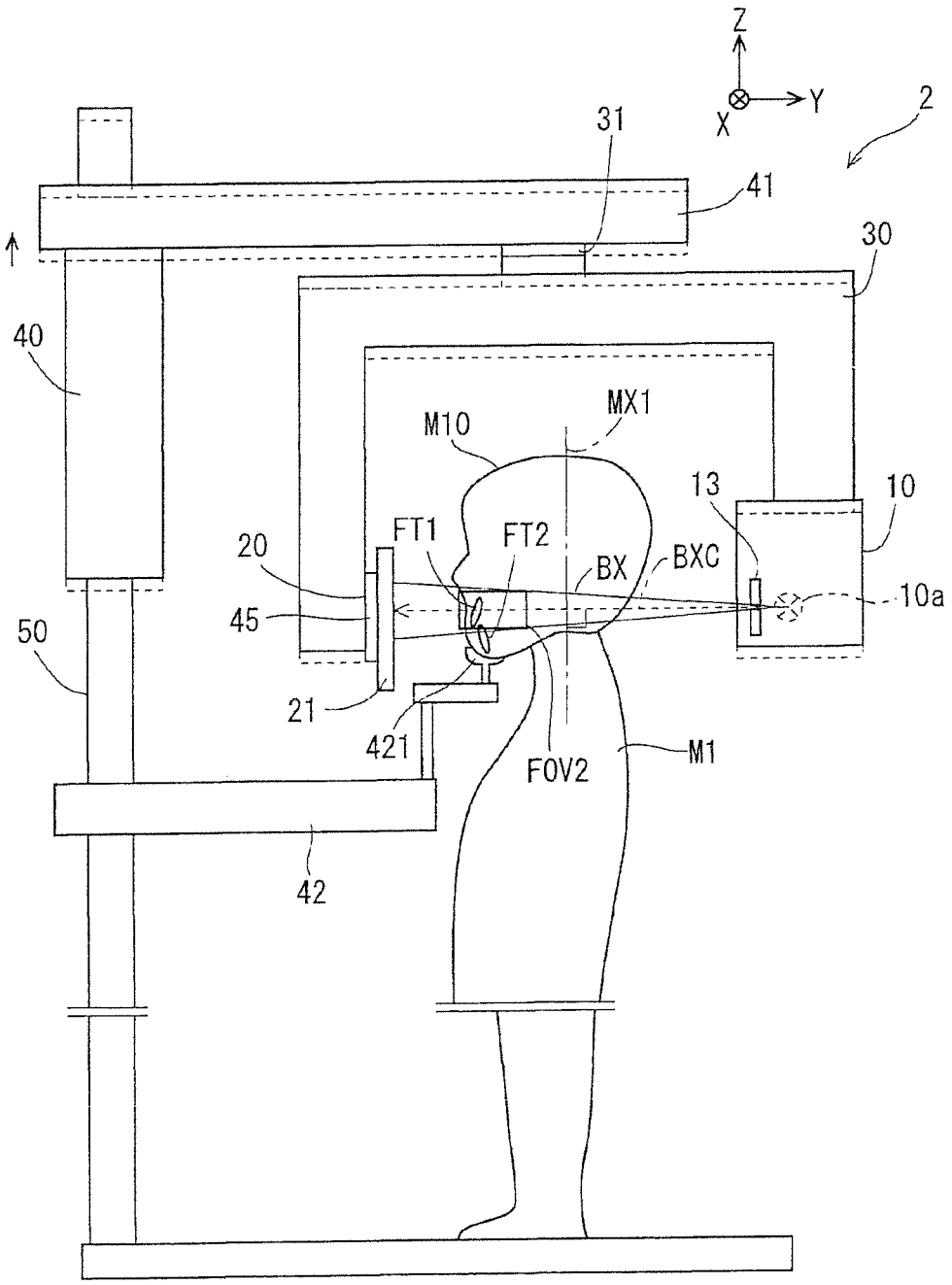
FIG. 18 is a view indicating an irradiation direction of the X-ray beam during the CT photography in which the upper jaw is set to the photographing target.
Figure 19:
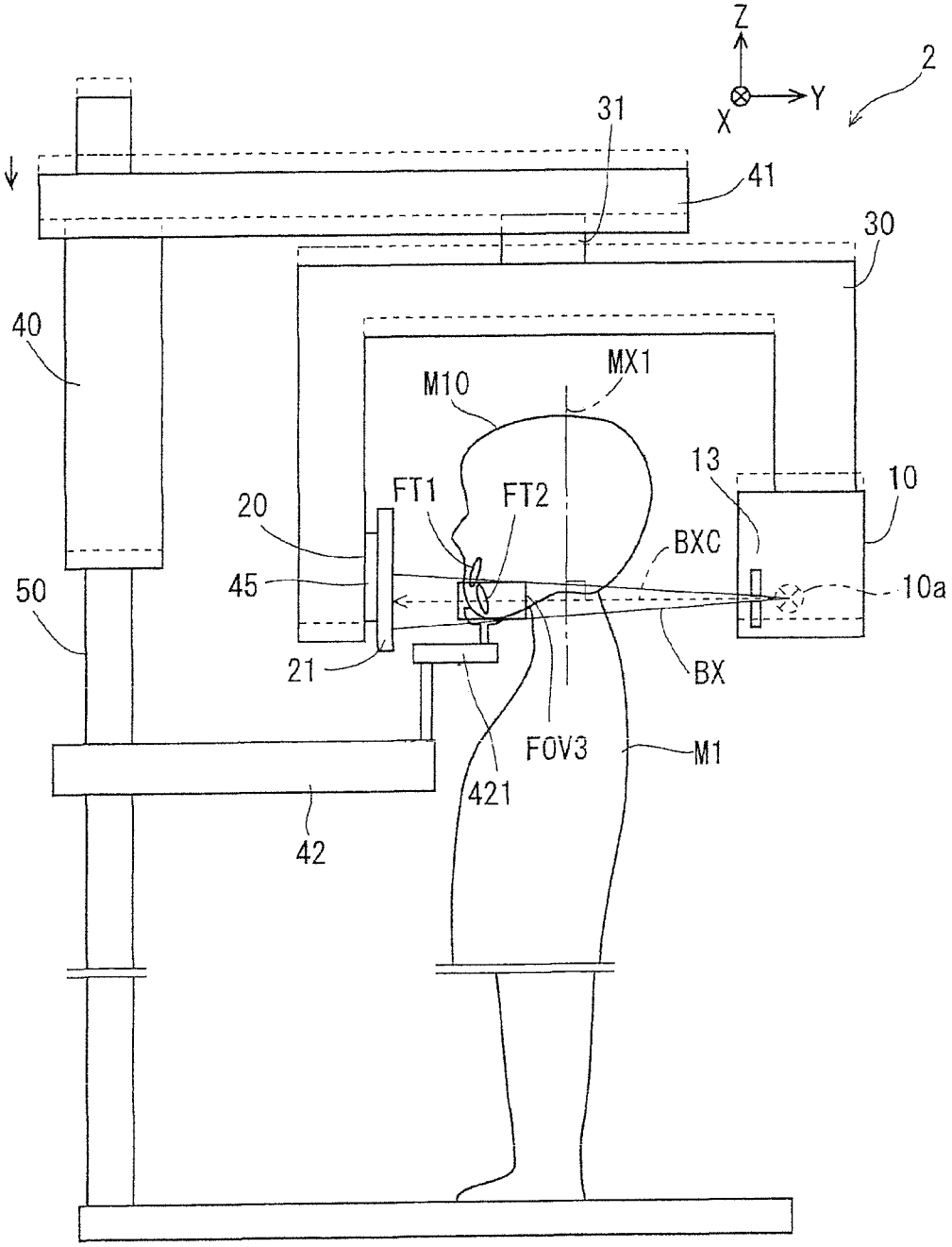
FIG. 19 is a view indicating an irradiation direction of the X-ray beam during the CT photography in which the lower jaw is set to the photographing target.

FIG. 18 is a view indicating the irradiation direction of the X-ray beam BX during the CT photography in which the upper jaw is set to the photographing target. FIG. 19 is a view indicating the irradiation direction of the X-ray beam BX during the CT photography in which the lower jaw is set to the photographing target. A photographic region FOV2 including only the upper jaw except the lower jaw from the upper and lower jaws and a photographic region FOV3 including only the lower jaw except the upper jaw from the upper and lower jaws are the solid-cylinder regions. In the case that the photographic region FOV2 or the photographic region FOV3 is set to the photographing target as well, the photographic region FOV2 or FOV3 is irradiated with the X-ray beam BX in the same manner as in the CT photography of the photographic region FOV1. In other words, the photographic region FOV2 or FOV3 is irradiated with the X-ray beam BX such that the center axis BXC of the X-ray beam BX passes through the center of the photographic region FOV2 or FOV3, and such that the center axis BXC is orthogonal to the body axis MX1. The CT photography indicated in FIGS. 18 and 19 corresponds to the second CT photography mode. The center axis BXC may not be strictly orthogonal to the body axis MX1, but it is sufficient that the center axis BXC is substantially orthogonal to the body axis MX1.

In order to perform the irradiation with the X-ray beam BX, the elevating part 40 is driven to change the height of the turning arm 30 from the height (indicated by the broken line) at which the CT photography is performed to the photographic region FOV1. The irradiation range of the X-ray beam BX is regulated according to the photographic region FOV2 or FOV3 by controlling the X-ray beam forming mechanism 13.

The photographic region of the CT photography is not limited to the solid-cylinder region. The photographic region can be formed into various shapes by horizontally moving the turning arm 30 in turning the turning arm 30.

<Pseudo Intraoral Radiography>

Figure 20:
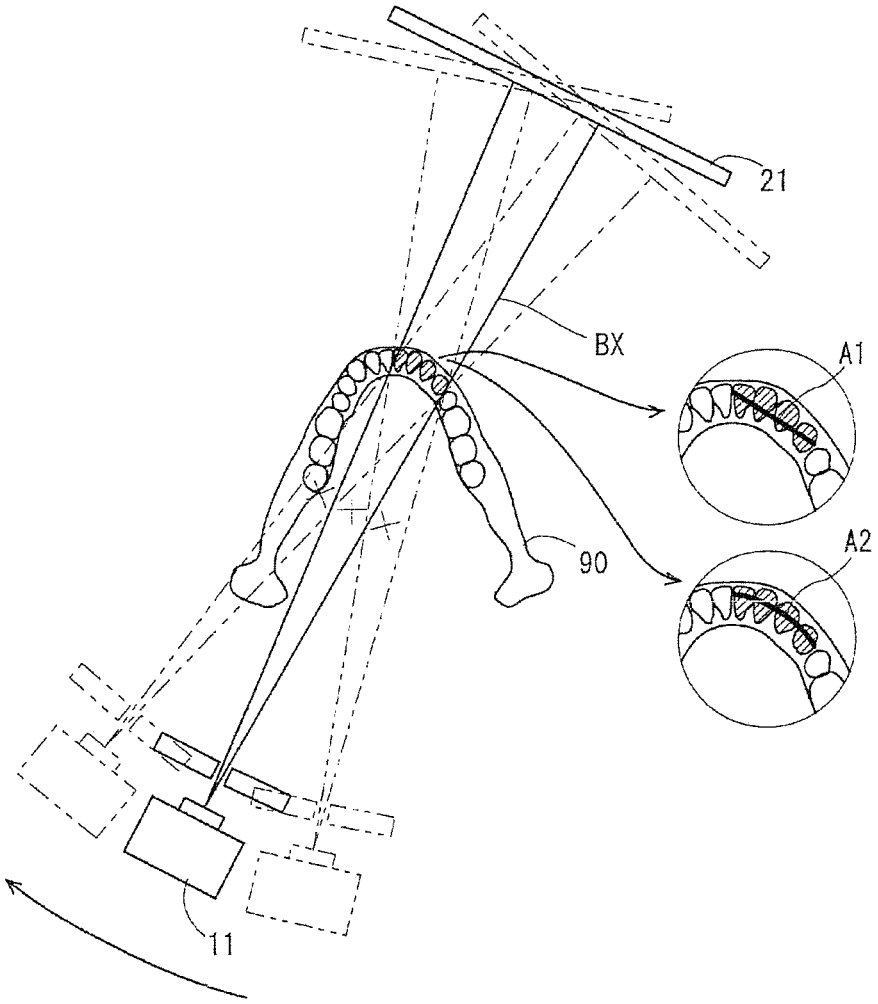
FIG. 20 is a schematic plan view indicating a situation of the pseudo intraoral radiography when viewed in a −Z-direction from a +Z-side.

FIG. 20 is a schematic plan view indicating a situation of the pseudo intraoral radiography when viewed in the −Z-direction from the +Z-side. In FIG. 20, four teeth on the right side in the lower jaw are set to the photographing target. The teeth that are of the photographing target are designated through the photographic region setting screen 300 indicated in FIG. 11.

As indicated in FIG. 20, in the pseudo intraoral radiography, like the conventional tomosynthesis, the X-ray generator 10a and the X-ray detector 21 are turned while the head M10 of the subject M1 is interposed therebetween, thereby the photographing target object (in this case the four teeth) is irradiated with the X-ray beam BX in multiple directions. The projection images obtained by performing the photographing in the plural directions are overlapped while shifted by proper amount in accordance with the turning direction, thereby reconstructing the tomographic image of any cutting plane.

A planar cutting plane A1 or a curved cutting plane A2 curved along the dental arch 90 can be used as the cutting plane for reconstructing the tomographic image (see FIG. 20). The position and shape of the cutting plane can arbitrarily be determined by the reconstruction calculation method, namely, by properly changing the shift amount during the overlapping. Accordingly, the position and shape of the cutting plane may arbitrarily be set according to the purpose of the image diagnosis.

<First Modification of Apparatus Configuration>

Figure 21:
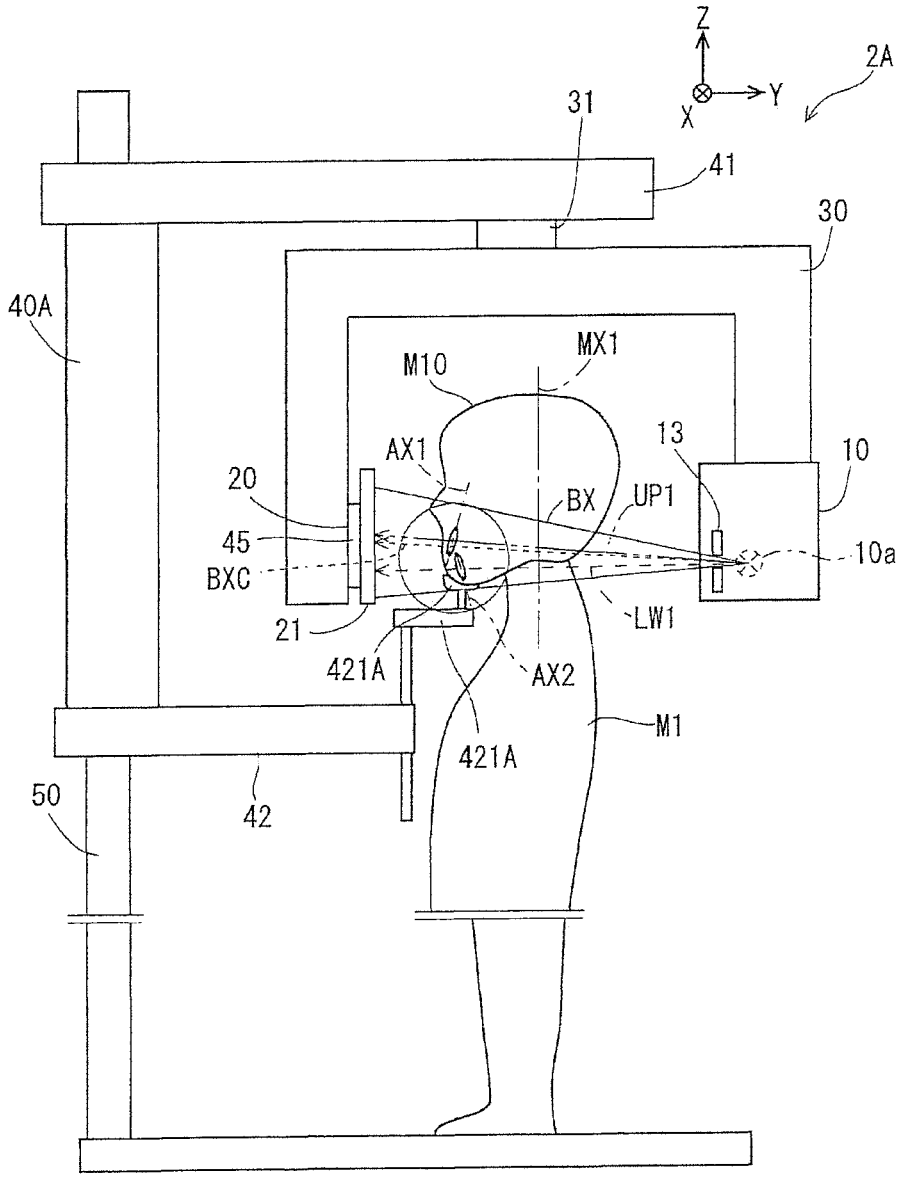
FIG. 21 is a schematic side view indicating a state of a main body according to a first modification of the X-ray photography apparatus of the present invention when the panoramic photography is performed.
Figure 22:
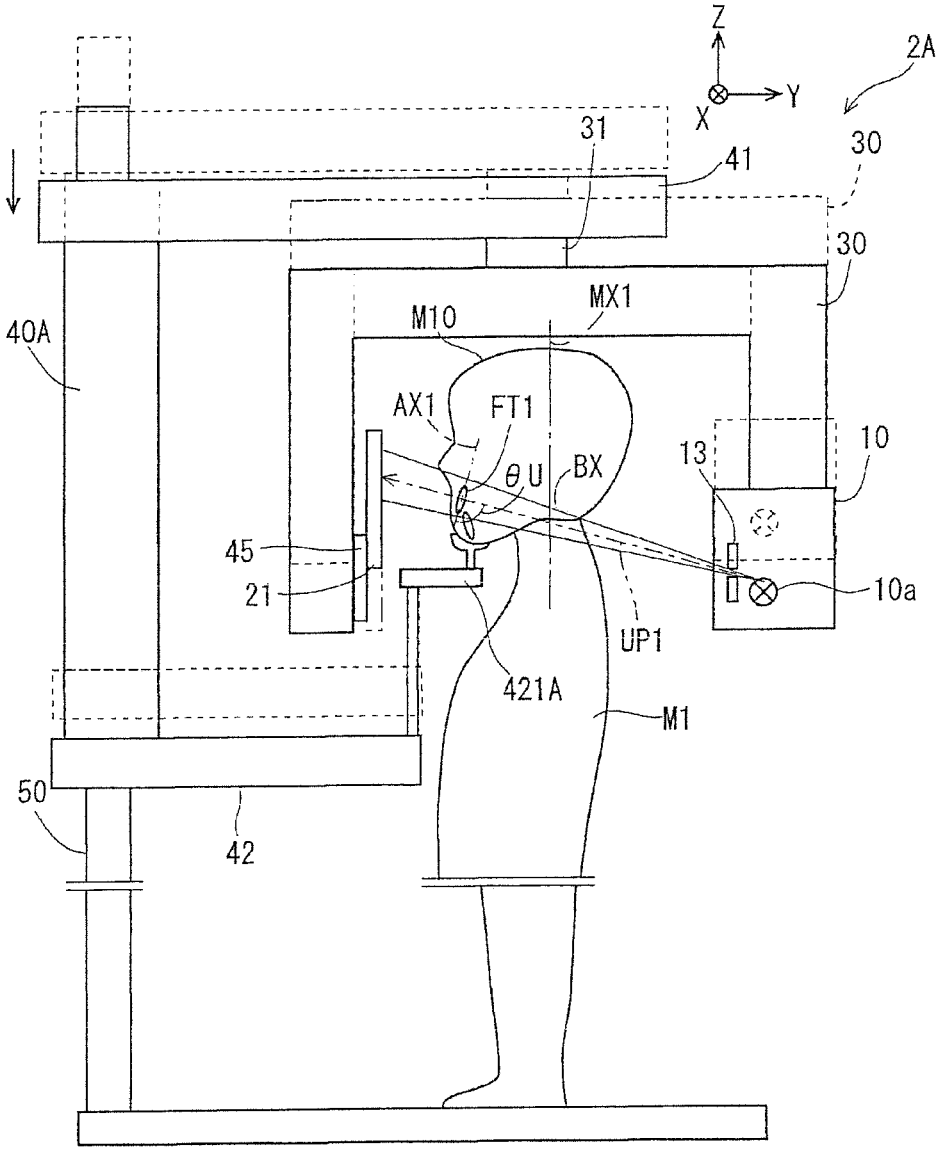
FIG. 22 is a schematic side view indicating a state of the main body according to the first modification when the pseudo intraoral radiography is performed while the upper jaw anterior tooth is set to the photographing target.
Figure 23:
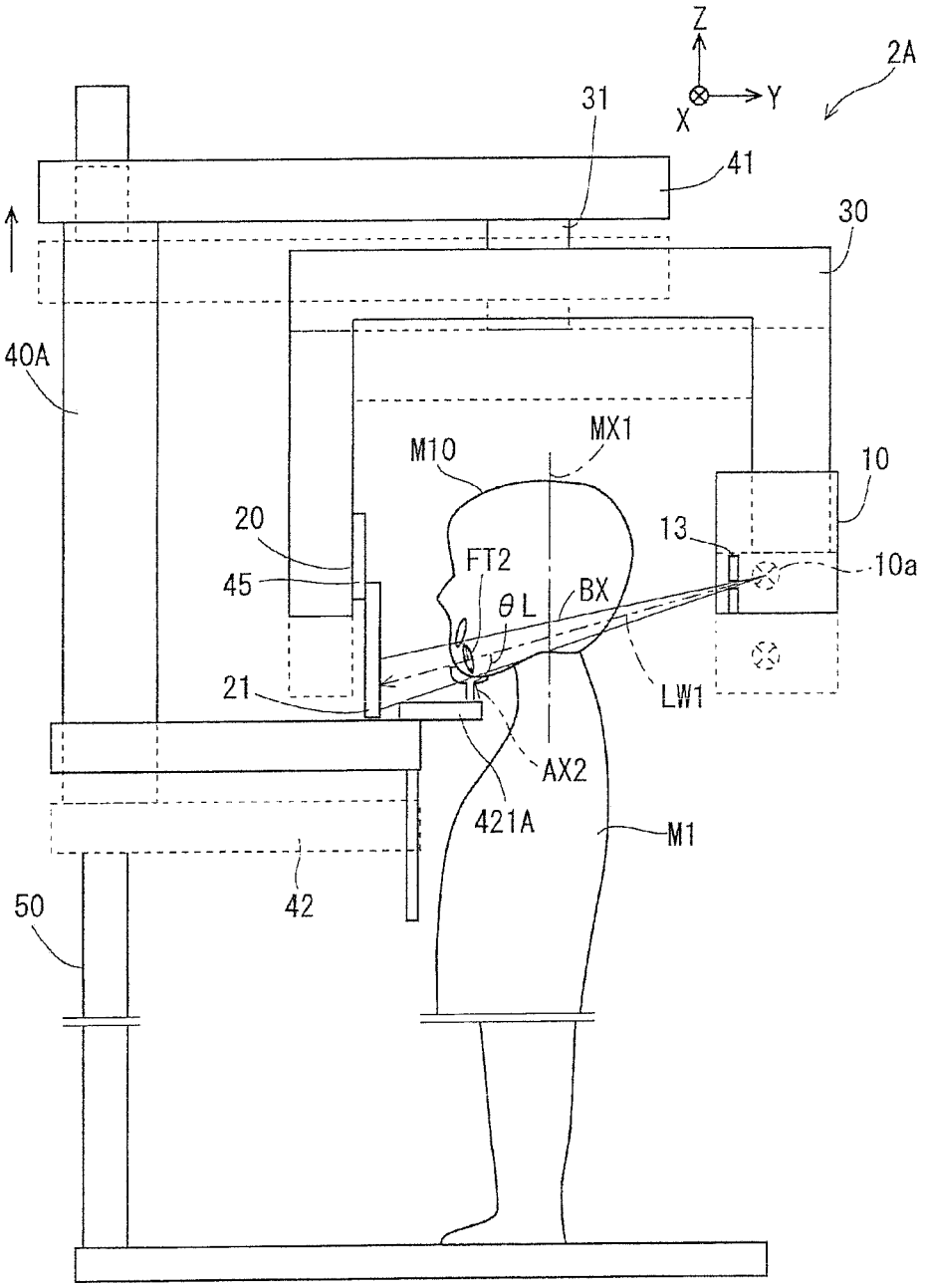
FIG. 23 is a schematic side view indicating a state of the main body according to the first modification when the pseudo intraoral radiography is performed while the lower jaw anterior tooth is set to the photographing target.

FIG. 21 is a schematic side view indicating a state of a main body 2A according to the first modification when the panoramic photography is performed. FIG. 22 is a schematic side view indicating a state of the main body 2A according to the first modification when the pseudo intraoral radiography is performed while the upper jaw anterior tooth FT1 is set to the photographing target. FIG. 23 is a schematic side view indicating a state of the main body 2A according to the first modification when the pseudo intraoral radiography is performed while the lower jaw anterior tooth FT2 is set to the photographing target.

As indicated in FIGS. 21 to 23, in the main body 2A, an elevating part 40A is configured to integrally elevate the turning arm 30 and the lower frame 42. Therefore, a subject retention part 421A is elevated by elevating the lower frame 42. Because the position of the head M10 of the subject M1 is changed when the subject retention part 421A is elevated, in the shown modification, the subject retention part 421A is configured to be able to be elevated relative to the lower frame 42. Specifically, the subject retention part 421A is elevated by a subject-retention-part drive part MH1 as indicated in FIG. 3. The subject-retention-part drive part MH1 is controlled by the subject-retention-part drive controller 604 of the main body controller 60.

Although not illustrated, for example, the subject-retention-part drive part MH1 that elevates the subject retention part 421A may include a guide member that guides a guided member fixed to the subject retention part 421A of the lower frame 42 along the Z-direction and a roller that is fixed to the shaft of the motor of the lower frame 42, and it is considered that in this structure the subject-retention-part drive part MH1 elevates the subject retention part 421A while the roller abuts on the guided member of the subject retention part 421A. Another configuration may be adopted as a matter of course.

<Second Modification of Apparatus Configuration>

As indicated in FIGS. 14 to 19, in the main body 2, because the X-ray detector 21 has the relatively small detection surface, the X-ray-detector drive part 45 vertically elevates and lowers the X-ray detector 21 to detect the X-ray beam BX. Alternatively, the X-ray-detector drive part 45 may be eliminated by using the X-ray detector having a wide detection surface enough not to have to vertically elevate or lower the X-ray detector using the X-ray-detector drive part 45.

<Third Modification of Apparatus Configuration>

Figure 24:
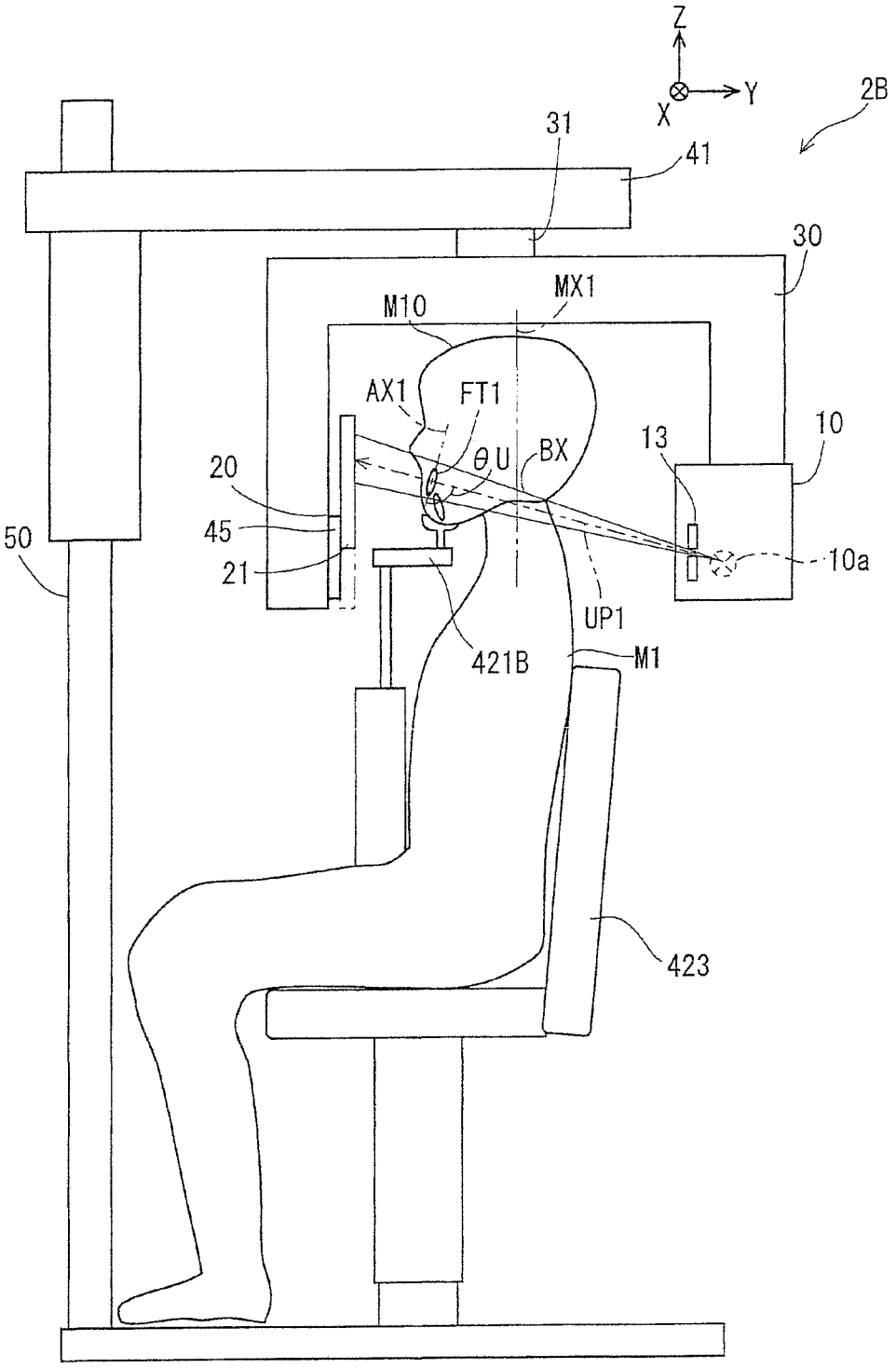
FIG. 24 is a schematic side view indicating a main body according to a third modification.

FIG. 24 is a schematic side view indicating a main body 2B according to the third modification. In the main body 2, various types of X-ray photography are performed while the subject M1 stands up as indicated in FIG. 1. On the other hand, in a main body 2B, a seat 423 is included as subject fixing element so that the subject M1 can sit on the seat 423. Although the detailed description is omitted, the seat 423 is connected to an elevating mechanism (not illustrated). A subject retention part 421B constituting a chin rest is attached to the seat 423. The subject retention part 421B is configured to be able to be vertically elevated and lowered. The illustration and the description of the subject-retention-part drive part MH1 that elevates the subject retention part 421B are omitted, because the subject-retention-part drive part MH1 has the device configuration similar to that of the device that drives to elevate the subject retention part 421A in FIG. 21.

In the main body 2B, when the irradiation direction of the X-ray beam is changed, the subject M1 is elevated in the axial direction of the turning shaft 31 by not vertically elevating and lowering the turning arm 30, but elevating and lowering the seat 423. Therefore, the turning arm 30 can relatively be elevated with respect to the subject M1. Preferably, a foot rest (not illustrated) on which legs of the subject (the test person) are placed or a head holder (not illustrated) that fixes the head is further provided in the seat 423.

<Fourth Modification of Apparatus Configuration>

Figure 25:
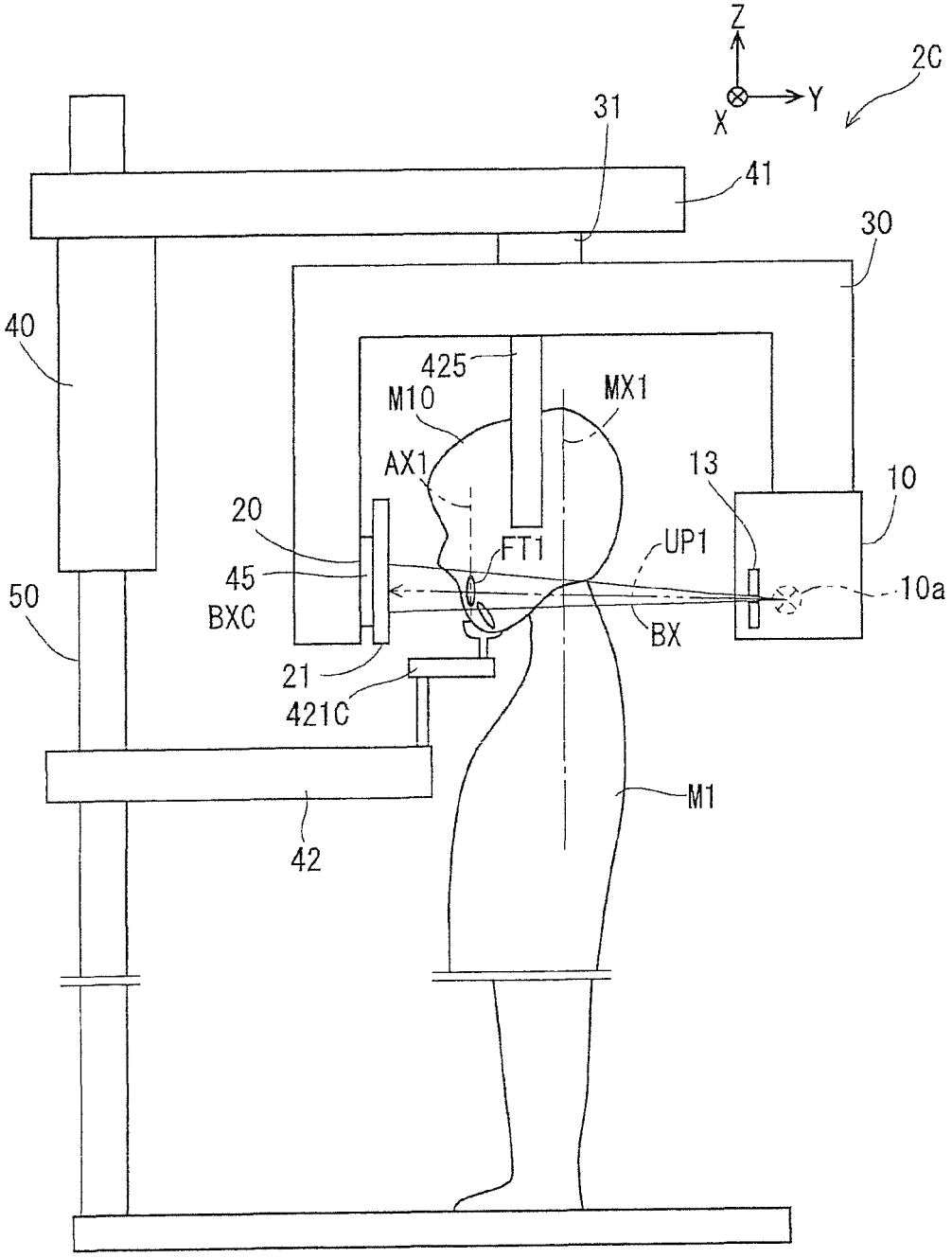
FIG. 25 is a schematic side view indicating a main body according to a fourth modification.

FIG. 25 is a schematic side view indicating a main body 2C according to a the fourth modification. The main body 2C is configured such that the head M10 of the subject M1 can be inclined forward or backward with respect to an ear rod 425 inserted in an external acoustic opening by elevating a chin rest of a subject retention part 421C. For example, as indicated in FIG. 25, the head M10 of the subject M1 can be inclined forward. Even in this mode, the irradiation direction of the X-ray beam BX to the head M10 can relatively be changed with respect to the axial direction of the body axis MX1.

<Fifth Modification of Apparatus Configuration>

In the pseudo intraoral radiography in FIGS. 15, 16, 22, 23, 24, and 25, by way of example, the X-rays UP1 and LW1 passing through the center portion of the photographing target tooth are set so as to be orthogonal to or substantially orthogonal to the tooth axis of the photographing target tooth, and the detection surface of the X-ray detector 21 is set so as to be parallel to or substantially parallel to the tooth axis AX1. Alternatively, the angles may be set to other desired angles.

Figure 26:
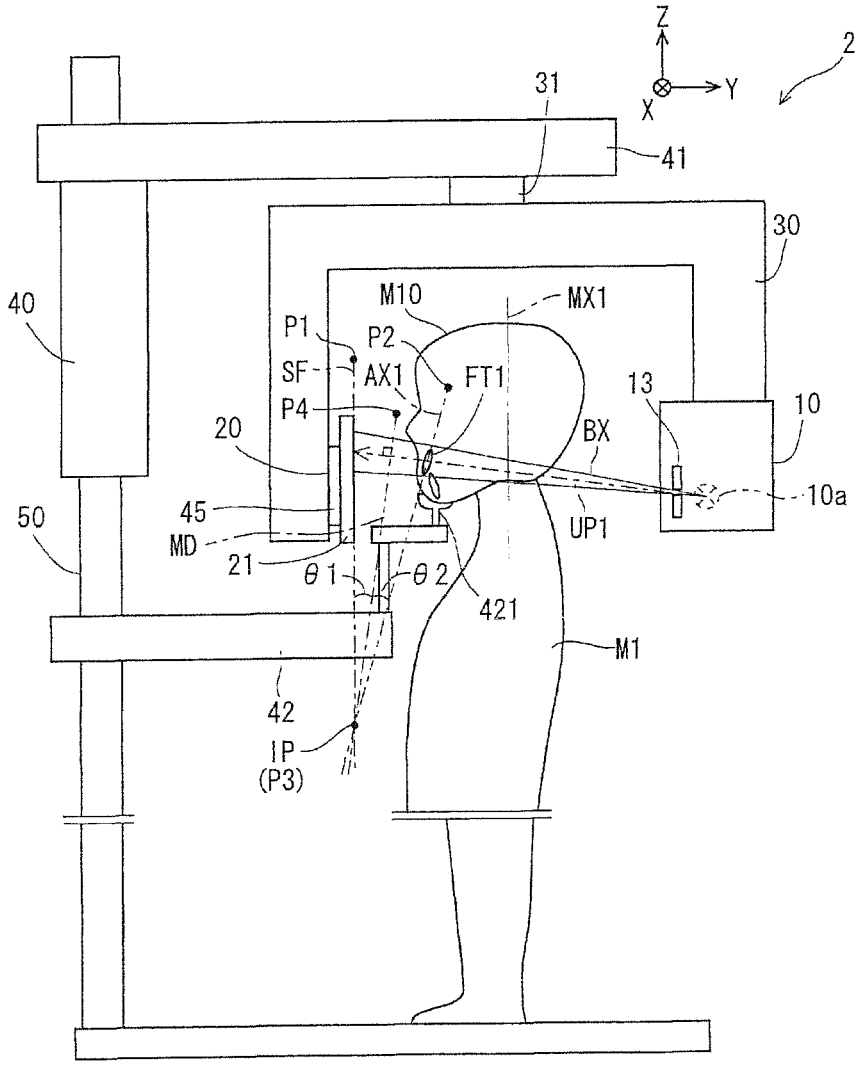
FIG. 26 is a view indicating an irradiation direction of the X-ray beam in the pseudo intraoral radiography in which the upper jaw anterior tooth is set to the photographing target.

For example, the photographing angle by the bisecting angle technique, which is adopted as well as the paralleling technique in the conventional intraoral radiography, may be set. FIG. 26 indicates an example of the angle set by the bisecting angle technique.

FIG. 26 is a view indicating the irradiation direction of the X-ray beam BX during the pseudo intraoral radiography in which the upper jaw anterior tooth FT1 is set to the photographing target. The photographing method indicated in FIG. 26 differs from the photographing method indicated in FIG. 15 in a setting point of the irradiation direction.

For the sake of convenience, it is assumed that the detection surface of the X-ray detector 21 is a surface spreading in parallel with the Z-axis direction, and that SF is a line that passes through the detection surface of the X-ray detector 21 to extend in the Z-axis direction. It is assumed that IP is an intersection point of the tooth axis AX1 and the line SF. It is assumed that the intersection point IP is indicated by a point P3, that P1 is a point located at a position different from the point P3 on the line SF, and that P2 is a point located at a position different from the point P3 on the tooth axis AX1. It is assumed that MD is a line bisecting the angle formed by the points P1, P3, and P2. Assuming that P4 is a point located at a position different from the point P3 on the line MD, an angle θ1 formed by the points P1, P3, and P4 is equal to an angle 82 formed by the points P2, P3, and P4.

In the pseudo intraoral radiography in FIG. 26, the irradiation direction of the X-ray beam BX is set with respect to the upper jaw anterior tooth FT1 such that the X-ray UP1 is orthogonal to the line MD. The X-ray UP1 may not be strictly orthogonal to the line MD, but the X-ray UP1 may substantially be orthogonal to the line MD. In the present application, the photography that simulates the intraoral radiography by the bisecting angle technique is referred to as the pseudo bisecting angle technique.

In setting the irradiation direction of the X-ray beam BX, the angles 81 and 82 may previously be determined based on the inclination of the tooth axis AX1 of a tooth of the standard skeleton, or the operator may properly input and set the angles 81 and 82. The X-ray detector 21 is properly controlled to be displaced at the position where the X-ray beam can be received.

In the case that the lower jaw anterior tooth FT2 is set to the photographing target, the description is omitted because it is the same as the case in which the upper jaw anterior tooth FT1 is set to the photographing target, except that the vertical relationship is reverse. It is clear that the photography by the pseudo bisecting angle technique can be applied to the apparatus configurations in FIGS. 16, 22, 23, 24, and 25. Therefore, the detailed description is omitted.

In the irradiation direction of the X-ray beam BX, the X-ray beam forming mechanism 13 may be controlled such that the predetermined angle is obtained in each mode, or the X-ray beam forming mechanism 13 may be controlled such that the irradiation direction of the X-ray beam BX is matched the angle designated by the operator.

<Operation Flow of X-Ray Photography Apparatus>

Figure 27:
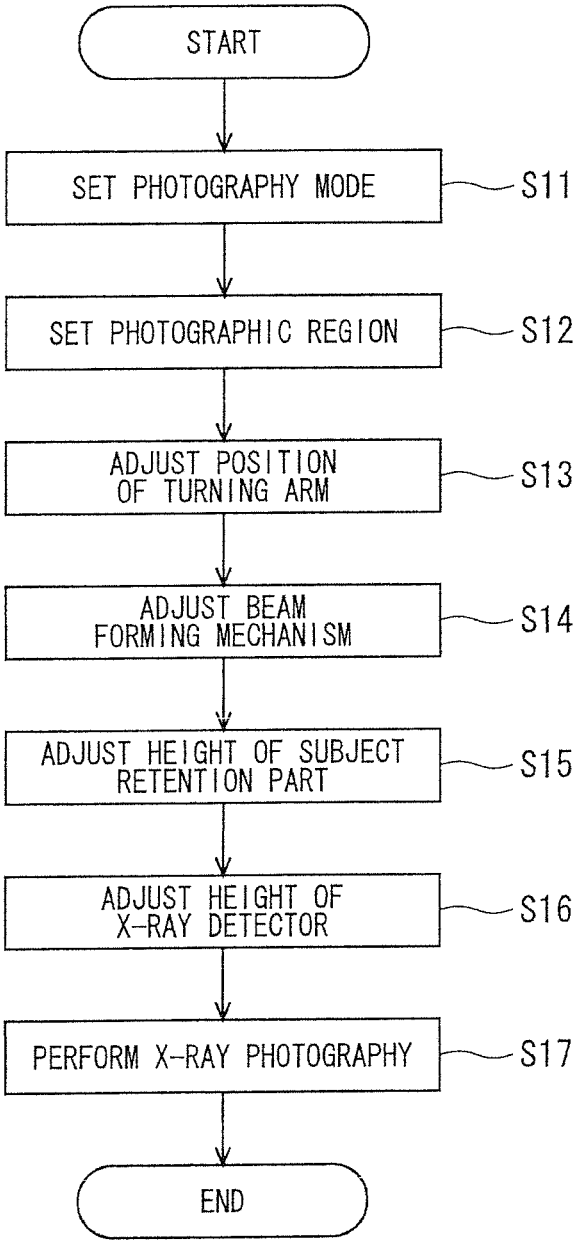
FIG. 27 is a flowchart of the X-ray photography in the X-ray photography apparatus.

FIG. 27 is a flowchart of the X-ray photography in the X-ray photography apparatus 1. The operation of the X-ray photography apparatus 1 is mainly performed under the control of the main body controller 60 unless otherwise noted.

When the X-ray photography is started, the photography mode is set (Step S11 in FIG. 27). Specifically, the photography mode selection screen MSW indicated in FIG. 11 is displayed, and the mode setter 601 selects and sets the photography mode of the main body 2 based on the manipulation input of the operator through the photography mode selection screen MSW.

Then the photographic region is designated (Step S12 in FIG. 27). Specifically, for the pseudo intraoral radiography, the upper jaw or the lower jaw and the tooth are designated (the tooth of the photographing target is designated through the photographic region setting screen 300 or a number allocated to each tooth on the region screen is designated and the like). For the panoramic photography, all the jaws including the upper jaw and the lower jaw or one of the upper jaw and the lower jaw is designated. For the CT photography, the size and the position of the photographic region are designated through the photographic region setting screen 300.

The position adjustment of the turning arm 30 is performed after the designation of the photographic region (Step S13 in FIG. 27). Specifically, the height of the turning arm 30, the horizontal two-dimensional position of the turning arm 30, or the turning starting position of the turning arm 30 is adjusted so as to fit to each photography mode and the photographic region. The adjustment of the X-ray beam forming mechanism 13 (Step S14 in FIG. 27) and the height adjustment of the subject retention part 421 (Step S15 in FIG. 27) are performed on needed basis. Therefore, the irradiation range and the irradiation direction of the X-ray beam BX and the height of the X-ray beam BX are adjusted. The height adjustment (Step S16 in FIG. 27) of the X-ray detector 21 is performed on needed basis.

When the adjustment of each component is completed, the main body 2 performs the X-ray photography (Step S17 in FIG. 27). Specifically, in the main body 2, the turning arm is turned to move the X-ray generator 10a and the X-ray detector 21 on a locus corresponding to each photography mode and the photographic region, and the X-ray generator 10a emits the X-ray beam BX having a predetermined shape. The main body 2 detects the X-ray beam BX with the X-ray detector 21, and outputs the X-ray beam BX as the frame data to the image processing device 8. Thus, the X-ray photography apparatus 1 performs various types of X-ray photography.

The X-ray photography apparatus 1 according to the preferred embodiment is configured to be able to perform the pseudo intraoral radiography, the panoramic photography, the CT photography, and the cephalic photography. However, the X-ray photography apparatus according to the present invention may be configured so to be able to perform at least one of the panoramic photography, the CT photography, and the cephalic photography together with the pseudo intraoral radiography.

<Sixth Modification of Apparatus Configuration>

Figure 28:
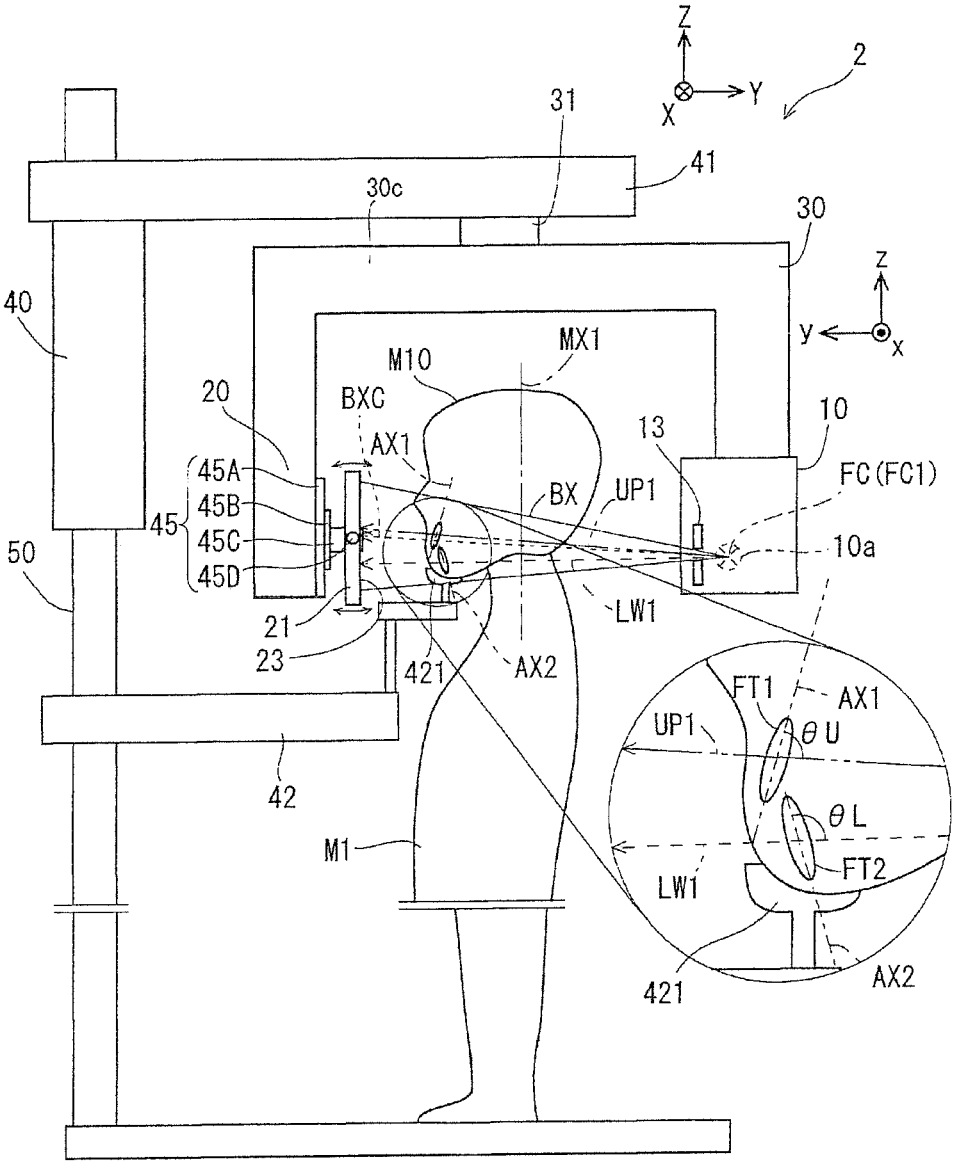
FIGS. 28 and 29 are schematic side views of a main body according to a sixth modification.
Figure 29:
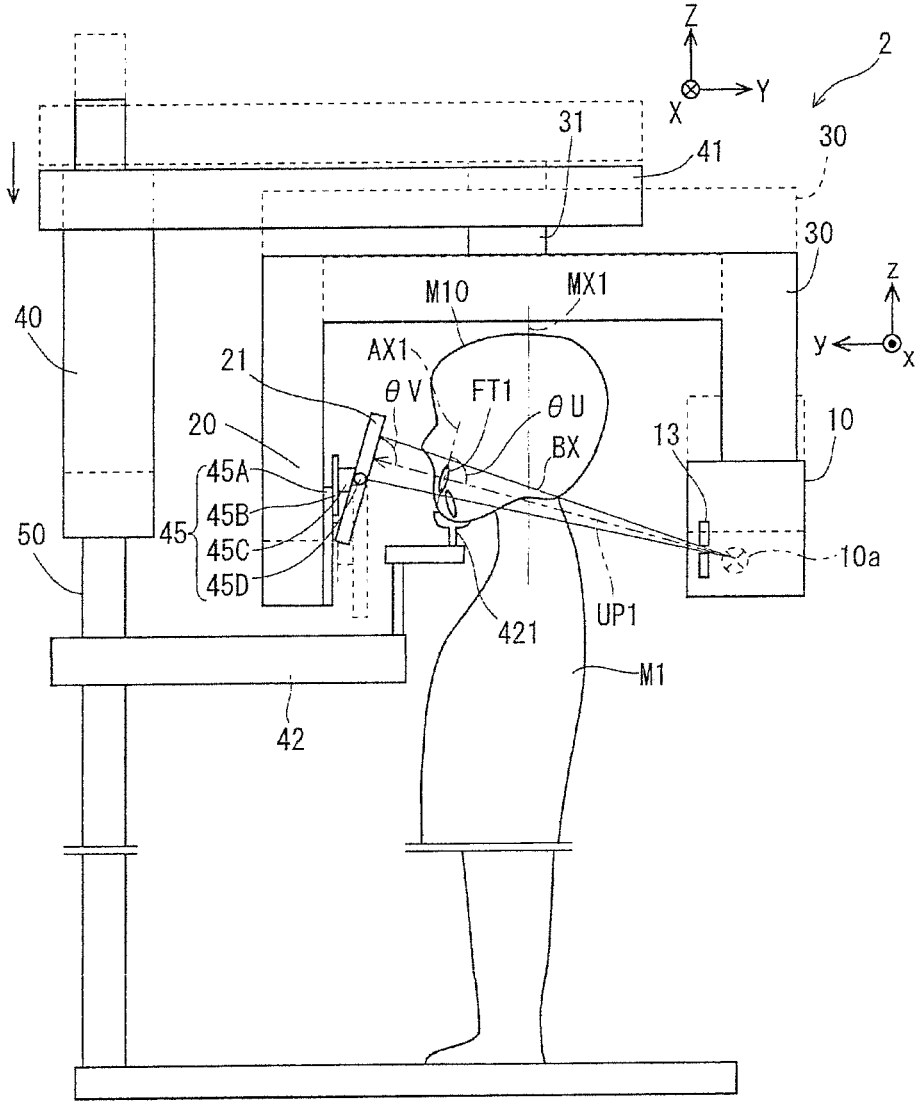

In the pseudo intraoral radiography, the X-ray detector 21 may be configured to be tilted according to the inclination of the tooth axis of the tooth that is the photographing target. FIGS. 28 and 29 illustrate a sixth modification related to the configuration. The main body 2 of the X-ray photography apparatus 1 in FIGS. 28 and 29 includes the X-ray detector drive part 45 constructed by a detector tilt mechanism. The detector tilt mechanism is described later.

The panoramic photography may be performed in the sixth modification. FIG. 28 illustrates a state in which the panoramic photography is performed with the X-ray photography apparatus 1 of the sixth modification. The detailed description is omitted, because the panoramic photography in FIG. 28 is similar to that in FIG. 14 except that the X-ray detector 21 can be tilted by the detector tilt mechanism.

<<Control of Irradiation Direction During Pseudo Intraoral Radiography>>

FIG. 29 is a view indicating the irradiation direction of the X-ray beam BX during the pseudo intraoral radiography in which the upper jaw anterior tooth FT1 is set to the photographing target. The detailed description is omitted, because control of the irradiation direction of the X-ray beam BX and the drive of the elevating part 40 are similar to those of the configuration in FIG. 15.

<Tilt Control of X-Ray Detector 21>

In the sixth modification, the detection surface of the X-ray detector is controlled so as to be parallel or substantially parallel to the tooth axis AX1. In the present application, the pseudo intraoral radiography that simulates the paralleling technique of the intraoral radiography is also referred to as a pseudo paralleling technique. The setting of the irradiation direction of the X-ray beam BX is previously determined based on the inclination of the tooth axis AX1 of the tooth of the standard skeleton. Alternatively, the operator may manually input the setting of the irradiation direction of the X-ray beam BX.

Figure 38:
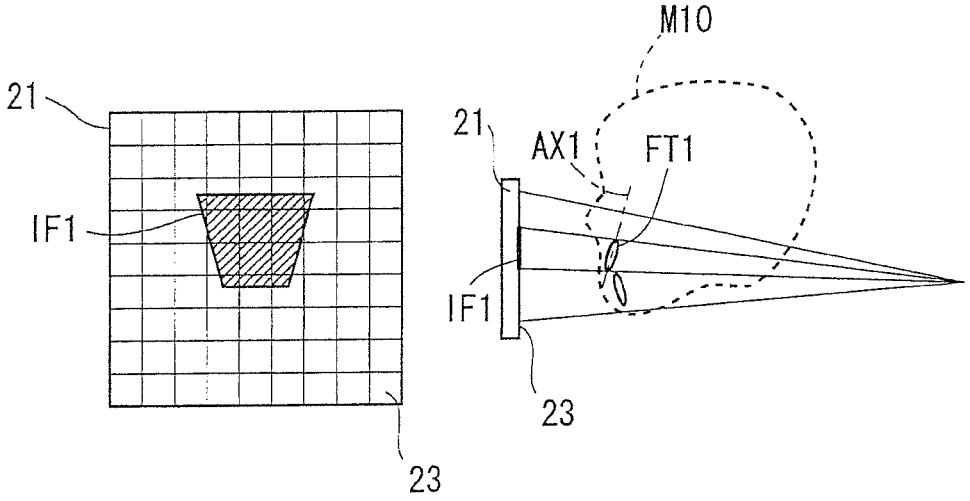
FIG. 38 is a view indicating a distortion of a projection image of a photographing target object.

In the X-ray image (the projection image) of the upper jaw anterior tooth FT1, which is obtained by the X-ray detector 21 in performing the pseudo intraoral radiography of the upper jaw anterior tooth FT1, the upper portion (the tooth root portion side) is distant from the detection surface 23 of the X-ray detector 21, and the lower portion (the tooth crown portion side) is close to the detection surface 23 of the X-ray detector 21. Therefore, in the case that the detection surface 23 is disposed in parallel to the Z-axis direction, a distortion caused by a difference in magnification rate is generated in the projection image of the upper jaw anterior tooth FT1 as indicated in FIG. 38. Referring to FIG. 38, if the photographic region where the upper jaw anterior tooth FT1 is set to the photographing target has a rectangular shape when viewed from the X-ray irradiation direction, a projection image IF1 received by the detection surface 23 becomes a distorted image, in which an upper side is longer than a lower side, when viewed from the front side. In this case, it is necessary to remove the distortion by correction of image processing (what is called keystone correction). On the other hand, the medical X-ray photography apparatus 1 of the sixth modification includes the tilt mechanism that tilts the detection surface 23 of the X-ray detector 21. The distortion of the projection image can largely reduced with the tilt mechanism. The configuration of the tilt mechanism will be described.

As indicated in FIGS. 28 and 29, the X-ray detector drive part 45 includes a drive part base 45A, an X-ray detector elevating part 45B, a shaft supporting part 45C and a rotational shaft 45D. The drive part base 45A is fixed to the base of the X-ray detection part 20 in the support 30. The X-ray detector elevating part 45B is driven to be elevated in the Z-axis direction (the z-axis direction) with respect to the drive part base 45A. The shaft supporting part 45C is fixed to the X-ray detector elevating part 45B. The rotational shaft 45D is engaged with the shaft supporting part 45C to become a shaft for the rotation of the X-ray detector 21. Therefore, the rotational shaft 45D also acts as an X-ray detector rotational axis.

The axial direction of the rotational shaft 45D is orthogonal to turning shaft 31, preferably the axial direction of the rotational shaft 45D is the x-axis direction. In the example in FIGS. 28 and 29, the rotational shaft 45D pierces the X-ray detector 21 along the x-axis direction, at a central portion of the X-ray detector 21 in the Z-axis direction. The rotational shaft 45D is supported by the shaft supporting part 45C at a position on one side (in this case, the +x-side) of the X-ray detector 21. Alternatively, the shaft supporting part 45C may be provided on each side (the +x-side and the −x-side) of the X-ray detector 21, and the rotational shaft 45D may be supported at positions on both the sides of the X-ray detector 21.

Figure 30:
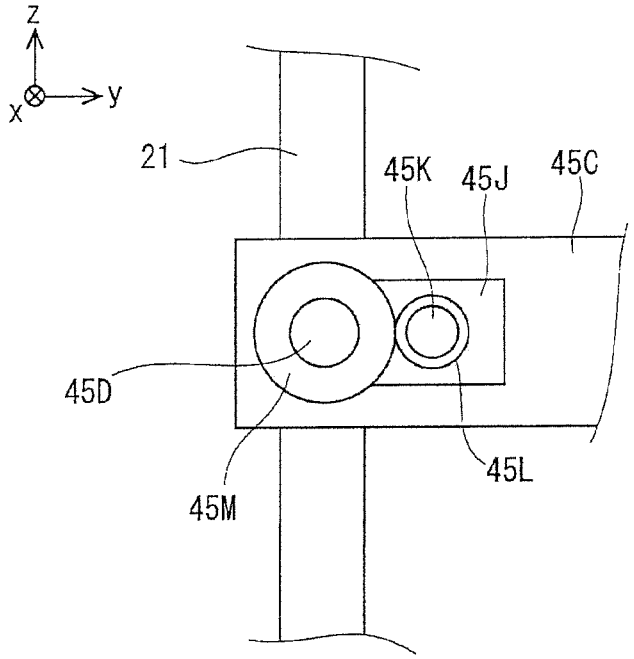
FIG. 30 is a view indicating a mechanical configuration of an X-ray detector drive part.

FIG. 30 is a view indicating a mechanical configuration of the X-ray detector drive part 45. FIG. 30 is the view when the X-ray detector 21 is viewed from the side (that is, the +x-side) on which the shaft supporting part 45C is provided. The X-ray detector 21 is rotated and tilted about the rotational shaft 45D by a rotation actuator (the detector tilt mechanism). The rotation actuator is constructed by a motor 45J, a rotary drive shaft 45K, and rollers 45L and 45M as indicated in FIG. 30.

The rotational shaft 45D is fixed to the X-ray detector 21, and rotatably supported by the shaft supporting part 45C. The motor 45J is fixed to the shaft supporting part 45C. The roller 45L is fixed around the leading end of the rotary drive shaft 45K of the motor 45J.

The roller 45M is fixed to an end portion of the rotational shaft 45D. The roller 45L and the roller 45M are disposed so as to abut on each other, and a driving force of the motor 45J is transmitted to the rotational shaft 45D. A gear may be used instead of the roller 45L.

Although not indicated, for example, an elevating actuator that drives to elevate and lower the X-ray detector elevating part 45B is configured as follows. A screw shaft and a position adjustment motor, which are similar to the screw shaft 161a and the position adjustment motor 162a in FIG. 4, are fixed to the drive part base 45A. A nut similar to the nut 141 in FIG. 4 is fixed to the X-ray detector elevating part 45B. The screw shaft rotates normally or reversely by the drive of the position adjustment motor to vertically move the nut member, which allows the X-ray detector elevating part 45B to be elevated.

Tilt control (rotation control) of the X-ray detector 21 by the X-ray detector drive part 45 will be described below.

The X-ray detector 21 in FIG. 29 is elevated in the +Z-direction by the X-ray detector elevating part 45B. The X-ray detector 21 is inclined while rotated about the rotational shaft 45D by the rotation actuator. Specifically, the upper (the +z side) portion of the X-ray detector 21 is inclined so as to collapse on the side of the X-ray generator 10a.

More specifically, the inclination of the X-ray detector 21 is controlled such that the X-ray UP1 is orthogonally incident to the detection surface of the X-ray detector 21 as indicated in FIG. 29. However, an incident angle θV of the X-ray UP1 does not need to be strictly orthogonal to the detection surface of the X-ray detector 21, but the incident angle θV may substantially be orthogonal to the detection surface of the X-ray detector 21 like an irradiation angle θU of the X-ray UP1 with respect to the tooth axis AX1. A detection surface of the X-ray detector 21 is controlled so as to be parallel or substantially parallel to the tooth axis AX1.

The X-ray detector drive control part 603 controls the inclination of the X-ray detector 21, which is driven by the X-ray detector drive part 45, according to the photographic region being set.

The detailed description is omitted for the case that the lower jaw anterior tooth FT2 is set to the photographing target, because this case differs from the case that the upper jaw anterior tooth FT1 is set to the photographing target only in that the image is formed upside down.

In the sixth modification, by way of example, the X-ray detector 21 is tilted using the rotation actuator and the X-ray detector elevating part 45B is elevated using the elevating actuator. Alternatively, the X-ray detector 21 and/or the X-ray detector elevating part 45B may be configured to be manually driven. In this case, for example, displacement or latching action of an extent that the manual manipulation is received may be exerted by providing a mechanism of action such as friction, biasing, and fitting between members that are displaced relative to each other according to the tilt or elevating operation.

The X-ray detector drive part 45 may control the tilt control of the X-ray detector 21 during the panoramic photography. For example, in the case that the panoramic photography in which the whole jaw (including the upper jaw and the lower jaw) is set to the photographing target is performed, the projection image in which the distortion is reduced can be obtained with respect to the upper jaw anterior tooth FT1 or the lower jaw anterior tooth FT2 by tilting the X-ray detector 21 according to one of the inclinations of the tooth axis AX1 of the upper jaw anterior tooth FT1 and the tooth axis AX2 of the lower jaw anterior tooth FT2.

As indicated in FIG. 28, during the panoramic photography, the vertically extending direction of the detection surface 23 of the X-ray detector 21 may be matched with the z-axis direction similarly to the detection surface of the X-ray detector 21 in FIG. 14. In other words, the setting may be performed with no inclination. Because the panoramic image which is photographed while the vertically extending direction of the detection surface of the X-ray detector 21 is matched with the z-axis direction is a panoramic image familiar to the conventional practitioner, the panoramic photography performed by setting the X-ray detector 21 to the angle in FIG. 28 has a technical meaning that the panoramic image familiar to the conventional practitioner can be generated.

It is conceivable that the inclination angle of the detection surface 23 of the X-ray detector 21 is fixed during the panoramic photography. Alternatively, the inclination angle of the X-ray detector 21 may properly be changed according to the tooth irradiated with the X-ray beam BX during the panoramic photography. For example, It is conceivable that the X-ray detector 21 is tilted such that the detection surface 23 becomes substantially perpendicular to the horizontal plane (the XY plane) when a molar tooth is irradiated with the X-ray, and the X-ray detector 21 is tilted such that the detection surface 23 of the X-ray detector 21 becomes parallel to the tooth axis AX1 (or the tooth axis AX2) when the upper jaw anterior tooth FT1 (or the lower jaw anterior tooth FT2) is irradiated with the X-ray. The configuration may be made such that whether the detection surface 23 is set parallel to the tooth axis AX1 or the tooth axis AX2 can be selected depending on, for example, which one of the upper jaw anterior tooth FT1 and the lower jaw anterior tooth FT2 has to be placed a medical emphasis on. Thus, the tilt of the X-ray detector 21 is controlled such that the detection surface 23 becomes parallel to the tooth axis of each tooth, which allows the projection image in which the distortion is reduced to be obtained with respect to each tooth. Therefore, the panoramic X-ray image having high image quality can be obtained while an arithmetic processing amount for the correction is further reduced.

It is also conceivable that the tilt of the X-ray detector 21 is controlled in the panoramic photography in which not the whole jaw but only the upper jaw or the lower jaw is set to the photographing target. For example, the detection surface 23 is set so as to be parallel to the tooth axis AX1 for the anterior tooth portion in the case that only the upper jaw is photographed, and the detection surface 23 is set so as to be parallel to the tooth axis AX2 for the anterior tooth portion in the case that only the lower jaw is photographed. Even in these cases, the inclination angle of the X-ray detector 21 may be changed according to the tooth irradiated with the X-ray beam BX during the panoramic photography. In this case, the projection image in which the distortion is reduced can be obtained for each tooth.

In the case that the panoramic photography is performed to part of the upper jaw or part of the lower jaw, it is conceivable that the tilt of the X-ray detector 21 is controlled such that the detection surface 23 becomes parallel to the tooth axis of the tooth included in the photographing target.

In the case of the panorama of the whole jaw, or in the case of the wide photographic region even in the partial panorama, the irradiation direction of the X-ray beam BX may continuously be changed during the panoramic photography while the change in inclination angle of the X-ray detector 21 is controlled. In the case of the narrow photographic region in the partial panorama, the inclination angle of the X-ray detector 21 and the irradiation direction of the X-ray beam BX may be kept constant.

A height of the turning arm 31 is kept constant irrespective of the photographic region, and only the change may be performed such that the direction of the tooth axis of each teeth and the inclination angle of the X-ray detector 21 are matched each other. In this case, for example, the irradiation range of the X-ray beam is restricted by the X-ray beam forming mechanism 13 at the height of the turning arm in FIG. 28, and only the inclination angle of the X-ray detector 21 is changed according to the direction of the tooth axis of the target tooth.

<Seventh Modification of Apparatus Configuration>

Figure 31:
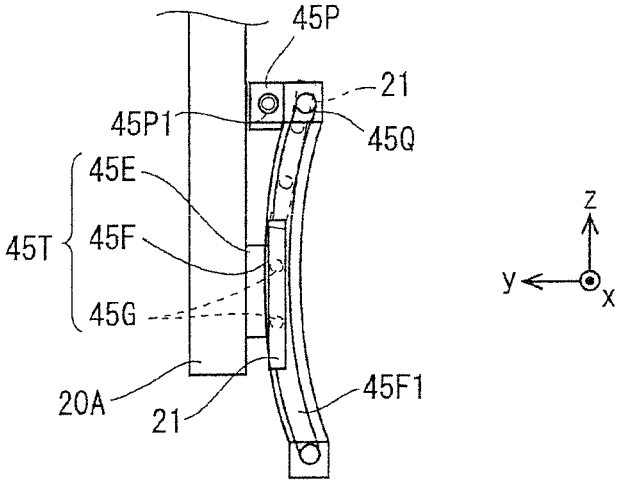
FIGS. 31 and 32 are views indicating an X-ray detector drive part according to a seventh modification.
Figure 32:
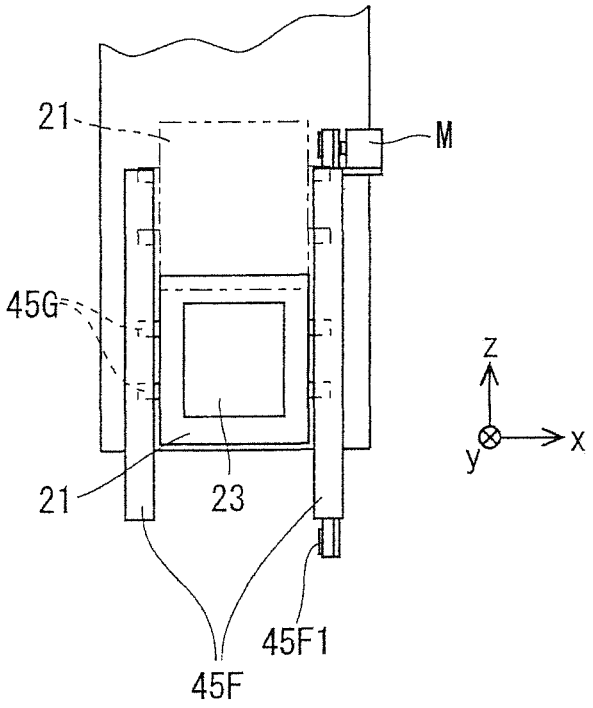

FIGS. 31 and 32 are views indicating an X-ray detector drive part 45T according to a seventh modification obtained by further modifying the sixth modification. FIG. 31 is a side view when the X-ray detection part 20 is viewed from the left side (that is, the +x-side) with respect to the X-ray detector 21. FIG. 32 is a front view when the X-ray detector 21 is viewed from the front side.

The X-ray detector drive part 45 in FIGS. 28 to 30 rotates the X-ray detector 21 with the rotational shaft 45D as the rotational axis, and vertically elevates and lowers the X-ray detector 21 using the X-ray detector elevating part 45B. On the other hand, the X-ray detector drive part 45T in FIG. 31 includes an X-ray detector guide part 45F instead of the rotational shaft 45D and the X-ray detector elevating part 45B.

More particularly, the X-ray detector drive part 45T includes an X-ray detector retention part 45E that is fixed to an X-ray detection part base 20A, an X-ray detector guide part 45F that is provided in the X-ray detector retention part 45E, and a plurality of guided parts 45G that are guided by the X-ray detector guide part 45F. The guided part 45G includes a roller and the like, and is fixed to both end portions of the X-ray detector 21.

The X-ray detector guide part 45F is disposed on each of both the sides (the +x-side and the −x-side) of the X-ray detector 21. For the sake of convenience, the X-ray detector guide part 45F located on the left side (that is, the −x-side) of the X-ray detector 21 is omitted in FIG. 31.

In the pair of X-ray detector guide parts 45F, an arc-shape groove part 45F1 extending along the X-ray detector guide part 45F is formed in the side portion opposed to the X-ray detector 21. The groove part 45F1 is curved in the −y-direction from the central portion of the Z-axis direction toward the +Z-direction and the −Z-direction. The guided part 45G is fitted in the curved groove part 45F1.

A motor 45P is provided in the upper portion of one of the pair of X-ray detector guide parts 45F. In the example in FIGS. 31 and 32, the motor 45P is provided in the X-ray detector guide part 45F on the +x-side of the X-ray detector 21. A rotary drive transmission shaft 45P1 of the motor 45P abuts on an inner circumferential portion on one side of an annular belt 45Q. The annular belt 45Q is disposed inside the X-ray detector guide part 45F. The portion on the other side of the annular belt 45Q is wound around an outer circumferential portion of the freely rotating roller disposed on the lower side of the X-ray detector guide part 45F. Therefore, the annular belt 45Q rotates in the X-ray detector guide part 45F by the rotation of the rotary drive transmission shaft 45P1.

The guided part 45G, which is attached to the X-ray detector guide part 45F in which the annular belt 45Q is provided, is fixed to the annular belt 45Q. Therefore, the X-ray detector 21 is vertically elevated by the rotation of the annular belt 45Q.

In the case that the X-ray detector 21 is located in the central portion in the vertical direction of the X-ray detector guide part 45F, the detection surface 23 of the X-ray detector 21 is parallel to the turning shaft 31, and is substantially perpendicular to the horizontal plane. When the X-ray detector 21 is elevated from the central portion of the X-ray detector guide part 45F, the guided part 45G is guided by the X-ray detector guide part 45F. Therefore, as indicated by an alternate long and short dash line in FIG. 31, the X-ray detector 21 is inclined with increasing height of the X-ray detector 21, and the detection surface 23 of the X-ray detector 21 is also inclined.

Although not shown, the inclination of the X-ray detector 21 is set such that the X-ray UP1 is orthogonally incident to the detection surface of the X-ray detector 21. However, the incident angle θV of the X-ray UP1 does not need to be strictly orthogonal to the detection surface 23 of the X-ray detector 21, but the incident angle θV may substantially be orthogonal to the detection surface 23 of the X-ray detector 21 like the irradiation angle θU of the X-ray UP1 with respect to the tooth axis AX1.

The detailed description is omitted for the case that the X-ray detector 21 is lowered, because this case differs from the case that the X-ray detector 21 is elevated only in that the positional relationship of the X-ray detector 21 becomes upside down.

Such the physical rotational shaft as the rotational shaft 45D does not exist for the X-ray detector drive part 45T. However, it can be understood that the X-ray detector drive part 45T rotates the X-ray detector 21 about a virtual rotational axis which is parallel to the x-axis direction and passes through the center of a circle of curvature in which the arc-shape groove part 45F1 is included as part of the arc. It can be understood that, when attention is paid only to the tilt of the X-ray detector 21 while a sight line is fixed on any point of side surface of the X-ray detector 21 viewed from the x-axis direction, the point is the virtual rotational axis parallel to the x-axis direction, and that the X-ray detector 21 is rotated about the point.

In the example in FIG. 31, the X-ray detector 21 is driven using the motor 45P. Alternatively, as indicated in FIGS. 28 to 30, the X-ray detector 21 may manually be driven by providing the mechanism of action such as friction, biasing, the fitting.

Basically, when the tooth is observed toward the cheek side from the tongue side (the inside of the mouth cavity), or when the tooth is observed in the opposite direction, a sight line direction is desirably orthogonal to the tooth axis. The X-ray image in which the tooth is obliquely looked down on or the X-ray image in which the tooth is obliquely looked up at is acquired unless the center axis of the X-ray beam BX is orthogonal to the tooth of the photographing target. In this case, the image in which the tooth is looked shorter than the real size is obtained. Accordingly, the faithful image of the shape of the tooth can be acquired with the small distortion by causing the center axis of the X-ray beam to orthogonally incident on the target tooth (that is, the center axis of the X-ray beam BX is orthogonal to the tooth axis).

The case that the lower jaw is set to the photographing target is similar to the case that the upper jaw is set to the photographing target in that the irradiation direction of the X-ray beam BX is varied with respect to the axial direction of the body axis MX1 according to the position of the pseudo intraoral radiography region. In other words, the irradiation angle of the X-ray beam BX with respect to the Z-axis direction, the irradiation range, the position of the turning arm 30, and the turning angle of the turning arm 30 vary in each of the photographic regions of the photographing targets such as the whole jaw, part of the jaw, the tooth of the upper jaw, the tooth of the lower jaw, the tooth in a certain region of the upper jaw, and the tooth in a certain region of the lower jaw. Therefore, in each photographic region, there are properly performed the elevating control of the elevating part 40 by the support drive controller 602, the position control of the turning arm 30 by the moving mechanism 200, the drive control of the X-ray beam forming mechanism 13 by the X-ray-regulating-part drive part 101 based on the control of the X-ray-regulating-part drive controller 605, and the position control of the X-ray detector 21 by the X-ray detector drive part 45 based on the control of the X-ray-detector drive controller 603. In the case that the subject-retention-part drive part MH1 needs to drive the subject retention part 421, the subject-retention-part drive part MH1 is properly controlled based on the control of a subject-retention-part drive controller 604.

<<Control of Irradiation Direction During CT Photography>>

Figure 33:
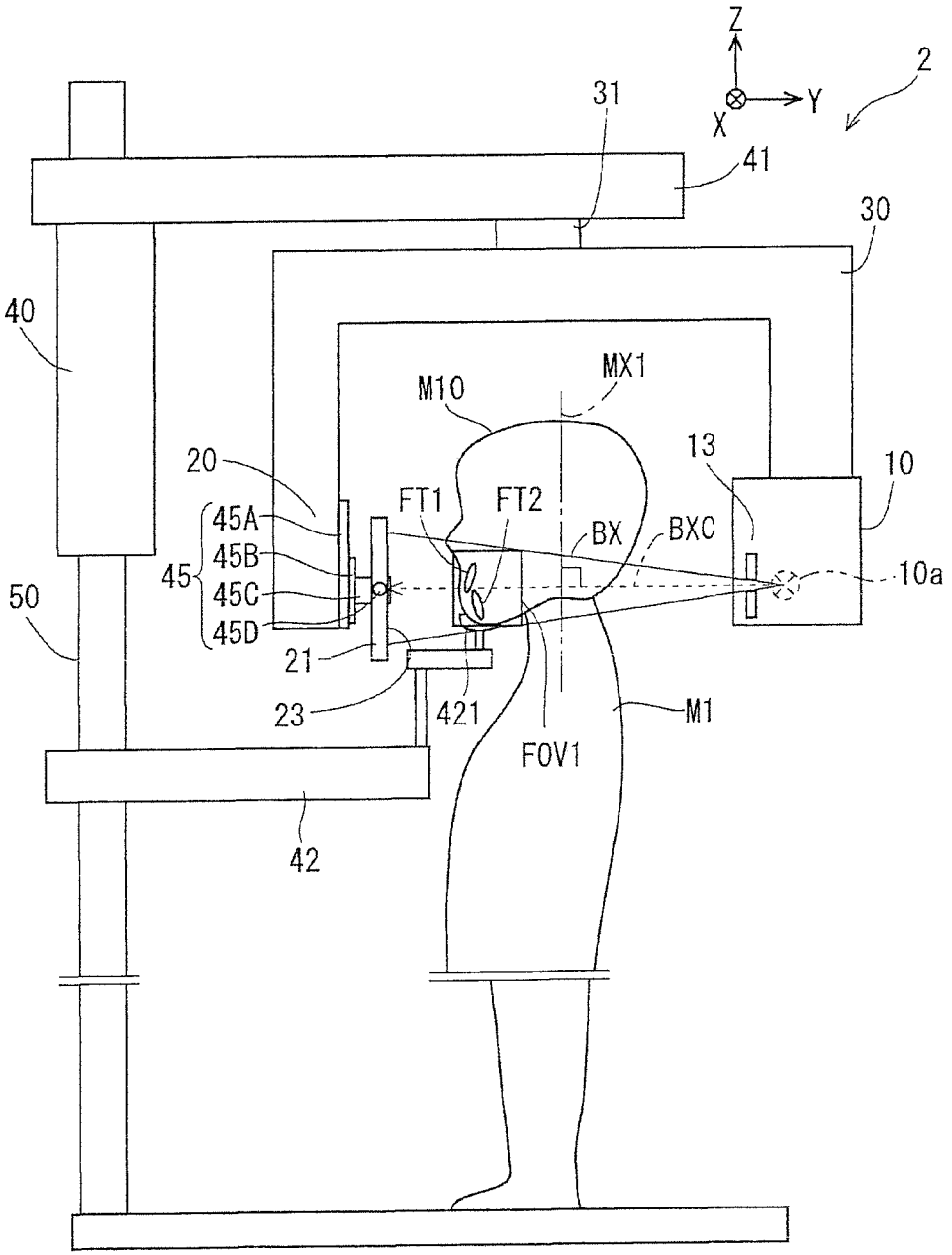
FIG. 33 is a view indicating the CT photography in which the upper jaw and the lower jaw are set to the photographing target.

FIG. 33, similarly to FIG. 17, is a view indicating the CT photography in which the upper jaw and the lower jaw are set to the photographing target. Because the size of the FOV and the irradiation direction of the X-ray beam BX are similar to those in FIG. 17, the description is omitted. As to the setting of the tilt angle of the X-ray detector 21, by the action of the X-ray detector drive part 45, the elevating operation of the X-ray detector 21 is controlled to the position where the detection surface can detect the whole X-ray beam BX, and the tilt angle of the X-ray detector 21 is set to the angle at which the center axis BXC of the X-ray beam BX is orthogonally incident to the detection surface. In the example in FIG. 33, the vertically extending direction of the detection surface 23 of the X-ray detector 21 is matched with the z-axis direction. In other words, the setting is performed with no inclination. The orthogonal incidence is one with respect to at least the z-axis direction, more preferably one with respect to the x-axis direction. The center axis BXC does not need to be strictly orthogonal to the detection surface, but the center axis BXC may substantially be orthogonal to the detection surface.

Figure 34:
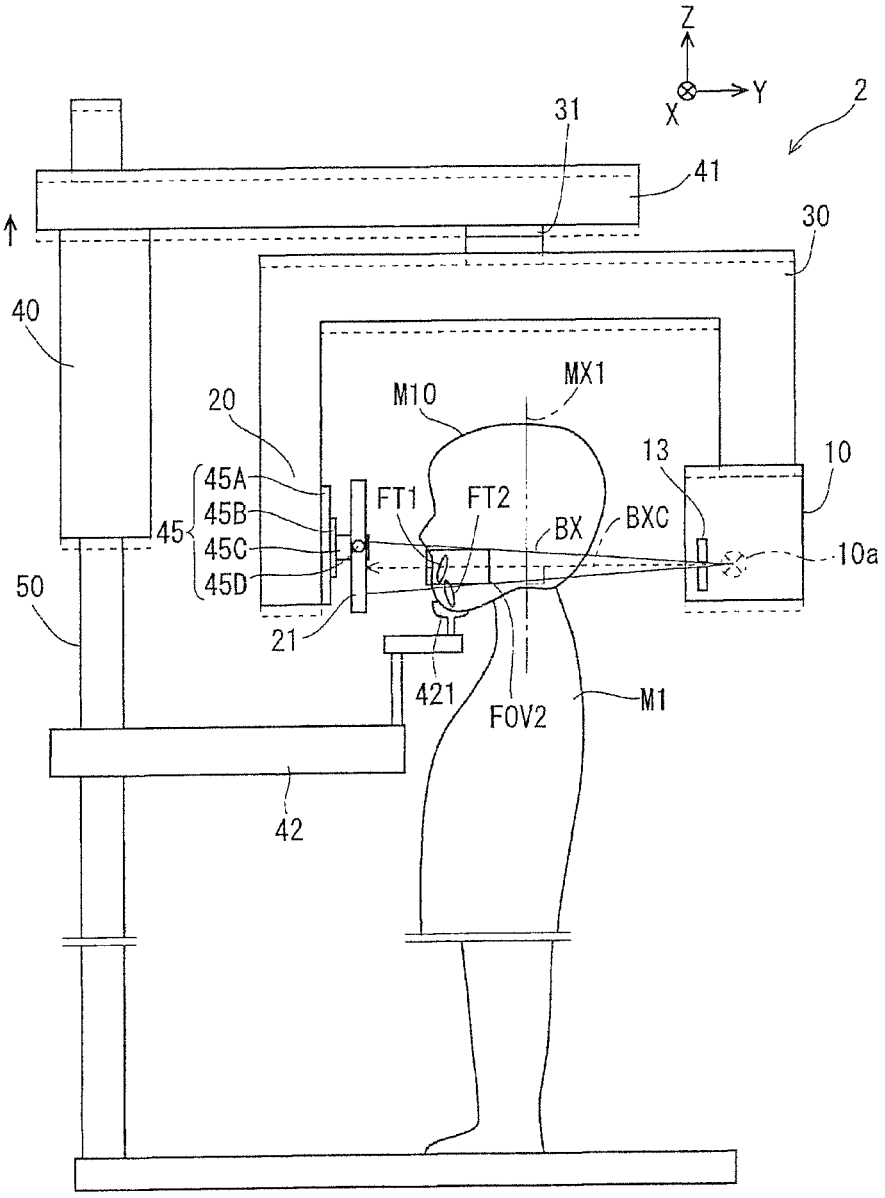
FIG. 34 is a view indicating the CT photography in which the upper jaw is set to the photographing target.
Figure 35:
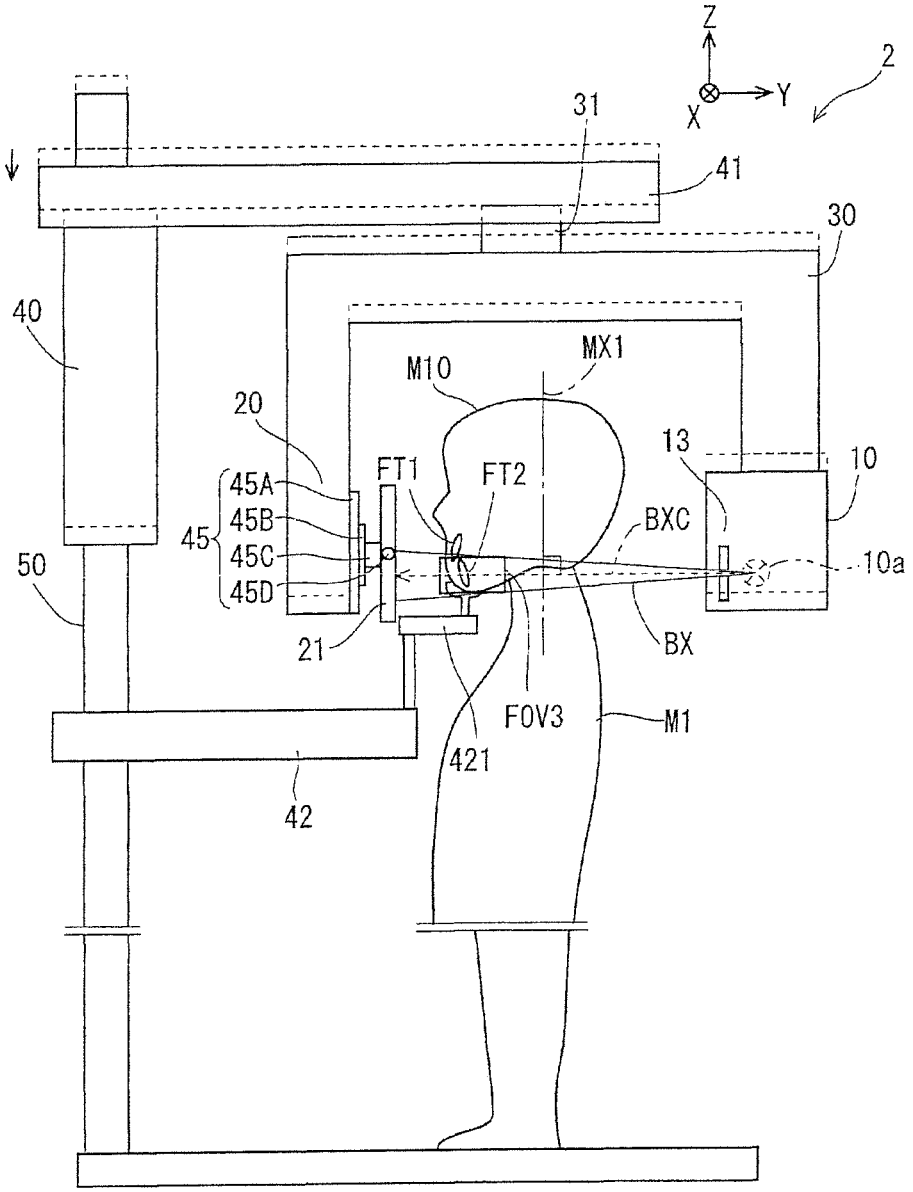
FIG. 35 is a view indicating the CT photography in which the lower jaw is set to the photographing target.

FIG. 34, similarly to FIG. 18, is a view indicating the CT photography in which the upper jaw is set to the photographing target. FIG. 35, similarly to FIG. 19, is a view indicating the CT photography in which the lower jaw is set to the photographing target. Because the size of the FOV and the irradiation direction of the X-ray beam BX are similar to those in FIGS. 18 and 19, the description is omitted. By the action of the X-ray detector drive part 45, the elevating operation of the X-ray detector 21 is controlled to the position where the detection surface can detect the whole X-ray beam BX, and the tilt angle of the X-ray detector 21 is set to the angle at which the center axis BXC of the X-ray beam BX is orthogonally incident to the detection surface. The orthogonal incidence is one with respect to at least the z-axis direction, more preferably one with respect to the x-axis direction. In the example in FIGS. 34 and 35, the vertically extending direction of the detection surface 23 of the X-ray detector 21 is matched with the z-axis direction. The center axis BXC does not need to be strictly orthogonal to the detection surface, but the center axis BXC may substantially be orthogonal to the detection surface.

Similarly to the example in FIGS. 17 to 19, it is conceivable that the photographic region is irradiated with the X-ray beam BX during the CT photography while the irradiation direction of the X-ray beam BX is not horizontal but inclined upward (or downward). In the case that the irradiation direction of the X-ray beam BX is inclined, the X-ray detector 21 may be tilted such that the detection surface 23 of the X-ray detector 21 is orthogonal to the irradiation direction of the X-ray beam BX, which allows the projection image in which the distortion is reduced to be obtained.

<Eighth Modification of Apparatus Configuration>

In the main body 2 of the sixth modification, because the X-ray detector 21 has the relatively small detection surface, the X-ray detector 21 is vertically elevated by the X-ray detector drive part 45 to detect the X-ray beam BX. Alternatively, although not shown, the X-ray detector elevating part 45B can be eliminated using the X-ray detector having the sufficiently wide detection surface that need not to be vertically elevated by the X-ray detector elevating part 45B of the X-ray detector drive part 45.

In the sixth to eighth modifications, similarly to the third modification, a seat 423 may be used as the subject fixing means. In the sixth to eighth modifications, similarly to the fourth modification, the head M10 of the subject M1 may be inclined forward or backward with respect to the ear rod 425 inserted in the external acoustic opening by elevating the chin rest of the subject retention part 421C.

Figure 36:
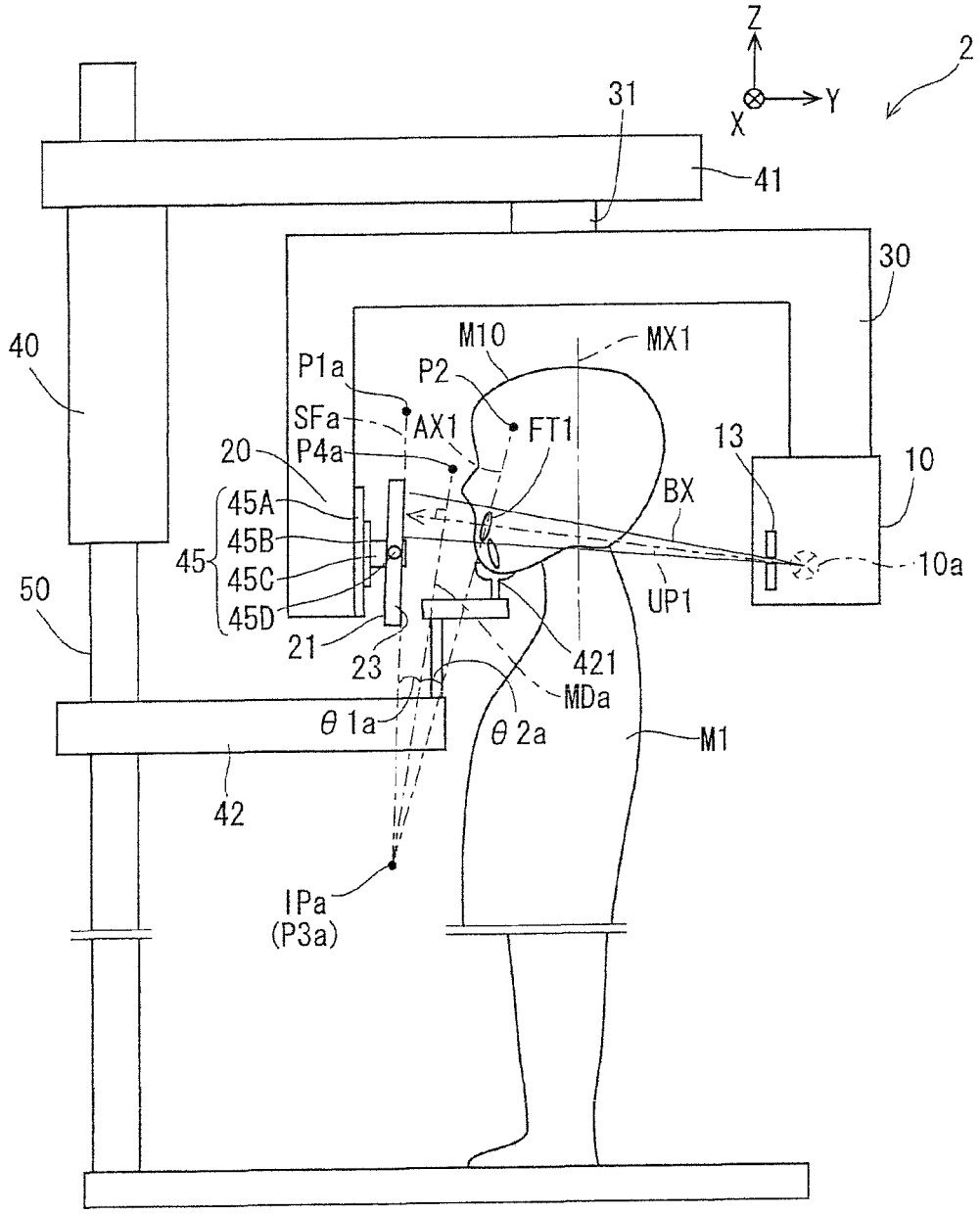
FIG. 36 is a view indicating the irradiation direction of the X-ray beam and a tilt of an X-ray detector during the pseudo intraoral radiography in which the upper jaw anterior tooth is set to the photographing target.

In the sixth to eighth modifications, the photographing angle may be set similarly to the setting by the pseudo bisecting angle technique. FIG. 36 indicates setting example.

FIG. 36 is a view indicating the irradiation direction of the X-ray beam BX and the tilt of the X-ray detector 21 during the pseudo intraoral radiography in which the upper jaw anterior tooth FT1 is set to the photographing target. The photographing method in FIG. 36 differs from the photographing method in FIG. 29 in the method for setting the irradiation direction and the method for setting the inclination angle of the X-ray detector 21.

For the sake of convenience, it is assumed that a line SFa extends or substantially extends in the Z-axis direction and along the detection surface 23 of the X-ray detector 21. A point IPa is an intersection of the tooth axis AX1 and the line SFa. Assuming that the intersection point IPa is indicated by a point P3a, a point P1a is located at the position different from the point P3a on the line SFa, and a point P2 is located at the position different from the point P3a on the tooth axis AX1. A line MDa equally divides an angle formed by the points P1a, P3a, and P2. Assuming that a point P4a is located at the position different from the point P3a on the line MDa, an angle θ1a formed by the points P1a, P3a, and P4a is equal to an angle θ2a formed by the points P2, P3a, and P4a.

In the pseudo intraoral radiography in FIG. 36, the irradiation direction of the X-ray beam BX is set with respect to the upper jaw anterior tooth FT1 such that the X-ray UP1 is orthogonal to the line MDa. The X-ray UP1 does not need to be strictly orthogonal to the line MD, but the X-ray UP1 may substantially be orthogonal to the line MD. The configuration in FIG. 36 is also an example of the pseudo bisecting angle technique.

In setting of the irradiation direction of the X-ray beam BX, the angles θ1a and θ2a may previously be set based on the inclination of the tooth axis AX1 of the tooth of the standard skeleton, or the operator may input and set properly the angles θ1a and θ2a. The X-ray detector 21 is properly controlled to be displaced at the position where the X-ray beam can be received.

For the case that the lower jaw anterior tooth FT2 is set to the photographing target, the description is omitted because a vertical relationship of the case that upper jaw anterior tooth FT1 is set to the photographing target is reversed.

<Operating Flow of Medical X-Ray Photography Apparatus>

Figure 37:
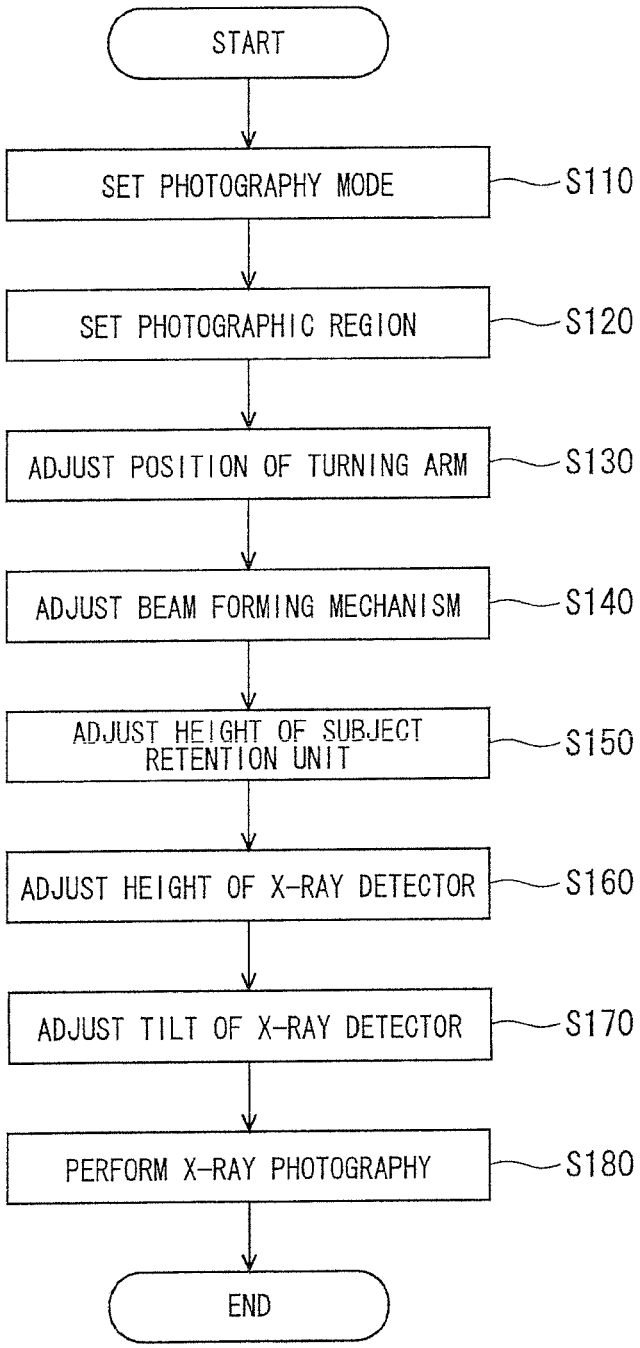
FIG. 37 is a flowchart of X-ray photography in a medical X-ray photography apparatus according to the sixth to eighth modifications.

FIG. 37 is a flowchart of the X-ray photography in the medical X-ray photography apparatus 1 according to the sixth to eighth modifications.

In the flowchart in FIG. 37, the photography mode is set (Step S110) similarly to Step S11 in FIG. 27. The photographic region is set (Step S120) similarly to Step S12 in FIG. 27. The position of the turning arm 30 is adjusted (Step S130) similarly to Step S13 in FIG. 27. The X-ray beam forming mechanism 13 is adjusted (Step S140) similarly to Step S14 in FIG. 27. The height of the subject retention part 421 is adjusted (Step S150) similarly to Step S15 in FIG. 27. As needed basis, the height of the X-ray detector 21 is adjusted (Step S160) similarly to Step S16 in FIG. 27. As needed basis, the inclination angle of the X-ray detector 21 is adjusted (Step S170) under the control of the tilt mechanism.

When the adjustment of each component is completed, the main body 2 performs the X-ray photography (Step S180 in FIG. 37). Specifically, in the main body 2, the turning arm 30 is turned to move the X-ray generator 10a and the X-ray detector 21 on the locus corresponding to the photography mode and the photographic region under the control of the moving mechanism 200 including the turning part 201, and the X-ray generator 10a emits the X-ray beam BX having the required shape. The main body 2 detects the X-ray beam BX with the X-ray detector 21, and outputs the X-ray beam BX as the frame data to the image processing device 8. Thus, the medical X-ray photography apparatus 1 performs various kinds of X-ray photography.

During the X-ray photography in Step S18, each component may be adjusted according to the position irradiated with the X-ray beam BX. For example, for the panoramic photography in which the whole jaw, the upper jaw, or the lower jaw is set to the target, the case that the upper jaw anterior tooth FT1 or the lower jaw anterior tooth FT2 is irradiated with the X-ray may differ from the case that the tooth (such as the molar tooth) except the upper jaw anterior tooth FT1 and the lower jaw anterior tooth FT2 is irradiated with the X-ray in the irradiation direction of the X-ray beam BX, the height of the X-ray beam BX, the height of the X-ray detector 21, and the inclination angle of the X-ray detector 21.

While the invention is shown and described in detail in the above, the foregoing description is in all aspects illustrative and not restrictive. It should be, therefore, understood that numerous modifications and variations can be devised without departing from the scope of the invention.

What is claimed is:

[1. An X-ray photography apparatus comprising:

a support that supports an X-ray generator and an X-ray detector while said X-ray generator and said X-ray detector are opposed to each other so that a head of a patient can be interposed therebetween, the X-ray detector outputting an electric signal according to an intensity of an incident X-ray;

a moving mechanism that includes a turning part and a moving part, the turning part relatively turning said X-ray generator and said X-ray detector about the head by turning said support relative to the head about a predetermined turning axis, and the moving part moving said support relative to the head in a direction perpendicular to said turning axis;

a photographic region designation part that designates part of a row of teeth along a dental arch as a pseudo-intraoral radiography region;

an irradiation direction changing part that relatively changes an irradiation direction in which the head is irradiated with an X-ray with respect to an axial direction of a body axis of the patient; and a controller that controls said moving mechanism and said irradiation direction changing part, said controller controlling said moving mechanism while changing said irradiation direction according to a position of said pseudo intraoral radiography region, and the position of said pseudo intraoral radiography region being designated by said photographic region designation part.]

[2. The X-ray photography apparatus according to claim 1, said controller controlling said irradiation direction changing part such that the irradiation direction is substantially orthogonal to a tooth being a part of said row of teeth included in said pseudo intraoral radiography region.]

[3. The X-ray photography apparatus according to claim 1, said irradiation direction changing part including:

a first elevating mechanism that elevates an X-ray shielding member in parallel with an axial direction of said turning axis, said X-ray shielding member being mounted in front of said X-ray generator and forming an aperture through which the X-ray passes; and a second elevating mechanism that elevates said X-ray detector in the axial direction of said turning axis in conjunction with an elevating action of said X-ray shielding member, the elevating action of said X-ray shielding member being performed by the first elevating mechanism, and said controller controlling said first elevating mechanism to change said irradiation direction.]

[4. The X-ray photography apparatus according to claim 3, said irradiation direction changing part including a third elevating mechanism that elevates said support in parallel with the axial direction of said turning axis, and said controller including the third elevating mechanism to change a height position of said X-ray generator that emits the X-ray.]

[5. The X-ray photography apparatus according to claim 1, further comprising a mode setter that sets one of a pseudo intraoral radiography mode and a CT photography mode, a tomographic image of said pseudo intraoral radiography region being generated in the pseudo intraoral radiography mode, an X-ray CT image of the head being generated in the CT photography mode, and said controller controlling, when said mode setter sets said CT photography mode, an X-ray shielding member mounted in front of said X-ray generator to form the X-ray emitted from said X-ray generator into an X-ray cone beam, irradiating CT photography region with said X-ray cone beam, and controlling said irradiation direction changing part such that a center of said X-ray cone beam is incident to said CT photography region in a direction substantially orthogonal to the axial direction of said body axis.]

[6. The X-ray photography apparatus according to claim 5, said mode setter setting, when setting said CT photography mode, one of a first CT photography mode and a second CT photography mode, a region of both an upper jaw and a lower jaw being set to a target region of CT photography in the first CT photography mode, a region of one of said upper jaw and said lower jaw being set to said target region of said CT photography in said second CT photography mode, and said controller controlling said irradiation direction changing part such that a center axis of said X-ray cone beam is incident to said CT photography region corresponding to one of said first CT photography mode and said second CT photography mode in said direction substantially orthogonal to the axial direction of said body axis.]

[7. The X-ray photography apparatus according to claim 5, said controller controlling said X-ray shielding member to change a spread of said X-ray cone beam from a point of view in said axial direction of said body axis, said mode setter setting, when setting said CT photography mode, one of a local CT photography mode and a wide CT photography mode, only part of a region of a jaw being irradiated with said X-ray cone beam from the point of view in the axial direction of said body axis to be set to a CT photography target region in said local CT photography mode, a whole region of the jaw being irradiated with said X-ray cone beam from the point of view in the axial direction of said body axis to be set to said CT photography target region in said wide CT photography mode, and said controller controlling said irradiation direction changing part such that the center axis of said X-ray cone beam is incident to said CT photography region corresponding to one of said local CT photography mode and said wide CT photography mode in the direction substantially orthogonal to the axial direction of said body axis, said local CT photography mode and said wide CT photography mode being set by said mode setter.]

[8. The X-ray photography apparatus according to claim 5, said mode setter setting a panoramic photography mode in which panoramic photography of a jaw is performed, and said controller controlling, when said mode setter sets said panoramic photography mode, said X-ray shielding member mounted in front of said X-ray generator to form the X-ray emitted from said X-ray generator into an X-ray slit beam, and controlling said irradiation direction changing part such that a center of said X-ray slit beam is oriented upwardly with respect to the direction substantially orthogonal to the axial direction of said body axis.]

[9. The X-ray photography apparatus according to claim 1, further comprising a mode setter that selects one of a pseudo intraoral radiography mode and a panoramic photography mode, a tomographic image of said pseudo intraoral radiography region being generated in said pseudo intraoral radiography mode, panoramic photography of a jaw being performed in said panoramic photography mode, and said controller controlling, when said mode setter selects said panoramic photography mode, an X-ray shielding member mounted in front of said X-ray generator to form the X-ray emitted from the X-ray generator into an X-ray slit beam, and controlling said irradiation direction changing part such that a center of said X-ray slit beam is oriented upwardly with respect to the direction substantially orthogonal to the axial direction of said body axis.]

[10. The X-ray photography apparatus according to claim 1, said controller controlling said irradiation direction changing part such that said irradiation direction intersects a tooth being a part of said row of teeth included in said pseudo intraoral radiography region at a predetermined angle or an angle designated by an operator.]

[11. The X-ray photography apparatus according to claim 10, said controller controlling said irradiation direction changing part such that said irradiation direction is substantially orthogonal to the tooth being the part of said row of teeth included in said pseudo intraoral radiography region, or such that said irradiation direction is substantially orthogonal to a line that bisects an angle formed by a tooth axis of the tooth being the part of said row of teeth and a detection surface of said X-ray detector.]

[12. The X-ray photography apparatus according to claim 1, further comprising a detector tilt mechanism that tilts said X-ray detector with a direction orthogonal to said turning shaft as an X-ray detector rotational axis, said controller controlling said detector tilt mechanism to perform X-ray photography according to a position of said intraoral radiography region designated by said photographic region designation part.]

[13. The X-ray photography apparatus according to claim 12, said turning shaft extending in a direction orthogonal to a direction from said X-ray generator toward said X-ray detector.]

[14. The X-ray photography apparatus according to claim 13, said controller controlling said irradiation direction changing part and said detector tilt mechanism based on an inclination previously set with respect to the tooth included in said intraoral radiography region.]

[15. The X-ray photography apparatus according to claim 12, said controller inclining said X-ray detector about said X-ray detector rotational axis with respect to said X-ray generator to perform the pseudo intraoral radiography according to the position of said pseudo intraoral radiography region designated by said photographic region designation part.]

[16. The X-ray photography apparatus according to claim 12, said controller controlling said turning part and said moving part to perform panoramic photography.]

[17. The X-ray photography apparatus according to claim 16, said photographic region designation part receiving an input to set the upper jaw or the lower jaw to said photographic region, and said controller controlling said turning part and said moving part to perform the panoramic photography to the upper jaw or the lower jaw, the upper jaw or the lower jaw being set to said photographic region by said photographic region designation part.]

[18. The X-ray photography apparatus according to claim 16, said photographic region designation part receiving a manipulation to designate a part of the row of teeth along the dental arch as a partial panoramic photography region, and said controller controlling said turning part and said moving part to perform the panoramic photography to said partial panoramic photography region according to the position of said partial panoramic photography region designated by said photographic region designation part.]

[19. The X-ray photography apparatus according to claim 12, said controller locating said turning shaft in a center of the CT photography region to perform X-ray CT photography.]

*20. An X-ray photography apparatus comprising:*

*a support that supports an X-ray generator and an X-ray detector while said X-ray generator and said X-ray detector are opposed to each other so that a head of a patient can be interposed therebetween, the X-ray detector outputting an electric signal according to an intensity of an incident X-ray;*

*a head retainer that retains said head,*

*a pillar which is vertically-extending,*

*a frame to support said support and said head retainer, and vertically moves along said pillar;*

*said head retainer being connected to said frame and being vertically movable against said frame;*

*a first motor, a second motor and a third motor;*

*the first motor relatively turning said X-ray generator and said X-ray detector about the head by turning said support relative to the head about a predetermined turning axis; and*

*the second motor moving said support relative to the head in a direction perpendicular to said turning axis;*

*the third motor moving vertically said head retainer against said frame;*

*a shield that regulates an X-ray emitted from said X-ray generator;*

*said shield relatively changes an irradiation direction of the X-ray in which the head is irradiated with the X-ray with respect to an axial direction of a body axis of the patient, said shield forms an opening in a way said shield surrounds said opening for forming an X-ray beam;*

*a controller programmed to operate said first motor, said second motor and said third motor and a movement of said frame, head retainer and shield;*

*said controller controlling the movement of said head retainer so that a vertical position of said head retainer corresponds to a vertical position of said head;*

*said controller setting one of a CT photography mode, in which CT photography of the head is performed, and a panoramic photography mode, in which panoramic photography of a jaw is performed; wherein*

*said controller controls the movement of said shield, said frame and head retainer such that the X-ray emitted from said X-ray generator forms into an X-ray cone beam and a CT photography region is irradiated with said X-ray cone beam, a center of said X-ray cone beam is incident to said CT photography region in a direction substantially orthogonal to the axial direction of said body axis in said CT photography mode,*

*controlling the movement of said shield, said frame and head retainer such that the X-ray emitted from said X-ray generator forms into an X-ray slit beam and a center of said X-ray slit beam is oriented upwardly with*

*respect to the direction substantially orthogonal to the axial direction of said body axis in said panoramic photography mode;*

*said controller controls driving of said frame and said third motor to move said frame and said head retainer vertically in an opposite direction,*

*said controller setting one of a wide CT photography mode and a local CT photography mode as said CT photography mode, in said wide CT photography mode a whole region of a jaw as said CT photography region is irradiated by the X-ray cone beam, in said local CT photography mode only a part of a region of a jaw as said CT photography region is irradiated by the X-ray cone beam,*

*said controller controls said shield, said frame and head retainer such that the center of said X-ray cone beam is incident to any of said CT photography regions in the direction substantially orthogonal to the axial direction of said body axis when controls said shield to change a width of the opening.*

*21. The X-ray photography apparatus according to claim 20, wherein*

*said controller controls said shield, said frame and head retainer such that said CT photography region of only an upper jaw or a lower jaw is irradiated with said X-ray cone beam, the center of said X-ray cone beam is incident to said CT photography region of only the upper jaw or lower jaw in the direction substantially orthogonal to the axial direction of said body axis.*

*22. The X-ray photography apparatus according to claim 20, said shield forms an opening in a way said shield surrounds said opening for forming the X-ray cone beam, said controller controls the movement of the shield to change a width of the opening, so that said width for a first CT photography mode is larger than said width for a second CT photography mode, wherein in said first CT photography mode a region of both an upper jaw and a lower jaw is set to a first target region, and in said second CT photography mode a region of one of the upper jaw and the lower jaw is set to a second target region.*

*23. The X-ray photography apparatus according to claim 20, said shield comprising:*

*a pair of vertically-shielding plates that moves in a vertical direction to shield said X-ray; and*

*a pair of horizontally-shielding plates that moves in a horizontal direction to shield said X-ray, and*

*said X-ray cone beam and said X-ray slit beam are formed by said pair of vertically-shielding plates and said pair of horizontally-shielding plates.*

*24. The X-ray photography apparatus according to claim 20, further comprising:*

*a manipulation receiver receiving an input to set a panoramic photography region, wherein*

*said manipulation receiver receives an input to set an upper jaw or a lower jaw as a panoramic photography region in said panoramic photography, and*

*said controller controls said first motor and said second motor to perform the panoramic photography to the upper jaw or the lower jaw.*

*25. The X-ray photography apparatus according to claim 20, further comprising:*

*a manipulation receiver receiving an input to set a panoramic photography region, wherein*

*said manipulation receiver receives a manipulation to designate a part of a row of teeth along a dental arch as a partial panoramic photography region, and*

*said controller controls said first motor and said second motor to perform the panoramic photography to said partial panoramic photography region according to a position of said partial panoramic photography region designated by said manipulation receiver.*

* * * * *